United States Patent
Steinmeyer et al.

(10) Patent No.: US 7,115,758 B2
(45) Date of Patent: Oct. 3, 2006

(54) VITAMIN D DERIVATIVES WITH CYCLIC SUBSTRUCTURES IN THE SIDE CHAINS, PROCESS AND INTERMEDIATE PRODUCTS FOR THEIR PRODUCTION, AND THE USE FOR THE PRODUCTION OF PHARMACEUTICAL AGENTS

(75) Inventors: Andreas Steinmeyer, Berlin (DE); Katica Schwarz, Berlin (DE); Claudia Giesen, Berlin (DE); Martin Haberey, Berlin (DE); Marianne Fähnrich, Berlin (DE)

(73) Assignee: Schering AG, Berlin (DE)

( * ) Notice: Subject to any disclaimer, the term of this patent is extended or adjusted under 35 U.S.C. 154(b) by 20 days.

(21) Appl. No.: 10/303,916

(22) Filed: Nov. 26, 2002

(65) Prior Publication Data

US 2003/0149006 A1     Aug. 7, 2003

Related U.S. Application Data

(62) Division of application No. 09/624,608, filed on Jul. 24, 2000, now Pat. No. 6,603,031.

(30) Foreign Application Priority Data

Jul. 23, 1999 (DE) .................................. 199 35 771

(51) Int. Cl.
  *A61K 31/59* (2006.01)
  *C07C 401/00* (2006.01)
  *C07C 403/00* (2006.01)

(52) U.S. Cl. ............... 552/653; 514/167; 514/438; 514/439; 514/461; 514/471; 548/237; 548/239; 540/107

(58) Field of Classification Search ............ 552/653; 514/167, 438, 439, 461, 471; 540/200, 202; 548/237, 239
See application file for complete search history.

(56) References Cited

U.S. PATENT DOCUMENTS

| | | | |
|---|---|---|---|
| 5,384,313 A | | 1/1995 | DeLuca et al. |
| 5,384,314 A | | 1/1995 | Doran et al. |
| 5,494,905 A | * | 2/1996 | Hesse et al. ............... 514/167 |
| 5,532,228 A | * | 7/1996 | Neef et al. ............... 514/167 |
| 5,665,716 A | | 9/1997 | Kirsch et al. |
| 5,719,297 A | | 2/1998 | Tabe et al. |
| 5,756,733 A | * | 5/1998 | Hesse et al. ............... 544/164 |
| 5,929,056 A | | 7/1999 | Mourino et al. |
| 5,986,112 A | | 11/1999 | Tabe et al. |
| 6,127,559 A | * | 10/2000 | DeLuca et al. ............. 552/653 |
| 6,153,605 A | | 11/2000 | Barbier et al. |
| 6,177,586 B1 | | 1/2001 | Tabe et al. |
| 6,531,459 B1 | | 3/2003 | Steinmeyer et al. |
| 6,600,058 B1 | | 7/2003 | Steinmeyer et al. |
| 6,603,031 B1 | * | 8/2003 | Steinmeyer et al. ........ 552/653 |
| 2002/0049344 A1 | | 4/2002 | Steinmeyer et al. |

FOREIGN PATENT DOCUMENTS

| | | |
|---|---|---|
| DE | 40 03 854 | 8/1991 |
| EP | 0 441 467 | 2/1991 |
| EP | 0 421 561 | 4/1991 |
| EP | 0 717 034 | 6/1996 |
| EP | 0 808 832 | 11/1997 |
| EP | 0 854 1338 | 7/1998 |
| EP | 0 927 721 | 7/1999 |
| EP | 0 957 098 | 11/1999 |
| HU | 210 032 B | 8/1995 |
| WO | WO 94/00428 | 1/1994 |
| WO | WO 95/01960 | 1/1995 |
| WO | WO 95/03273 | 2/1995 |
| WO | WO 95/16672 | 6/1995 |
| WO | WO 95/25718 | 9/1995 |
| WO | WO 97/41096 | 11/1997 |
| WO | WO 98/47866 | 10/1998 |

OTHER PUBLICATIONS

Bouillon et al, Structure-Function Relationships in the Vitamin D Endocrine System, Endocrine Reviews, vol. 16, No. 2, pp. 200-257, 1995.*

(Continued)

*Primary Examiner*—Sabiha Qazi
(74) *Attorney, Agent, or Firm*—Millen, White, Zelano, Branigan, P.C.

(57) ABSTRACT

The invention relates to vitamin D derivatives of general formula I,

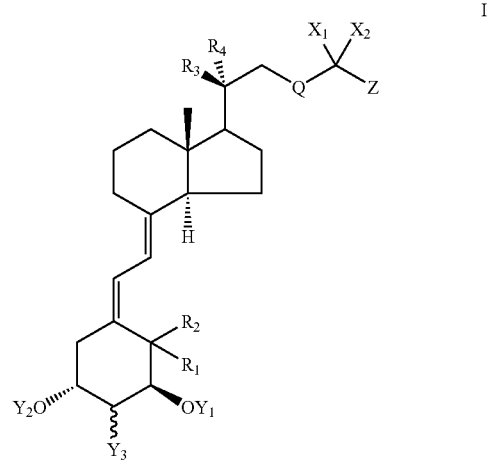

process for their production, intermediate products of the process as well as the use for the production of pharmaceutical agents.

31 Claims, No Drawings

OTHER PUBLICATIONS

Bouillon et al., DN 118:234338, HCAPLUS, abstract of WO 9221695.*
Takahashi et al., DN 114:229231, HCAPLUS, abstract of JP 03014558.*
Patridge et al., DN 100:22904, HCAPLUS, abstract of EP 86350.*
DeLuca et al., Tetrahederon Letters, vol. 32, No. 32, No. 52, pp. 7663-7666, 1991.
Nemoto, et al., "A Novel o-Quinodimethane Strategy for an Active Metabolite of Vitamin D3. A Total Synthesis of 25-Hydroxy Windaus-Grundmann Ketone", Tetrahedron Letters, vol. 31, pp. 6205-6208, 1990.
Hatakeyama et al., "A Novel Convergent Synthesis of (+)-1alpha, 25-dihydroxyvitamin D3 Using a Chromium(II)-Mediated Coupling Reaction", Journal of Organic Chemistry, vol. 56, pp. 461-463, 1991.
Duraisamy, et al., "Circular Dichroism of Isomeric 10-19-Dihydrovitamin D1", Journal of the American Chemical Society, vol. 105, pp. 3270-3273, 1983.
Dodo, et al., "Synthesis of a Novel Class of cdc25A Inhibitors from Vitamin D3", Bioorganic & Medicinal Chemistry Letters, vol. 10, pp. 615-617 (2000).
Semmier et al., "The Synthesis of 1α,25-Dihydroxycholecalciferol—A Metabolically Active Form of Vitamin $D_3$", Tetrahedron Letters No. 40, pp. 4147-4150 (1972).

* cited by examiner

VITAMIN D DERIVATIVES WITH CYCLIC SUBSTRUCTURES IN THE SIDE CHAINS, PROCESS AND INTERMEDIATE PRODUCTS FOR THEIR PRODUCTION, AND THE USE FOR THE PRODUCTION OF PHARMACEUTICAL AGENTS

The invention relates to new vitamin D derivatives of general formula I

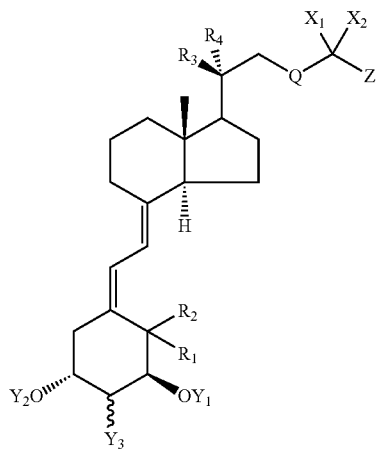

process for their production, intermediate products of the process as well as the use for the production of pharmaceutical agents.

PRIOR ART

Natural vitamins $D_2$ and $D_3$ are inherently biologically inactive and are converted into biologically active metabolites [1,25-dihydroxy vitamin $D_3$ (calcitriol) or $-D_2$] only after hydroxylation at C-atom 25 in the liver and at C-atom 1 in the kidney. The action of the active metabolites involves the regulation of the calcium and phosphate concentration in the serum; they counteract a dropping of the calcium concentration in the serum by increasing the calcium absorption in the intestine and under certain circumstances promoting calcium mobilization from the bones. Table 1 shows the structure of some known vitamin D derivatives:

TABLE 1

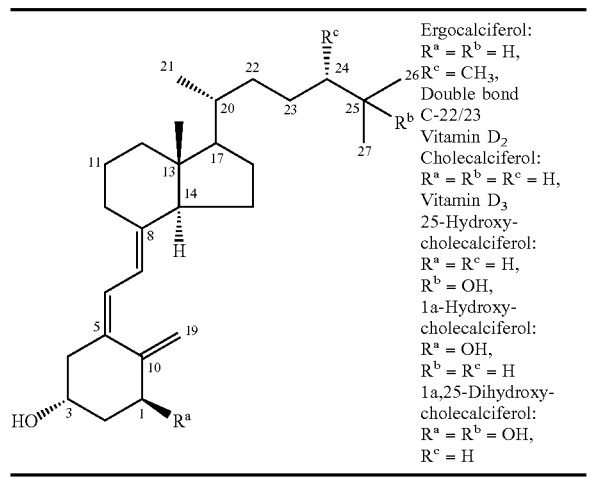

Ergocalciferol:
$R^a = R^b = H$,
$R^c = CH_3$,
Double bond
C-22/23
Vitamin $D_2$
Cholecalciferol:
$R^a = R^b = R^c = H$,
Vitamin $D_3$
25-Hydroxy-cholecalciferol:
$R^a = R^c = H$,
$R^b = OH$,
1a-Hydroxy-cholecalciferol:
$R^a = OH$,
$R^b = R^c = H$
1a,25-Dihydroxy-cholecalciferol:
$R^a = R^b = OH$,
$R^c = H$ In addition to their pronounced effect on the calcium-and phosphate metabolism, the active metabolites of vitamin $D_2$ and vitamin $D_3$ and their synthetic derivatives have a proliferation-inhibiting and differentiation-stimulating action on tumor cells and normal cells, such as, for example, skin cells. In addition, a pronounced effect on cells of the immune system (inhibiting of proliferation-and interleukin-2-synthesis of lymphocytes, increase of cytotoxicity and phagocytosis in vitro of monocytes) has been found, which manifests itself in an immunomodulatory action. Finally, because of a stimulating action on bone-forming cells, an increased formation of bone in normal and osteoporotic rats is found [R. Bouillon et al. "Short Term Course of 1,25(OH)$_2$D$_3$ Stimulates Osteoblasts But Not Osteoclasts," Calc. Tissue Int. 49, 168 (1991)]. All actions are mediated by binding to the vitamin D receptor. Because of the binding, the activity of specific genes is regulated.

When using biologically active metabolites of vitamins $D_2$ and $D_3$, a toxic effect on the calcium metabolism is produced (hypercalcemia).

By structural manipulations of the side chain, therapeutically usable effectiveness can be separated from undesirable hypercalcemic activity. A suitable structural variant is the introduction of a 24-hydroxy group.

1α-Cholecalciferols that are hydroxylated in 24-position are already described in DE 25 26 981. They have a lower toxicity than the corresponding non-hydroxylated 1α-cholecalciferol. Further, 24-hydroxy derivatives are described in the following patent applications: DE 39 33 034, DE 40 03 854, DE 40 34 730 (?), EP 0 421 561, EP 0 441 467, WO 87/00834, and WO 91/12238.

Finally, 25-carboxylic acid derivatives of calcitriol that are hydroxylated at C-24 are described in WO 94/07853, and said derivatives exhibit a more advantageous spectrum of action than calcitriol. The equivalent is also true for new vitamin D derivatives with other substituents at C-25 (WO 97/00242). While the ability to trigger a hypercalcemia is considerably weakened, proliferation-inhibiting and differentiation-stimulating actions are maintained. Generally, however, the introduction of the 24-hydroxyl group results in metabolic destabilization of the derivatives. For this reason, these compounds are only conditionally suitable for systemic administration.

There is therefore a need for new vitamin D derivatives that have as advantageous or improved a spectrum of action as the compounds that are described in the prior art (especially WO 94/07853 and WO 97/00242), but that are better suited for systemic administration owing to their higher metabolic stability.

The object of this patent application is therefore to make available such vitamin D derivatives. This object is achieved by the compounds that are disclosed in the claims.

This invention therefore relates to vitamin D derivatives of general formula I,

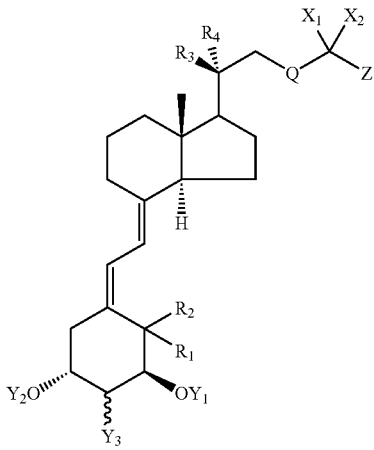

in which
- $Y_1$ and $Y_2$, independently of one another, each mean a hydrogen atom or a group —C(O)R$_5$,
- and $Y_3$ means a hydrogen atom or a hydroxy group, a halogen atom, a group —OC(O)R$_5$ or an —OR$_5$ group, whereby
  - $R_5$ stands for an aromatic radical with 5 to 12 C atoms or for an aliphatic, straight-chain or branched, saturated or unsaturated $C_1$–$C_{12}$ alkyl radical, which optionally is interrupted by 1–2 oxygen atoms, 1–2 sulfur atoms and/or 1–2 NH groups and/or optionally is substituted by 1–2 hydroxy groups, 1–2 amino groups, 1–2 SH groups, 1–2 COOH groups and/or 1–2 phenyl groups, and the group $Y_3$ can be present both in the 2α-situation and the epimeric 2β-situation,
- $R_1$ and $R_2$ each mean a hydrogen atom or together an exocyclic methylene group,
- $R_3$ and $R_4$, independently of one another, mean a hydrogen atom, a fluorine, chlorine or bromine atom, an alkyl group with 1 to 4 carbon atoms, together a methylene group or together with quaternary carbon atom 20 a 3- to 7-membered, saturated or unsaturated carbocyclic ring,
- Q means a straight-chain alkylene group with 1 to 5 carbon atoms,
- $X_1$ and $X_2$ together mean a double-bound keto-oxygen atom or, independently of one another, a hydrogen atom, a hydroxy group, an —OC(O)R$_5$ group, a fluorine, chlorine or bromine atom,
  - whereby $X_1$ and $X_2$, not at the same time, each should be a hydroxy group or each an —OC(O)R$_5$ group,
- Z means a carbocyclic or heterocyclic, optionally aromatic or heteroaromatic ring with 5 or 6 ring members or a condensed ring system that consists of a 5- and a 6-membered ring or two 6-membered rings, which can be substituted by one or more fluorine, chlorine, bromine or iodine atoms, one or more hydroxy groups, one or more COOR$_6$ groups, one or more $C_1$–$C_5$ alkyl groups, which in turn can be substituted by one or more fluorine, chlorine, bromine or iodine atoms, $C_1$–$C_6$ alkoxy groups and/or COOR$_6$ groups, whereby
  - $R_6$ stands for a $C_1$–$C_6$ alkyl group, a benzyl group or a phenyl group, and all possible epimers or diastereomers and mixtures thereof.

The invention also relates to a process for the production of the compounds according to the invention, intermediate products in the production process as well as the use of the compounds according to the invention for the production of pharmaceutical agents.

Especially advantageous embodiments of the invention are the subject of the subclaims.

The group —C(O)R$_5$, which is defined for $Y_1$ and $Y_2$, can carry 1 to 13 carbon atoms and is derived especially from saturated carboxylic acids. The radicals can be cyclic, acyclic, straight-chain or branched, saturated or unsaturated, carbocyclic or heterocyclic. The radicals are preferably derived from $C_1$–$C_9$ carboxylic acids. For example, formic acid, acetic acid, propionic acid, butanoic acid, pentanoic acid and pivalic acid can be mentioned. The groups $Y_1$ and $Y_2$, independently of one another, especially preferably can each mean a hydrogen atom or an acetyl, propionyl or pivaloyl group.

This explanation is also used for the group —OC(O)R$_5$, which is defined for the radicals $Y_3$, $X_1$ and $X_2$.

The group $Y_3$ can mean a hydrogen atom, a fluorine, chlorine or bromine atom or a hydroxy group, an OR$_5$ group or an —OC(O)R$_5$ group.

The alkoxy group $Y_3$ can mean straight-chain or branched, preferably unsubstituted and without interruption of heteroatoms, e.g., methoxy, ethoxy, propoxy, isopropoxy, butoxy, isobutoxy, t-butoxy. The preferred chain length is $C_1$–$C_9$.

Groups $R_3$ and $R_4$, independently of one another, can each mean a fluorine, chlorine or bromine atom, an alkyl group with 1 to 4 carbon atoms (methyl, ethyl, n-propyl, i-propyl, n-butyl, i-butyl, t-butyl), together a methylene group or together with quaternary carbon atom 20 a 3- to 7-membered, saturated or unsaturated carbocyclic ring.

For $R_3$ and $R_4$, the following preferred combinations apply: $R_3$=H, $R_4$=methyl or $R_3$=methyl, $R_4$H; $R_3$=$R_4$=methyl; $R_3$ and $R_4$ together form a methylene group or together with tertiary carbon atom 20 form a cyclopropyl ring.

Optional radical $R_5$ from the radical —OC(O)R$_5$ that is defined for $Y_3$, $X_1$ and $X_2$ is an organic radical with 1 to 12 C atoms, which are derived from longer carboxylic acids corresponding to a carbon atom. These radicals can be saturated or unsaturated, branched or unbranched, saturated or unsaturated, acyclic, carbocyclic or heterocyclic. Examples of radicals $R_5$ are methyl, ethyl, propyl, i-propyl, butyl or phenyl groups. The radicals of naturally occurring amino acids are also possible, however.

Preferred radical $R_5$ is derived from $C_1$ to $C_9$, especially $C_2$ to $C_5$ alkanecarboxylic acids, such as, for example, acetic acid, propionic acid, butyric acid or pivaloyl acid. Among the aromatic groups, the phenyl group and substituted phenyl groups are preferred.

Alkyl group $R_6$ can be straight-chain or branched, saturated or unsaturated, and it can mean, e.g., methyl, ethyl, propyl, butyl, isobutyl, tert-butyl, pentyl, isopentyl, neopentyl or hexyl.

The benzyl group and the phenyl group $R_6$ can be unsubstituted or else substituted by one or more halogen atom(s), hydroxy group(s), $C_1$–$C_4$ alkoxy group(s), CF$_3$ group(s) or amino group(s). The unsubstituted benzyl and phenyl groups are preferred.

Q is preferably to mean a methylene, ethylene or propylene group.

$X_1$ and $X_2$ preferably together are to mean a carbonyl group or X$_1$ means a hydroxyl group or a fluorine atom and X$_2$ means a hydrogen atom or X$_1$ means a hydrogen atom and X$_2$ means a hydroxyl group or a fluorine atom or X$_1$ means an —OC(O)R$_6$ group and X$_2$ means a hydrogen atom or X$_1$ means a hydrogen atom and X$_2$ means an —OC(O)R$_6$ group.

The two cases in which X$_1$=X$_2$=OH or X$_1$=X$_2$=O—C(O)R$_6$ were ruled out, since they are not chemically useful.

Z is preferably to mean a phenyl ring, which is substituted in ortho-, meta- or para-position with one or more methoxy, ethoxy, propoxy, hydroxy, fluorine, chlorine, bromine, methyl, ethyl, propyl or trifluoromethyl groups or Z is preferably to mean a heterocyclic system, such as, e.g., a furan, thiophene, pyrazole, pyrrole, oxazole, thiazole, imidazole ring, which can carry one or more methyl, ethyl or propyl groups at any position(s), which in turn can be substituted by halogen of the hydroxy groups and can be linked with the initial system via any C-atom, or Z is preferably to mean a heterocyclic condensed system, such as, e.g., a benzofuran, benzothiophene, benzimidazole, benzoxazole, benzothiazole, indole system, which can carry methyl, ethyl or propyl groups at any position, which in turn can be substituted by halogen of the hydroxy groups and can be linked with the initial system via any C-atom.

If the term halogen is used, fluorine, chlorine, bromine or iodine in connection with substitution patterns of radicals and preferably bromine or iodine as leaving groups in the process are meant.

Of the compounds of general formula I according to the invention, the following compounds are quite especially preferred:

(7E)-(1R,3R,24aR)-24a-(Oxazol-4-yl)-24a-homo-19-nor-9,10-secochola-5,7-diene-1,3,24a-triol (7E)-(1R,3R,24aS)-24a-(oxazol-4-yl)-24a-homo-19-nor-9,10-secochola-5,7-diene-1,3,24a-triol (5Z,7E)-(1S,3R,24aR)-24a-(oxazol-4-yl)-24a-homo-9,10-secochola-5,7,10(19)-triene-1,3,24a-triol (5Z,7E)-(1S,3R,24aS)-24a-(oxazol-4-yl)-24a-homo-9,10-secochola-5,7,10(19)-triene-1,3,24a-triol (7E)-(1R,3R,24aR)-24a-(thiazol-2-yl)-24a-homo-19-nor-9,10-secochola-5,7-diene-1,3,24a-triol (7E)-(1R,3R,24aS)-24a-(thiazol-2-yl)-24a-homo-19-nor-9,10-secochola-5,7-diene-1,3,24a-triol (7E)-(1R,3R)-1,3-dihydroxy-24a-(thiazol-2-yl-)-24-a-homo-19-nor-9,10-secochola-5,7-dien-24a-one (5Z,7E)-(1S,3R,24aR)-24a-(thiazol-2-yl)-24a-homo-9,10-secochola-5,7,10(19)-triene-1,3,24a-triol (5Z,7E)-(1S,3R,24aS)-24a-(thiazol-2-yl)-24a-homo-9,10-secochola-5,7,10(19)-triene-1,3,24a-triol (5Z,7E)-(1S,3R)-1,3-dihydroxy-24a-(thiazol-2-yl-)-24a-homo-9,10-secochola-5,7,10(19)-trien-24a-one (7E)-(1R,3R,24aR)-24a-(4-methylthiazol-2-yl)-24a-homo-19-nor-9,10-secochola-5,7-diene-1,3,24a-triol (7E)-(1R,3R,24aS)-24a-(4-methylthiazol-2-yl)-24a-homo-19-nor-9,10-secochola-5,7-diene-1,3,24a-triol (7E)-(1R,3R)-1,3-dihydroxy-24a-(4-methylthiazol-2-yl)-24a-homo-19-nor-9,10-secochola-5,7-dien-24a-one (5Z,7E)-(1S,3R,24aR)-24a-(4-methylthiazol-2-yl)-24a-homo-9,10-secochola-5,7,10(19)-triene-1,3,24a-triol (5Z,7E)-(1S,3R,24aS)-24a-(4-methylthiazol-2-yl)-24a-homo-9,10-secochola-5,7,10(19)-triene-1,3,24a-triol (5Z,7E)-(1S,3R)-1,3-dihydroxy-24a-(4-methylthiazol-2-yl)-24a-homo-9,10-secochola-5,7,10(19)-trien-24a-one (7E)-(1R,3R,24aR)-24a-(thien-2-yl)-24a-homo-19-nor-9,10-secochola-5,7-diene-1,3,24a-triol (7E)-(1R,3R,24aS)-24a-(thien-2-yl)-24a-homo-19-nor-9,10-secochola-5,7-diene-1,3,24a-triol (7E)-(1R,3R)-1,3-dihydroxy-24a-(thien-2-yl)-24a-homo-19-nor-9,10-secochola-5,7-dien-24a-one (5Z,7E)-(1S,3R,24aR)-24a-(thien-2-yl)-24a-homo-9,10-secochola-5,7,10(19)-triene-1,3,24a-triol (5Z,7E)-(1S,3R,24aS)-24a-(thien-2-yl)-24a-homo-9,10-secochola-5,7,10(19)-triene-1,3,24a-triol (7E)-(1R,2S,3R,24aR)-24a-thien-2-yl-24a-homo-19-nor-9,10-secochola-5,7-diene-1,2,3,24-tetrol (7E)-(1R,2S,3R,24aS)-24a-thien-2-yl-24a-homo-19-nor-9,10-secochola-5,7-diene-1,2,3,24-tetrol (7E)-(1R,2S,3R)-24a-thien-2-yl-1,2,3-trihydroxy-24a-homo-9,10-secochola-5,7-dien-24a-one (7E)-(1R,3R,24aR)-24a-(4-methylthien-2-yl)-24a-homo-19-nor-9,10-secochola-5,7-diene-1,3,24a-triol (7E)-(1R,3R,24aS)-24a-(4-methylthien-2-yl)-24a-homo-19-nor-9,10-secochola-5,7-diene-1,3,24a-triol (7E)-(1R,3R)-1,3-dihydroxy-24a-(4-methylthien-2-yl)-24a-homo-19-nor-9,10-secochola-5,7-dien-24a-one (5Z,7E)-(1S,3R,24aR)-24a-(4-methylthien-2-yl)-24a-homo-9,10-secochola-5,7,10(19)-triene-1,3,24a-triol (5Z,7E)-(1S,3R,24aS)-24a-(4-methylthien-2-yl)-24a-homo-9,10-secochola-5,7,10(19)-triene-1,3,24a-triol (5Z,7E)-(1S,3R)-1,3-dihydroxy-24a-(4-methylthien-2-yl)-24a-homo-9,10-secochola-5,7,10(19)-trien-24a-one (7E)-(1R,2S,3R,24aR)-24a-(4-methylthien-2-yl)-24a-homo-19-nor-9,10-secochola-5,7-diene-1,2,3,24-tetrol (7E)-(1R,2S,3R,24aS)-24a-(4-methylthien-2-yl)-24a-homo-19-nor-9,10-secochola-5,7-diene-1,2,3,24-tetrol (7E)-(1R,2S,3R)-24a-(4-methylthien-2-yl)-1,2,3-trihydroxy-24a-homo-19-nor-9,10-secochola-5,7-dien-24a-one (7E)-(1R,3R,24aR)-24a-(5-ethylthien-2-yl)-24a-homo-19-nor-9,10-secochola-5,7-diene-1,3,24a-triol (7E)-(1R,3R,24aS)-24a-(5-ethylthien-2-yl)-24a-homo-19-nor-9,10-secochola-5,7-diene-1,3,24a-triol (7E)-(1R,3R,24aR)-24a-[5-(2-hydroxyethyl)-4-methylthiazol-2-yl]-24a-homo-19-nor-9,10-secochola-5,7-diene-1,3,24a-triol (7E)-(1R,3R,24aS)-24a-[5-(2-hydroxyethyl)-4-methylthiazol-2-yl]-24a-homo-19-nor-9,10-secochola-5,7-diene-1,3,24a-triol (7E)-(1R,3R)-1,3-dihydroxy-24a-[5-(2-hydroxyethyl)-4-methylthiazol-2-yl]-24a-homo-19-nor-9,10-secochola-5,7-dien-24a-one (7E)-(1R,3R,24aR)-24a-(benzothiazol-2-yl)-24a-homo-19-nor-9,10-secochola-5,7-diene-1,3,24a-triol (7E)-(1R,3R,24aS)-24a-(benzothiazol-2-yl)-24a-homo-19-nor-9,10-secochola-5,7-diene-1,3,24a-triol (7E)-(1R,3R)-24a-(benzothiazol-2-yl)-1,3-dihydroxy-24a-homo-19-nor-9,10-secochola-5,7-dien-24a-one (7E)-(1R,3R,24aR)-24a-(benzofuran-2-yl)-24a-homo-19-nor-9,10-secochola-5,7-diene-1,3,24a-triol (7E)-(1R,3R,24aS)-24a-(benzofuran-2-yl)-24a-homo-19-nor-9,10-secochola-5,7-diene-1,3,24a-triol (7E)-(1R,3R)-24a-(benzofuran-2-yl)-1,3-dihydroxy-24a-homo-19-nor-9,10-secochola-5,7-dien-24a-one (7E)-(1R,3R,24aR)-24a-(benzothiophen-2-yl)-24a-homo-19-nor-9,10-secochola-5,7-diene-1,3,24a-triol (7E)-(1R,3R,24aS)-24a-(benzothiophen-2-yl)-24a-homo-19-nor-9,10-secochola-5,7-diene-1,3,24a-triol (7E)-(1R,3R)-24a-(benzothiophen-2-yl)-1,3-dihydroxy-24a-homo-19-nor-9,10-secochola-5,7-dien-24a-one (7E)-(1R,3R,24aR)-24a-(1-methylbenzimidazol-2-yl)-19-nor-9,10-secochola-5,7-diene-1,3,24a-triol (7E)-(1R,3R,24aS)-24a-(1-methylbenzimidazol-2-yl)-19-nor-9,10-secochola-5,7-diene-1,3,24a-triol (7E)-(1R,3R)-1,3-dihydroxy-24a-(1-methylbenzimidazol-2-yl)-24a-homo-19-nor-9,10-secochola-5,7-dien-24a-one (7E)-(1R,3R)-1-(1,3-dihydroxy-24a-homo-19-nor-9,10-secochola-5,7-dien-24a-yl)-3-[(4-methoxyphenyl)-methoxy]-1H-pyrazole-4-carboxylic acid ethyl ester (7E)-(1R,3R)-1-(1,3-dihydroxy-24a-homo-19-nor-9,10-secochola-5,7-dien-24a-yl)-3-hydroxy-1H-pyrazole-4-carboxylic acid ethyl ester (7E)-(1R,3R,24aR)-24a-(4-methylphenyl)-24a-homo-19-nor-9,10-secochola-5,7-diene-1,3,24a-triol (7E)-(1R,3R,24aS)-24a-(4-methylphenyl)-24a-homo-19-nor-9,10-secochola-5,7-diene-1,3,24a-triol (7E)-(1R,3R)-1,3-dihydroxy-24a-(4-methylphenyl)-24a-homo-19-nor-9,10-secochola-5,7-dien-24a-one (7E)-(1R,2R,3R,24aR)-24a-(4-methylphenyl)-24a-homo-19-nor-9,10-secochola-5,7-diene-1,2,3,24a-tetrol (7E)-(1R,RS,3R,24aS)-24a-(4-methylphenyl)-24a-homo-19-nor-9,10-secochola-5,7-diene-1,2,3,24a-tetrol (7E)-(1R,3R,24aR)-24a-(4-trifluoromethylphenyl)-19-nor-9,10-secochola-5,7-diene-1,3,24a-triol (7E)-(1R,3R,24aS)-24a-(4-trifluoromethylphenyl)-19-nor-9,10-secochola-5,7-diene-1,3,24a-triol (7E)-(1R,3R)-1,3-dihydroxy-24a-(4-trifluoromethylphenyl)-24a-homo-19-nor-9,10-secochola-5,7-dien-24a-one (7E)-(1R,3R,24aR)-24a-(4-methoxyphenyl)-24a-homo-19-nor-9,10-secochola-5,7-diene-1,3,24a-triol (7E)-(1R,3R,24aS)-24a-(4-methoxyphenyl)-24a-homo-19-nor-9,10-secochola-5,7-diene-1,3,24a-triol (7E)-(1R,3R)-1,3-dihydroxy-24a-(4-methoxyphenyl)-24a-homo-19-nor-9,10-secochola-5,7-dien-24a-one (7E)-(1R,3R,20S,24aR)-24a-(thiazol-2-yl)-24a-homo-19-nor-9,10-secochola-5,7-diene-1,3,24a-triol (7E)-(1R,3R,20S,24aS)-24a-(thiazol-2-yl)-24-a-homo-19-nor-9,10-secochola-5,7-diene-1,3,24a-triol (7E)-(1R,3R,20S)-1,3-dihydroxy-24a-(thiazol-2-yl)-24-a-homo-19-nor-9,10-secochola-5,7-dien-24a-one (5Z,7E)-(1S,3R,20S,24aR)-24a-(thiazol-2-yl)-24a-homo-9,10-secochola-5,7,10(19)-triene-1,3,24a-triol (5Z,7E)-(1S,3R,20S,24aS)-24a-(thiazol-2-yl)-24a-homo-9,10-secochola-5,7,10(19)-triene-1,3,24a-triol (5Z,7E)-(1S,3R,20S)-1,3-dihydroxy-24a-(thiazol-2-yl)-24a-homo-9,10-secochola-5,7,10(19)-trien-24a-one (5Z,7E)-(1S,3R,24S)-24-(thiazol-2-yl)-9,10-secochola-5,7,10(19)-triene-1,3,24-triol (5Z,7E)-(1S,3R,24R)-24-(thiazol-2-yl)-9,10-secochola-5,7,10(19)-triene-1,3,24-triol (5Z,7E)-(1S,3R)-1,3-dihydroxy-24-(thiazol-2-yl)-9,10-secochola-5,7,10(19)-trien-24-one (7E)-(1R,3R,20S,24aR)-24a-(oxazol-4-yl)-24a-homo-19-nor-9,10-secochola-5,7-diene-1,3,24a-triol (7E)-(1R,3R,20S,24aS)-24a-(oxazol-4-yl)-24-a-homo-19-nor-9,10-secochola-5,7-diene-1,3,24a-triol (7E)-(1R,3R,20S)-1,3-dihydroxy-24a-(oxazol-4-yl)-24-a-homo-19-nor-9,10-secochola-5,7-dien-24a-one (5Z,7E)-(1S,3R,20S,24aR)-24a-(oxazol-4-yl)-24a-homo-9,10-secochola-5,7,10(19)-triene-1,3,24a-triol (5Z,7E)-(1S,3R,20S,24aS)-24a-(oxazol-4-yl)-24a-homo-9,10-secochola-5,7,10(19)-triene-1,3,24a-triol (5Z,7E)-(1S,3R,20S)-1,3-dihydroxy-24a-(oxazol-4-yl)-24a-homo-9,10-secochola-5,7,10(19)-trien-24a-one (5Z,7E)-(1S,3R,24R)-24-(oxazol-4-yl)-9,10-secochola-5,7,10(19)-triene-1,3,24-triol (5Z,7E)-(1S,3R,24S)-24-(oxazol-4-yl)-9,10-secochola-5,7,10(19)-triene-1,3,24-triol (5Z,7E)-(1S,3R)-1,3-dihydroxy-24-(oxazol-4-yl)-9,10-secochola-5,7,10(19)-trien-24-one (7E)-(1R,3R,20S,24aR)-24a-(4-methylthiazol-2-yl)-24a-homo-19-nor-9,10-secochola-5,7-diene-1,3,24a-triol (7E)-(1R,3R,20S,24aS)-24a-(4-methylthiazol-2-yl)-24-a-homo-19-nor-9,10-secochola-5,7-diene-1,3,24a-triol (7E)-(1R,3R,20S)-1,3-dihydroxy-24a-(4-methylthiazol-2-yl)-24-a-homo-19-nor-9,10-secochola-5,7-dien-24a-one (5Z,7E)-(1S,3R,20S,24aR)-24a-(4-methylthiazol-2-yl)-24a-homo-9,10-secochola-5,7,10(19)-triene-1,3,24a-triol (5Z,7E)-(1S,3R,20S,24aS)-24a-(4-methylthiazol-2-yl)-24a-homo-9,10-secochola-5,7,10(19)-triene-1,3,24a-triol (5Z,7E)-(1S,3R,20S)-1,3-dihydroxy-24a-(4-methylthiazol-2-yl)-24a-homo-9,10-secochola-5,7,10(19)-trien-24a-one (5Z,7E)-(1S,3R,24R)-24-(4-methylthiazol-2-yl)-9,10-secochola-5,7,10(19)-triene-1,3,24-triol (5Z,7E)-(1S,3R,24S)-24-(4-methylthiazol-2-yl)-9,10-secochola-5,7,10(19)-triene-1,3,24-triol (5Z,7E)-(1S,3R)-1,3-dihydroxy-24-(4-methylthiazol-2-yl)-9,10-secochola-5,7,10(19)-trien-24-one (7E)-(1R,3R,20S,24aR)-24a-(4-methylthien-2-yl)-24a-homo-19-nor-9,10-secochola-5,7-diene-1,3,24a-triol (7E)-(1R,3R,20S,24aS)-24a-(4-methylthien-2-yl)-24-a-homo-19-nor-9,10-secochola-5,7-diene-1,3,24a-triol (7E)-(1R,3R,20S)-1,3-dihydroxy-24a-(4-methylthien-2-yl)-24-a-homo-19-nor-9,10-secochola-5,7-dien-24a-one (5Z,7E)-(1S,3R,20S,24aR)-24a-(4-methylthien-2-yl)-24a-homo-9,10-secochola-5,7,10(19)-triene-1,3,24a-triol (5Z,7E)-(1S,3R,20S,24aS)-24a-(4-methylthien-2-yl)-24a-homo-9,10-secochola-5,7,10(19)-triene-1,3,24a-triol (5Z,7E)-(1S,3R,20S)-1,3-dihydroxy-24a-(4-methylthien-2-yl)-24a-homo-9,10-secochola-5,7,10(19)-trien-24a-one (5Z,7E)-(1S,3R,24R)-24-(4-methylthien-2-yl)-9,10-secochola-5,7,10(19)-triene-1,3,24-triol (5Z,7E)-(1S,3R,24S)-24-(4-methylthien-2-yl)-9,10-secochola-5,7,10(19)-triene-1,3,24-triol (5Z,7E)-(1S,3R)-1,3-dihydroxy-24-(4-methylthien-2-yl)-9,10-secochola-5,7,10(19)-trien-24-one (7E)-(1R,3R,20S,24aR)-24a-(thien-2-yl)-24a-homo-19-nor-9,10-secochola-5,7-diene-1,3,24a-triol (7E)-(1R,3R,20S,24aS)-24a-(thien-2-yl)-24-a-homo-19-nor-9,10-secochola-5,7-diene-1,3,24a-triol (7E)-(1R,3R,20S)-1,3-dihydroxy-24a-(thien-2-yl)-24-a-homo-19-nor-9,10-secochola-5,7-dien-24a-one (5Z,7E)-(1S,3R,20S,24aR)-24a-(thien-2-yl)-24a-homo-9,10-secochola-5,7,10(19)-triene-1,3,24a-triol (5Z,7E)-(1S,3R,20S,24aS)-24a-(thien-2-yl)-24a-homo-9,10-secochola-5,7,10(19)-triene-1,3,24a-triol (5Z,7E)-(1S,3R,20S)-1,3-dihydroxy-24a-(thien-2-yl)-24a-homo-9,10-secochola-5,7,10(19)-trien-24a-one (5Z,7E)-(1S,3R,24R)-24-(thien-2-yl)-9,10-secochola-5,7,10(19)-triene-1,3,24-triol (5Z,7E)-(1S,3R,24S)-24-(thien-2-yl)-9,10-secochola-5,7,10(19)-triene-1,3,24-triol (5Z,7E)-(1S,3R)-1,3-dihydroxy-24-(thien-2-yl)-9,10-secochola-5,7,10(19)-trien-24-one (5Z,7E)-(1S,3R,24S)-24-(4-methylthiazol-2-yl)-9,10-secochola-5,7,10(19)-triene-1,3,24-triol (5Z,7E)-(1S,3R,24R)-24-(4-methylthiazol-2-yl)-9,10-secochola-5,7,10(19)-triene-1,3,24-triol (5Z,7E)-(1S,3R)-1,3-dihydroxy-24-(4-methylthiazol-2-yl)-9,10-secochola-5,7,10(19)-trien-24-one (5Z,7E)-(1S,3R,24S)-24-(thien-2-yl)-9,10-secochola-5,7,10(19)-triene-1,3,24-triol (5Z,7E)-(1S,3R,24R)-24-(thien-2-yl)-9,10-secochola-5,7,10(19)-triene-1,3,24-triol (5Z,7E)-(1S,3R)-1,3-dihydroxy-24-(thien-2-yl)-9,10-secochola-5,7,10(19)-trien-24-one (5Z,7E)-(1S,3R,24S)-24-(4-methylthien-2-yl)-9,10-seco-chola-5,7,10(19)-triene-1,3,24-triol (5Z,7E)-(1S,3R,24R)-24-(4-methylthien-2-yl)-9,10-seco-chola-5,7,10(19)-triene-1,3,24-triol (5Z,7E)-(1S,3R)-1,3-dihydroxy-24-(4-methylthien-2-yl)-9,10-secochola-5,7,10(19)-trien-24-one (7E)-(1R,3R,24aR)-24a-fluoro-24a-(thiazol-2-yl)-24a-homo-19-nor-9,10-secochola-5,7-diene-1,3-diol (7E)-(1R,3R,24aS)-24a-fluoro-24a-(thiazol-2-yl)-24a-homo-19-nor-9,10-secochola-5,7-diene-1,3-diol (5Z,7E)-(1S,3R,24aR)-24a-fluoro-24a-(thiazol-2-yl)-24a-homo-9,10-secochola-5,7,10(19)-triene-1,3-diol (5Z,7E)-(1S,3R,24aS)-24a-fluoro-24a-(thiazol-2-yl)-24a-homo-9,10-secochola-5,7,10(19)-triene-1,3-diol (7E)-(1R,3R,24aR)-24a-(acetyloxy)-24a-(thiazol-2-yl)-24a-homo-19-nor-9,10-secochola-5,7-diene-1,3,24a-triol (7E)-(1R,3R,24aS)-24a-(acetyloxy)-24a-(thiazol-2-yl)-24a-homo-19-nor-9,10-secochola-5,7-diene-1,3,24a-triol (7E)-(1R,3R,24aR)-24a-(2,2-dimethylpropanoyloxy)-24a-(thiazol-2-yl)-24a-homo-19-nor-9,10-secochola-5,7-diene-1,3,24a-triol (7E)-(1R,3R,24aS)-24a-(2,2-dimethylpropanoyloxy)-24a-(thiazol-2-yl)-24a-homo-19-nor-9,10-secochola-5,7-diene-1,3,24a-triol (7E)-(1R,3R)-2-bromo-24a-(thiazol-2-yl)-24a-homo-19-nor-9,10-secochola-5,7-diene-1,3,24a-triol.

The substances according to the invention have a considerably higher metabolic stability than the structurally related compounds of the prior art and are therefore suitable in a special way for systemic administrations.

Relative to the structurally related compounds of the prior art, some of the substances according to the invention are also characterized in that they show a stronger action on cell differentiation, whereby the action on the calcium balance does not increase.

Others of the substances according to the invention, however, exhibit an antagonistic or partial agonistic profile of action, which makes possible new uses.

Determination of Biological Activity

The vitamin D activity of the substances according to the invention is determined with the aid of the calcitriol-receptor test. It is carried out using a protein extract from the intestines of juvenile pigs. Receptor-containing protein extract is incubated in a test tube with $^3$H-calcitriol ($5 \times 10^{-10}$ mol/l) in a reaction volume of 0.27 ml in the absence and in the presence of test substances for two hours at 4° C. To separate free and receptor-bound calcitriol, a charcoal-dextran absorption is carried out. To this end, 250 μl of a charcoal-dextran suspension is fed to each test tube and incubated at 4° C. for 20 minutes. Then, the samples are centrifuged at 10,000 g for 5 minutes at 4° C. The supernatant is decanted and measured in a β-counter after 1 hour of equilibration in Picofluor 15™.

The competition curves that are obtained at various concentrations of test substance as well as of reference substance (unlabeled calcitriol) at constant concentration of the reference substance ($^3$H-calcitriol) are placed in relation to one another, and a competition factor (KF) is determined.

It is defined as a quotient of the concentrations of the respective test substance and the reference substance, which are necessary for 50% competition:

$$KF = \frac{\text{concentration of test substance at 50\% competition}}{\text{concentration of reference substance at 50\% competition}}$$

To determine the acute hypercalcemic action of various calcitriol derivatives, the test that is described below is carried out:

The action of control (solution base), reference substance (1,25-dihydroxy vitamin $D_3$=calcitriol) and test substance is tested in each case after one-time subcutaneous administration in groups of 10 healthy male rats (140–170 g). During the testing time, the rats are kept in special cages to determine the excretion of water and mineral substances. Urine is collected in 2 fractions (0–16 hours and 16–22 hours). An oral dose of calcium (0.1 mmol of calcium in 6.5% alpha-hydroxypropyl-cellulose, 5 ml/animal) replaces at 1600 hours the calcium intake that is lacking by food deprivation. At the end of the test, the animals are killed by decapitation and exsanguinated to determine the serum-calcium values. For the primary screen test in vivo, an individual standard dose (200 μg/kg) is tested. For selected substances, the result is supported by establishing a dose-effect relation.

A hypercalcemic action is shown in serum-calcium level values that are higher than in the control.

The significance of differences occurring between substance groups and controls and between test substance and reference substance are supported with suitable statistical processes. The result is indicated as dose ratio DR (DR=factor of test substance dose/reference substance dose for comparable actions).

The differentiation-stimulating action of calcitriol analogues is also detected quantitatively.

It is known in the literature [D. J. Mangelsdorf et al., J. Cell. Biol. 98: 391 (1984)] that the treatment of human leukemia cells (promyelocyte cell line HL 60) in vitro with calcitriol induces the differentiation of cells to macrophages.

HL 60 cells are cultivated in tissue culture medium (RPMI 10% fetal calf serum) at 37° C. in an atmosphere of 5% $CO_2$ in air.

For substance testing, the cells are centrifuged off, and $2.0 \times 10^5$ cells/ml in phenol red-free tissue culture medium is taken up. The test substances are dissolved in ethanol and diluted with tissue culture medium without phenol red to the desired concentration. The dilution stages are mixed with the cell suspension at a ratio of 1:10, and 100 μl each of this cell suspension that is mixed with substance is pipetted into an indentation of a 96-hole plate. For control, a cell suspension is mixed analogously with the solvent.

After incubation for 96 hours at 37° C. in 5% $CO_2$ in air, 100 μl of an NBT-TPA solution (nitro blue tetrazolium (NBT), final concentration in the batch of 1 mg/ml, tetradecanoyl phorbolmyristate-13-acetate (TPA), final concentration in the batch of $2 \times 10^{-7}$ mol/l) is pipetted into each indentation of the 96-hole-plate in the cell suspension.

By incubation for 2 hours at 37° C. and 5% $CO_2$ in air, NBT is reduced to insoluble formazan because of the intracellular oxygen radical release, stimulated by TPA, in the cells that are differentiated to macrophages.

To complete the reaction, the indentations of the 96-hole plate are suctioned off, and the cells are affixed to the bottom of the plate by adding methanol and dried after affixing. To dissolve the intracellular formazan crystals that are formed, 100 μl of potassium hydroxide (2 mol/l) and 100 μl of dimethyl sulfoxide are pipetted into each indentation and ultrasonically treated for 1 minute. The concentration of formazan is measured by spectrophotometry at 650 nm.

As a yardstick for the differentiation induction of HL 60 cells to macrophages, the concentration of formed formazan applies. The result is indicated as a dose ratio (DR=factor of test substance dose/reference substance dose for comparable semi-maximum actions).

The results of the calcitriol-receptor test and the determination of the dose ratio of the differentiation induction of HL 60 cells and the dose ratio for hypercalcemia are summarized below:

Examples of Test Substances:
(7E)-(1R,3R,2aR)-24a-(Oxazol-4-yl)-24a-homo-19-nor-9,10-secochola-5,7-diene-1,3,24a-triol 16a
(5Z,7E)-(1S,3R,24aR)-24a-(oxazol-4-yl)-24a-homo-9,10-secochola-5,7,10(19)-triene-1,3,24a-triol 20a
(7E)-(1R,3R,24aS)-24a-(thien-2-yl)-24a-homo-19-nor-9,10-secochola-5,7-diene-1,3,24a-triol 55b
(7E)-(1R,3R)-1,3-dihydroxy-24a-(thien-2-yl)-24a-homo-19-nor-9,10-secochola-5,7-dien-24a-one 57
(5Z,7E)-(1S,3R,24R)-24-(thiazol-2-yl)-9,10-secochola-5,7,10(19)-triene-1,3,24a-triol 217a

|  | KF | DR (HL 60) | DR (Ca) |
| --- | --- | --- | --- |
| 16a | 5 | 5 | >30 |
| 20a | 3 | 2 | >50 |
| 55b | 5 | 8 | >100 |
| 57 | 12 | 2 | >350 |
| 217a | 7 | 100 | >300 |
| Calcitriol | 1 | 1 | 1 |

In addition to a considerable affinity to the vitamin D receptor, the compounds listed show a pronounced cell-differentiating activity.

The induction of a hypercalcemia is carried out, however, only at very much higher doses than in the case of calcitriol.

By the reduced property of triggering a hypercalcemia as well as the high metabolic stability, the substances according to the invention are suitable in a special way for the production of pharmaceutical agents for the treatment of diseases that are characterized by hyperproliferation and deficient cell differentiation. Included in these are, for example, hyperproliferative diseases of the skin (psoriasis, pityriasis subia pilasis, acne, ichthyosis) and pruritus, as well as tumor diseases and precancerous stages (for example, tumors of the intestines, carcinomas of the breast, lung tumors, prostate carcinomas, leukemias, T-cell lymphomas, melanomas, Betazell carcinoma, squamous carcinoma, actinic keratoses, cervix dysplasias, and metastasizing tumors of any type).

Also, for the treatment and prophylaxis of diseases that are characterized by a disequilibrium of the immune system, the substances according to the invention are suitable. These include eczemas and diseases of the atopic Formon series and inflammatory diseases (rheumatoid arthritis, respiratory tract diseases, e.g., asthma), as well as auto-immune diseases, such as, for example, multiple sclerosis, diabetes mellitus type I, myasthenia gravis, lupus erythematosus, scleroderma, bullous skin diseases (pemphigus, pemphigoid), further rejection reactions in the case of autologous, allogeneic or xenogeneic transplants, as well as AIDS. In all of these diseases, the new compounds of general formula I can be combined advantageously with other substances that have an immunosuppressive action, such as cyclosporin A, FK 506, rapamycin and anti-CD 4-antibodies.

The substances are also suitable for therapy of secondary hyperparathyroidism and renal osteodystrophia because of the property of calcitriols to drop the parathormone synthesis.

Owing to the presence of the vitamin D receptor in the insulin-producing cells of the pancreas, the substances are suitable by increasing the insulin secretion for the therapy of diabetes mellitus type II.

Further, it has been found, surprisingly enough, that by topical application of the compounds according to the invention on the skin of mice, rats and guinea pigs, an increased reddening of the skin and increase of the thickness of the epidermis can be induced. The increase in the reddening of the skin is-determined based on the increase in the red value of the skin surface that can be quantified with a colorimeter. The red value is typically increased 1.5-fold after the substance (dose 0.003%) is administered three times at intervals of 24 hours. The increase in the thickness of the epidermis is quantified in the histological preparation. It is typically increased 2.5-fold. The number of proliferating epidermal cells (cells in the S-phase of the cell cycle) is determined by flow cytometry and is typically increased by a factor of 6.

These properties of the derivatives in the vitamin D series according to the invention can appear suitable for therapeutic use in the case of atrophic skin, as it occurs in natural skin aging because of increased light exposure or medicinally-induced skin atrophy by treatment with glucocorticoids.

Further, it can be assumed that wound healing can be accelerated by topical application with the new compounds.

In cell populations of the hair follicle, which contribute decisively to hair growth or to hair cycle regulation, it was possible to detect vitamin $D_3$ receptor proteins [W. E. Stumpf et al., Cell Tissue Res. 238, 489 (1984); P. Milde et al., J. Invest. Dermatol. 97, 230 (1991)]. In addition, in vitro findings on isolated hair follicle keratinocytes show a proliferation-inhibiting and differentiation-stimulating influence of $1,25\text{-}(OH)_2\text{-}D_3$.

From clinical observations, it is known that the vitamin $D_3$-resistant rickets often accompanies alopecia, which develops in early infancy. Experimental findings show that the vitamin $D_3$-bonding site of the VDR in this disease mutates, i.e., is defective [K. Kristjansson et al., J. Clin. Invest. 92, 12 (1993)]. Keratinocytes, which were isolated from the hair follicles of these patients, do not react in vitro to the addition of $1,25\text{-}(OH)_2D_3$ [S. Arase et al., J. Dermatol. Science 2, 353 (1991)].

These findings indicate a decisive role for $1,25\text{-}(OH)_2D_3$ in the regulation of hair growth.

These analogues are therefore especially suitable for the production of pharmaceutical agents for the treatment of diseases which accompany disrupted hair growth (androgenetic alopecia, alopecia areata/totalis, chemotherapy-induced alopecia) or for supporting physiological hair growth without causing the side-effects of calcitriol (especially hypercalcemia).

Senile and postmenopausal osteoporosis is characterized by an increased bone turnover with an overall negative balance. Owing to the bone shrinkage especially of trabecular bones, fractures result to an increased extent. Owing to the stimulating action of calcitriol, both in the number and the conduct of synthesis of cells forming new bones (osteoblasts), the substances according to the invention are suitable for therapy and prophylaxis of senile and postmenopausal osteoporosis (EP 0 634 173 A1), of steroid-induced osteoporosis as well as for accelerated healing of arthroplasties without causing the side-effects of calcitriol (especially hypercalcemia). For the therapy of various forms of osteoporosis, they can be combined advantageously with estradiol or other derivatives of estrogen.

Finally, it was possible to show that calcitriol increases the synthesis of a growth substance for nerve cells (nerve growth factor) [M. S. Saporito et al. Brain Res. 633, 189 (1994)]. The compounds according to the invention are therefore also suitable for treating degenerative diseases of the peripheral and central nervous system, such as Alzheimer's disease and amyotrophic lateral sclerosis.

In addition, it has been found that certain compounds of general formula I in HL 60 cells antagonize, surprisingly enough, the action of calcitriol.

Such compounds can be used for the therapy of hypercalcemias, such as, for example, in hypervitaminosis D or intoxication with calcitriol and calcitriol-like active substances, or in the case of increased extrarenal calcitriol synthesis in granulomatous diseases (sarcoidosis, tuberculosis). Also, paraneoplastic hypercalcemias (for example, in osteolytic metastases and tumors with increased synthesis of parathormone-related peptides) as well as in hypercalcemias in the case of hyperparathyroidism.

In addition, calcitriol antagonists can be used for birth control. In the reproductive tracts of female and male animals, the vitamin D receptor is expressed. It is known that the female and-male fertility of vitamin-D-deficient animals is reduced. By short-term substitution of calcitriol, the reproductive output can be increased. Calcitriol antagonists are therefore able to influence female and male fertility.

Since calcitriol, under certain conditions, shows an immunosuppressive action, calcitriol receptor antagonists can also be used as immunostimulants, e.g., in the case of weak defenses against infections, AIDS.

Calcitriol is known to be able to modulate hair growth. Calcitriol antagonists can therefore be used therapeutically in the case of undesirable hair growth, e.g., in hirsutism.

Vitamin D has long been known to play a stimulating role in the formation of arteriosclerotic plaque. In such vascular lesions, a calcitriol-regulated protein, osteopontin, is found to be increased, to which a role in vascular sclerosis is attributed [R. Eisenstein et al. Arch. Path. 77, 27 (1964), L. A. Fitzpatrick et al., J. Clin. Invest. 94, 1597 (1994)]. Calcitriol antagonists are therefore suitable for therapy and prophylaxis of all types of arteriosclerosis.

Finally, calcitriol antagonists are suitable because of the property of calcitriol to increase unspecific immune reactions of monocytic cells, for therapy of inflammatory diseases, especially of a chronic nature, such as rheumatoid arthritis, Crohn's disease, ulcerative colitis, and granulomatous diseases such as sarcoidosis and other foreign-body reactions.

For all listed therapeutic applications, it is true that the compounds according to the invention are able to achieve a therapeutic action in the above-mentioned clinical pictures without causing the side-effects of calcitriol (especially hypercalcemia).

This invention thus relates to pharmaceutical preparations that contain at least one compound according to general formula I together with a pharmaceutically compatible vehicle.

The compounds can be formulated as solutions in pharmaceutically compatible solvents or as emulsions, suspensions or dispersions in suitable pharmaceutical solvents or vehicles or as pills, tablets or capsules, which contain solid vehicles in a way known in the art.

For topical use, the compounds are advantageously formulated as creams or ointments or in a similar form of pharmaceutical agent that is suitable for topical use. Each such formulation can also contain other pharmaceutically compatible and nontoxic adjuvants, such as, e.g., stabilizers, antioxidants, binders, dyes, emulsifiers or flavoring additives.

The compounds are advantageously administered by injection, intravenous infusion of suitable sterile solutions, as an aerosol via bronchial tubes and lungs, or as oral dosage via the alimentary tract or topically in the form of creams, ointments, lotions or suitable transdermal patches, as is described in EP-A 0 387 077.

The daily dose is approximately 0.1 μg/patient/day–1000 μg/patient/day, preferably 1.0 μg/patient/day–500 μg/patient/day.

Process for the Production of the Compounds According to the Invention

The production of the vitamin D derivatives of general formula I is carried out according to the invention from a compound of general formula II,

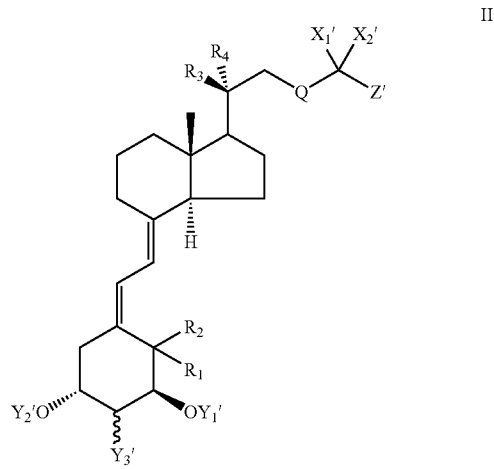

II in which $Y'_1$ and $Y'_2$ mean hydroxy protective groups, and $Y'_3$ is a hydrogen atom, a halogen atom or a protected hydroxy group.

$X'_1$, $X'_2$ and $Z'$ are distinguished from $X_1$, $X_2$ and $Z$ in that optionally present hydroxy groups or keto groups can be present in protected form.

The protective groups are preferably alkyl-, aryl- or mixed alkylaryl-substituted silyl groups, e.g., the trimethylsilyl (TMS), triethylsilyl (TES), tert-butyldimethylsilyl (TBDMS), tert-butyldiphenylsilyl (TBDPS) or triisopropylsilyl (TIPS) groups or another standard hydroxy protective group (trimethylsilylethoxymethyl, methoxymethyl, methoxyethoxymethyl, ethoxyethyl, tetrahydrofuranyl and tetrahydropyranyl groups) as well as acetyl, propionyl or pivaloyl groups; for the keto groups, these are preferably ketals (1,3-dioxolans, 1,3-dioxanes, dialkoxyketals) (see T. W. Greene, P. G. M. Wuts "Protective Groups in Organic Synthesis," $2^{nd}$ Edition, John Wiley & Sons, 1991).

By simultaneous or successive cleavage of the hydroxy and keto protective groups and optionally by partial, successive or complete esterification of the free hydroxyl groups, the compound of general formula II is converted into a compound of general formula I.

In the case of the silyl protective groups or the trimethylsilylethoxymethyl group, tetrabutylammonium fluoride, hydrofluoric acid or hydrofluoric acid/pyridine or acidic ion exchanger is used for their cleavage. In the case of the ether groups (methoxymethyl, methoxyethoxymethyl, ethoxyethyl, tetrahydropyranyl ether) and ketals, the latter are cleaved off under catalytic action of acid, for example, p-toluenesulfonic acid, pyridinium-p-toluenesulfonate, acetic acid, hydrochloric acid, phosphoric acid or an acidic ion exchanger. Ester groups, however, are hydrolyzed in a basic medium (sodium carbonate, potassium carbonate, sodium hydroxide, potassium hydroxide in water, ethanol, methanol or mixtures of these solvents).

The esterification of the free hydroxy groups can be carried out, if desired, according to standard processes with the corresponding carboxylic acid chlorides, -bromides or -anhydrides.

The production of the starting compounds for general formula II, in which Q means at least one ethylene group, starts from various starting compounds depending on the ultimately desired substitution pattern in 20-position. For the compounds with natural configuration at C-20, the known CD-fragment III is used as starting material [H. H. Inhoffen, G. Quinkert, S. Schütz, G. Friedrich, E. Tober Chem. Ber. 91, 781–791 (1958)].

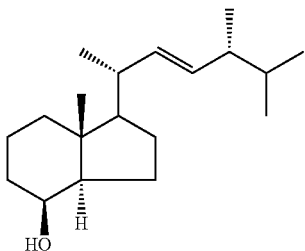

III

By introduction of a protective group, the compound of general formula IV

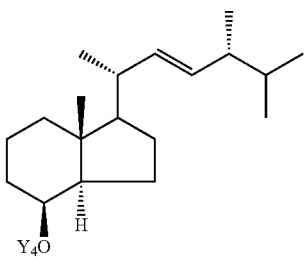

IV is obtained, whereby $Y_4$, i.a., can mean a trialkyl-substituted or a mixed arylalkyl-substituted silyl group or a tetrapyranyl or tetrafuranyl group. Ozonolytic cleavage of the side-chain double bond followed by reductive working-up (e.g., sodium borohydride) yields the compound of general formula V.

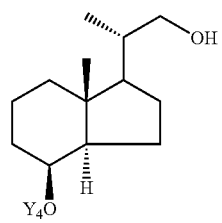

V

The free hydroxy group can now be converted into a leaving group, whereby the compound of general formula VI is produced,

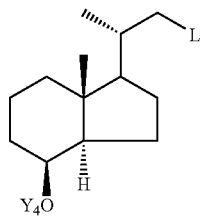

VI for which the following is true:. L stands for any leaving group, especially for a halogen atom (fluorine, chlorine, bromine, iodine) or a mesylate, tosylate, triflate or nonaflate.

Via the propargyl alcohol VII and the conversion into alcohol VIII and oxidation to aldehyde IX described below, the compound of formula VI opens up a new, not yet known access to ketone XIII further described below that represents an important starting material for the synthesis of vitamin D derivatives according to De Luca [H. F. DeLuca et al. Tetrahedron Lett. 32, 7663 (1991); H. F. DeLuca et al. J. Med. Chem. 37, 3730 (1994)].

This invention thus also relates to a process for the production of ketone XIII via the new intermediate stages of Formulas VII, VIII and IX. The synthesis method can be modified in any way desired for another chain length, by a corresponding protected alkinol being used. By way of example, the synthesis method for a compound in which Q means an ethylene group is described below.

Reaction of the compound of general formula VI with a protected propargyl alcohol, which was previously deprotonated with a base (e.g., sodium hydride, potassium hydride, butyllithium, sodium amide), yields the compound of general formula VII

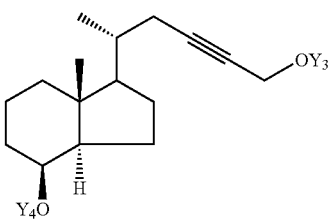

VII for which the following is true: $Y_5$ is to represent a tetrahydropyranyl group, a benzyl group or a used protective group. Hydrogenation of the triple bond and the benzyl ether or optionally followed by cleavage of the tetrahydropyranyl ether under the action of acid (p-toluenesulfonic acid, pyridinium-p-toluenesulfonate, acetic acid, dimethyl aluminum chloride, methylaluminum dichloride, etc.) now produces the compound of general formula VIII, whose free hydroxy group is converted with an oxidizing agent (pyridinium chlorochromate, pyridinium dichromate, Swern conditions, Collins conditions) into the aldehyde of general formula IX.

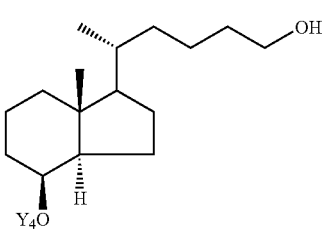

VIII

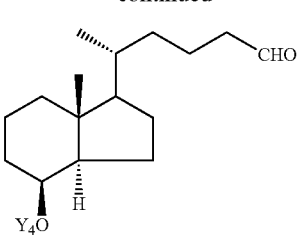

By reaction with any nucleophile Nu, which can be brought to reaction with the aldehyde, such as, e.g., anions, optionally organic radicals that contain oxygen or sulfur atoms, optionally substituted Grignard reagents that are optionally protected on sensitive functional groups, or lithium compounds, which can be produced according to methods that are known in the literature, a compound of general formula Xa is obtained as a mixture of the diastereomeric alcohols.

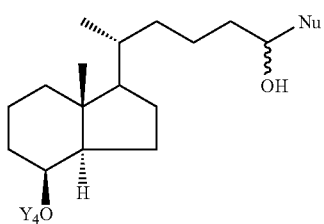

For the synthesis of the compounds according to the invention, the compound of general formula X

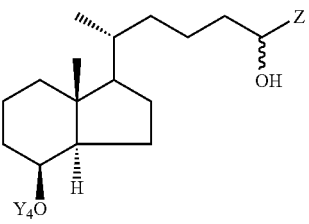

is obtained by reaction with a nucleophilic form of Z with the designation Z', preferably with a metalated aromatic or heteroaromatic compound.

Z can be any of the radicals that are defined for Z, preferably furan, thiophene, oxazole, thiazole, imidazole, pyrazole, pyrrole, benzofuran, benzothiophene, benzoxazole, benzothiazole, benzimidazole, indole or phenyl, whereby the rings can carry one or more substituents at any positions. As substituents, there are fluorine, chlorine, bromine or iodine atoms, one or more hydroxy groups, one or more $COOR_6$ groups, one or more $C_1$–$C_5$ alkyl groups, which in turn can be substituted by one or more fluorine, chlorine, bromine or iodine atoms, $C_1$–$C_6$ alkoxy groups and/or $COOR_6$ groups (and $R_6$ is defined as a $C_1$–$C_6$ alkyl group, a benzyl group or a phenyl group). The aromatic compounds are converted into the metalated derivatives by hydrogen-lithium exchange, orthometalation, halogen-lithium exchange (use of n-butyllithium, s-butyllithium, t-butyllithium, methyllithium) or reaction of halogen compounds with magnesium or zinc. The linkage to the CD-fragment is always carried out in the metalated position with the exception of oxazole rings, which hook on by rearrangement and recycling at the 4-position [G. Boche et al. Chem. Ber./Receuil 130, 1213 (1997)].

Conversion of the free hydroxy group into acetate groupings (R'=Me), propionate groupings (R'=Et) or pivalate groupings (R'=t-Bu) produces compounds of general formula XI, and it is converted into a compound of general formula XII by cleavage of cyclohexanol protective groups $Y_4$. If $Y_4$ means a silyl group, its cleavage can be carried out, e.g., with use of tetrabutylammonium fluoride, hydrogen fluoride, hydrogen fluoride/pyridine complex; however, if $Y_4$ means a tetrahydropyranyl group or a tetrahydrofuranyl group, its cleavage can be completed under acidic conditions. Subsequent oxidation of the free hydroxy group with an oxidizing agent (pyridinium chlorochromate, pyridinium dichromate, Swern conditions, Collins conditions) yields the compound of general formula XIII.

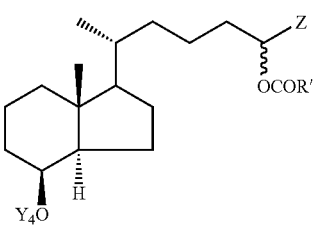

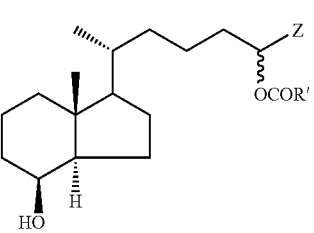

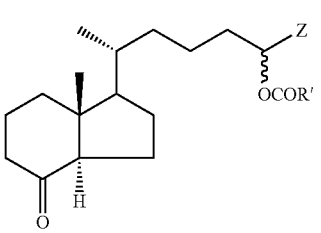

Reaction of the ketone of general formula XIII with one of the known phosphine oxides XIV, XV or XVI [XIV: M. R. Uskokovic et al. Tetrahedron Lett. 33, 7701 (1992), A. Mourino et al. Tetrahedron Lett. 38, 4713 (1997), XV: H. F. DeLuca et al. Tetrahedron Lett. 32, 7663 (1991), XVI: H. F. DeLuca et al. J. Med. Chem. 37, 3730 (1994)],

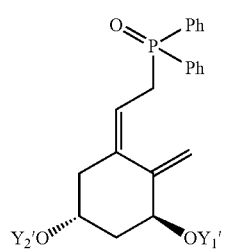

-continued

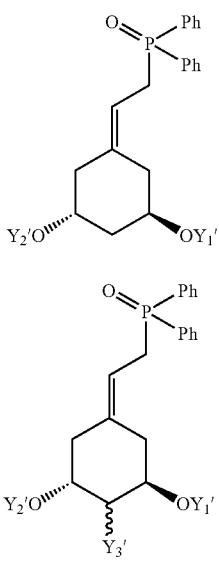

XV

XVI whereby Y'₁ and Y'₂ represent alkyl- or mixed arylalkyl-substituted silyl groups (preferably tert-butyldimethylsilyl, tert-butyldiphenylsilyl, trimethylsilyl, triethylsilyl and triisopropylsilyl groups) and Y'₃ means the corresponding silyloxy grouping, yields the vitamin D systems of general formulas XVII, XVIII and XIX.

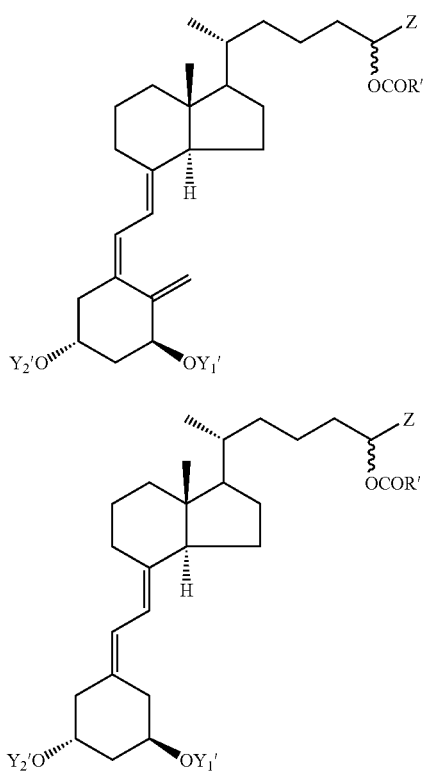

XVII

XVIII

-continued

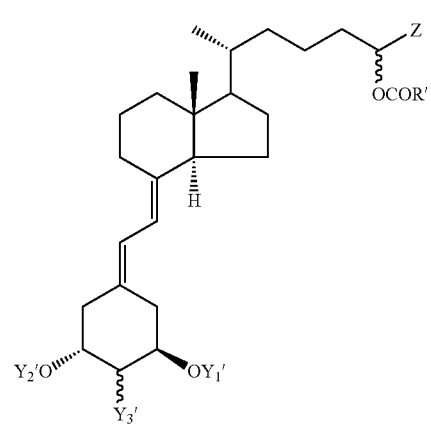

XIX

The compounds of general formulas XVII, XVIII and XIX represent special cases of general formula II and are converted into compounds of general formula I as described above.

In particular, the hydroxy group in position C-24 can be released and converted with an oxidizing agent (e.g., pyridinium chlorochromate, pyridinium dichromate, Collins reagent, Swern conditions, manganese dioxide) into the corresponding ketone, which likewise represents a special case of general formula II. The C-24 alcohols or the C-24 ketone can be converted into halides or dihalides under known conditions. The possibility of the reductive removal of the hydroxy, keto or halogen units also exists.

Any manipulations of the functional groups in the side chain can also be completed in earlier stages.

For the production of compounds of general formula II with altered substitution patterns at C-20, the alcohol of general formula V is oxidized to the aldehyde of general formula XX with an oxidizing agent (e.g., pyridinium chlorochromate, pyridinium dichromate, Collins reagent, Swern conditions, Dess-Martin conditions). The latter can be converted as described [DE 42 20 757, 20-epi: M. J. Calverley Bioorg. Med. Chem. Lett. 3, 1845 (1993)] into compounds of general formula XXI, in which R₃ and R₄ have the already-mentioned meanings. Then, the reduction with a reducing agent (e.g., sodium borohydride, lithium aluminum hydride, diisobutylaluminum hydride) is carried out to alcohol of general formula XXII, which is further reacted as described above.

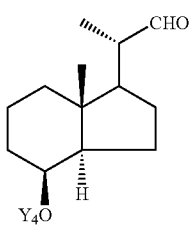

XX

XXI

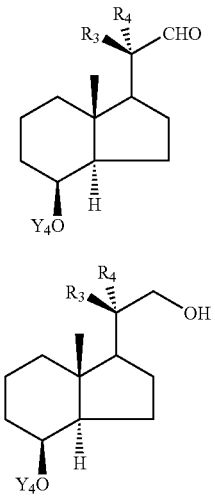

XXII

For compounds of general formula II, the following is true: Q is a methylene group, and a start is made from known vitamin D-aldehyde XXIII, which can be modified at position 20 as described above (DE 196 19 036). By way of example, the further reaction of aldehyde with natural configuration at C-20 is described.

XXIII

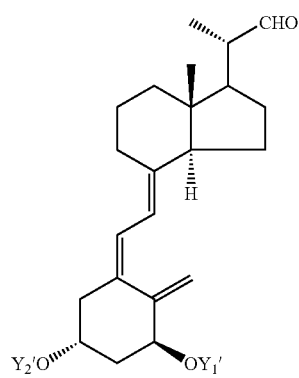

With a reducing agent (e.g., sodium borohydride, lithium aluminum hydride, isobutylaluminum hydride), the alcohol of general formula XXIV, which is converted into a leaving group as described above, is obtained, whereby the compound of general formula XXV accumulates.

XXIV

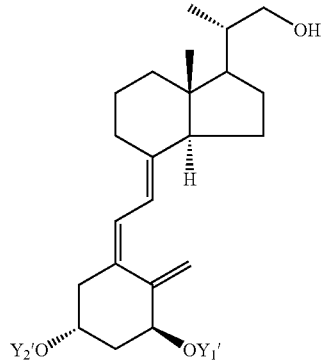

XXV

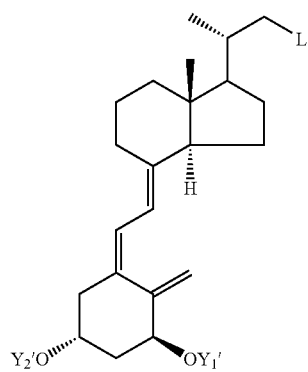

Reaction of the compounds of general formula XXV with the acetonitrile that is deprotonated by a base (e.g., lithium diisopropylamide, sodium hexamethyldisilazide, lithium hexamethyl disilazide, potassium hexamethyl disilazide) produces a compound of general formula XXVI, which is converted by reduction with a reducing agent (e.g., diisobutylaluminium hydride) into a compound of general formula XXVII.

XXVI

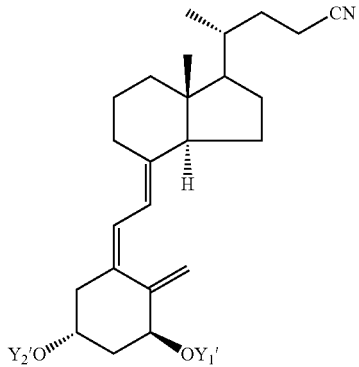

XXVII

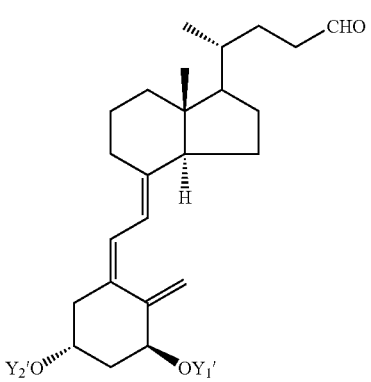

By reaction with the nucleophile of a carbocyclic or heterocyclic compound, preferably a metalated aromatic or heteroaromatic compound, compounds of general formula XXVIII

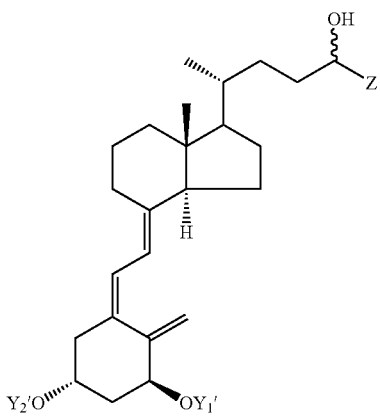

XXVIII as already shown above, which are to be considered as a special case of general formula II, are obtained and are to be converted into compounds of general formula I as described. In particular, the hydroxy group in position C-24 can be converted into the corresponding ketone with an oxidizing agent (e.g., pyridinium chlorochromate, pyridinium dichromate, Collins reagent, Swern conditions, manganese dioxide), which likewise represents a special case of general formula II. The C-24 alcohols or the C-24 ketone can be converted into halides or dihalides under known conditions. The possibility also exists of the reductive removal of hydroxy, keto or halogen units.

If compounds of general formula I are to be generated, for which $Y_3$ is a halogen atom (e.g., fluorine, chlorine or bromine atom), an A-component of general formula XXX, whereby $Y_3$ is to have the above-mentioned meaning, must by synthesized from the cyclohexane derivative XXIX that is known from the literature [J.-L. Montchamp, J. W. Frost J. Am. Chem. Soc. 113, 6296 (1991)] by Hanessian reaction.

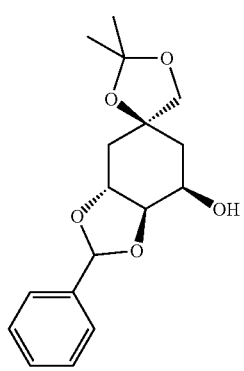

XXIX

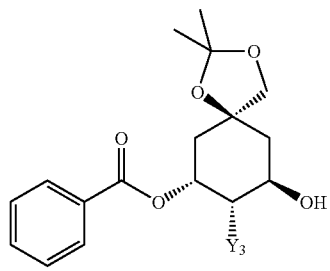

XXX

Introduction of a protective group for the free hydroxy group produces the compound of general formula XXXI, which is converted in the acid medium as usual into diol XXXII and by subsequent diol cleavage (sodium periodate, periodic acid) into ketone XXXIII, whereby the definitions for $Y'_1$ and $Y_3$ were already indicated.

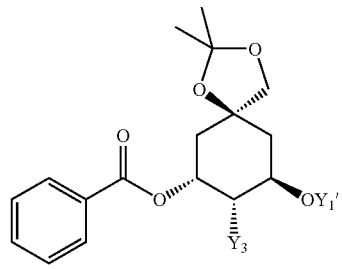

XXXI

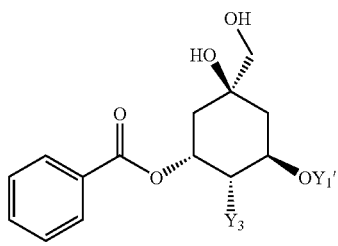

XXXII

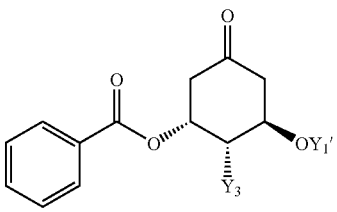

XXXIII

In building the vitamin D system, a new approach is used for $Y_3$=halogen, which can also be used, however, for all possible substituents for $Y_3$ (also $Y_3$=a hydrogen atom), as well as for other substitution patterns in the A-ring (e.g., instead of $OY_1$ in 1-position, halogen, $(CH_2)_n$—OH or $(CH_2)_n$—O(CO)$R_5$ with $R_5$=aliphatic $C_1$-$C_{12}$ alkyl radical, which optionally is interrupted by 1–2 oxygen atoms, 1–2 sulfur atoms and/or 1–2 NH groups and/or optionally is substituted by 1–2 hydroxy groups, 1–2 amino groups, 1–2 SH groups, 1–2 COOH groups and/or 1–2 phenyl groups, with n=0–4 or an aromatic radical with 5 to 12 C atoms), and also any side chains in 17-position with optionally protected existing hydroxy groups and/or keto groups.

The reactions at the ketone of general formula XIII are described here by way of example but are also valid for other side-chain variants:

By Peterson olefination (reaction with trimethylsilylacetic ester in the presence of a base, such as, e.g., n-butyllithium or lithium diisopropylamide), the compound of general formula XXXIV, whose ester group is converted into the alcohol of general formula XXXV by reduction with a reducing agent (e.g., diisobutylaluminum hydride, lithium aluminum hydride) is obtained from ketone XIII. The conversion of the hydroxy group into a diphenylphosphine oxide derivative of general formula XXXVI is carried out according to standard conditions via an allyl halide (chloride, bromide) or an intermediate tosylate or mesylate.

XXXIV

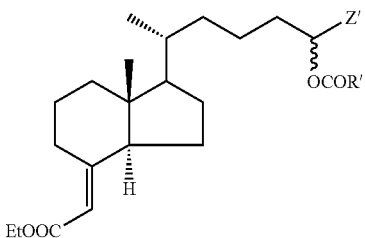

XXXV

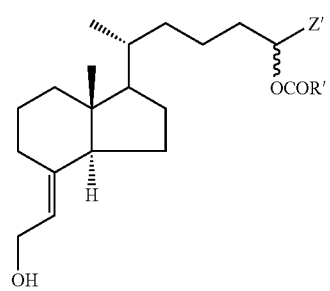

XXXVI

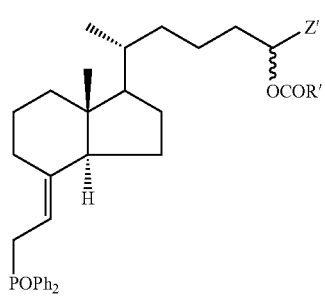

The linkage with the ketone of general formula XXXIII ultimately produces the vitamin D system of general formula II with the already mentioned definitions for $Y_3$. The conversion into a compound of general formula I is carried out as described previously by cleavage of the protective groups.

The subject of this invention is thus also a new process for the production of vitamin D derivatives of general formula IIa, IIa

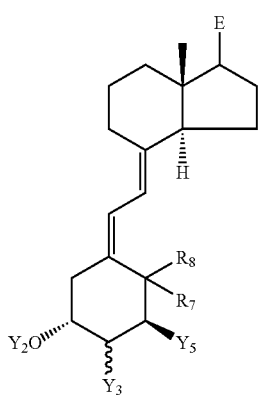

in which.

E means any side chain, $R_7$, $R_8$, independently of one another, mean a hydrogen atom, a methyl group, or together an exocyclic methylene group or a cyclopropyl ring, $Y_2$ means a hydrogen atom or a group —(CO)$R_5$, $Y_3$ means a hydrogen atom, a hydroxy group, a halogen atom, a group —O(CO)$R_5$ or an OR$_5$ group, whereby $R_5$ stands for an aliphatic $C_1$–$C_1$ alkyl radical, which optionally is interrupted by 1–2 oxygen atoms, 1–2 sulfur atoms and/or 1–2 NH groups and/or optionally is substituted by 1–2 hydroxy groups, 1–2 amino groups, 1–2 SH groups, 1–2 COOH groups and/or 1–2 phenyl groups, or for an aromatic radical with 5 to 12 C atoms, $Y_5$ means a fluorine atom, a $(CH_2)_n$—OH group or a $(CH_2)_n$—O(CO)$R_5$ group, whereby n=0 to 4, and optionally present hydroxy groups are optionally present in protected form, which is characterized in that a ketone of general formula XIIIc XIIIc

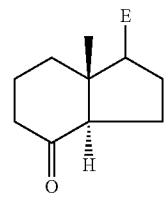

in which

E means any side chain and optionally existing keto groups and/or hydroxy groups are present in protected form is converted by reaction with trimethylsilylacetic ester in the presence of a base, such as, e.g., n-butyllithium or lithium aluminum hydride or with a suitable Wittig reagent in an aprotic solvent such as toluene, tetrahydrofuran, diethyl ether or dioxane into a compound of general formula XXXIVc XXXIVc

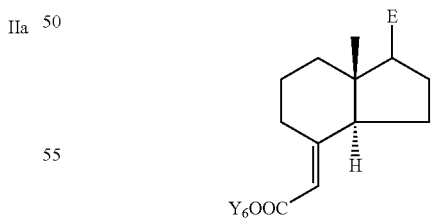

in which $Y_6$ means a $C_1$–$C_6$ alkyl group, a benzyl group, or a phenyl group, the ester group is converted by reaction with a reducing agent such as Dibah, lithium aluminum hydride, diborane or RedAl in hexane, toluene, tetrahydrofuran, diethyl ether or dioxane into the allyl alcohol of general formula XXXVc

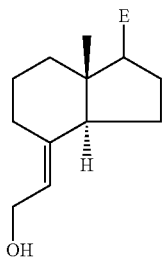

XXXVc the allyl alcohol is converted in a way that is known in the art into a compound of general formula XXXVc XXXVc

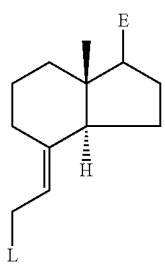

in which
L means any leaving group (halogen, mesylate, tosylate, triflate, nonaflate), which is isolated or optionally produced in situ and immediately further reacted to a Wittig reagent of general formula XXXVIc, XXXVIc

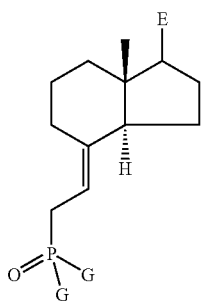

in which
G means a $C_1$–$C_{10}$ alkyl group, a $C_1$–$C_{10}$ alkoxy group, a phenyl radical or a phenoxy radical, which then is reacted under known conditions with a ketone of general formula XXXIIIc XXXIIIc

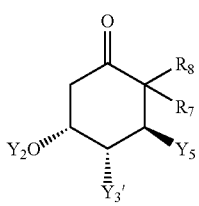

in which
$Y'_3$ means a hydrogen atom, a halogen atom or a protected hydroxy group, a group —O(CO)$R_5$ or an OR$_5$ group, and $Y_5$, $R_7$ and $R_8$ have the above-indicated meaning, and if desired, protective groups are cleaved.

The compounds of general formula IIa can be converted into the desired vitamin D derivatives-by cleavage of the protective groups as described above.

Especially suitable is the process according to the invention for the production of vitamin D derivatives, in which $Y_3$ means a halogen atom, but it is not limited thereto.

The additives "a" in the designation of the formulas (e.g., XXXIVa) is to make clear that the meanings of the radicals are basically the same as in the formula without additive "a", but sensitive groups are present in protected form.

An alternative method to the synthesis of compounds of general formula II, for which $X'_1$ and $X'_2$ mean hydrogen atoms and Q represents an ethylene group, starts from alcohol of general formula VIII, whose hydroxy group is converted into a leaving group (e.g., chloride, bromide, iodide, tosylate, mesylate) and is reacted with metalated aromatic or heteroaromatic compounds, whereby compounds of general formula XXXVII accumulate,

XXXVII

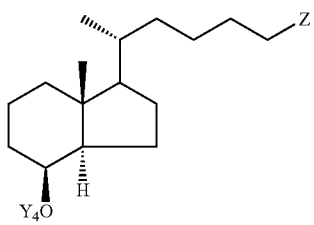

and whose further reaction can be carried out analogously to the above-described compounds.

The examples below are used for a more detailed explanation of the invention.

EXAMPLES

Synthesis of the Starting Compounds (CD-Aldehyde):

1. [1R-[1α[1R*,4S*-(E),3aβ,4α,7aα]]-Octahydro-7a-methyl-4-[(triethylsilyl)oxy]-1-(1,4,5-trimethyl-2-hexenyl)-1H-indene 2

12.95 g of [1R-[1α[1R*,4S*-(E)],3aβ,4α,7aα]]-octahydro-7a-methyl-1-(1,4,5-trimethyl-2-hexenyl)-1H-inden-4-ol 1 is introduced into 220 ml of dimethylformamide [H. H. Inhoffen et al. Chem. Ber. 91, 781 (1958)], 5.33 g of imidazole and 10.78 ml of chlorotriethylsilane are added, and it is stirred for 24 hours at room temperature. It is quenched with sodium chloride solution, extracted with ethyl acetate, the organic phase is washed with sodium chloride solution and dried on sodium sulfate. After the solvent is removed, the residue is purified by chromatography on silica gel with ethyl acetate/hexane, whereby 14.6 g of title compound 2 is obtained as a colorless oil.

$^1$H-NMR (CDCl$_3$): δ=0.58 ppm (q, 6H); 0.82 (d, 3H); 0.84 (d, 3H); 0.93 (t, 9H); 0.96 (d, 3H); 0.97 (s, 3H); 0.98 (d, 3H); 4.05 (m, 1H); 5.19 (m, 2H)

2. [1R-[1α(S*),3aβ,4α,7aα]]-2-[Octahydro-7a-methyl-4-[(triethylsilyl)oxy]-1H-inden-1-yl]-1-propanol 3

14.6 g of silylether 2 is dissolved in 300 ml of dichloromethane and 150 ml of methanol, 14.8 ml of pyridine is added, and it is cooled to −78° C. At this temperature, ozone, which has been produced by an ozone generator, is introduced until the solution is blue-colored. Excess ozone is expelled by oxygen passing through it, and then it is mixed with 1.61 g of sodium borohydride. It is heated to room temperature, and then the reaction mixture is poured into dichloromethane. The organic phase is washed with sodium chloride solution, dried on sodium sulfate and concentrated by evaporation. The residue is chromatographed by chromatography on silica gel with ethyl acetate/hexane, whereby 10.1 g of title compound 3 is obtained as a colorless oil.

$^1$H-NMR (CDCl$_3$): δ=0.57 ppm (q, 6H); 0.92 (s, 3H); 0.96 (t, 9H); 1.02 (d, 3H); 3.38 (dd, 1H); 3.63 (d, 1H); 4.05 (m, 1H)

3. [1R-[1α(S*),3aβ,4α,7aα]]-2-[Octahydro-7a-methyl-4-[(triethylsilyl)oxy]-1H-inden-1-yl]propyl-(4-methylbenzenesulfonate) 4

9.1 g of alcohol 3 is dissolved in 135 ml of pyridine, cooled to 0° C., and then 7.8 g of p-toluenesulfonyl chloride is added. It is stirred overnight at 0° C. and then carefully quenched with sodium bicarbonate solution. It is extracted with ethyl acetate, the organic phase is washed with sodium chloride solution, dried on sodium sulfate, and the solvent is removed in a vacuum. The residue is chromatographed on silica gel with ethyl acetate/hexane, whereby 13.3 g of title compound 4 is obtained as a colorless oil.

$^1$H-NMR (CDCl$_3$): δ=0.56 ppm (q, 6H); 0.87 (s, 3H); 0.96 (t, 9H); 0.97 (d, 3H); 2.47 (s, 3H); 3.80 (dd, 1H); 3.97 (d, 1H); 4.01 (m, 1H); 7.35 (d, 2H); 7.80 (d, 2H)

4. [1R-[1α(R*),3aβ,4α,7aα]]-Octahydro-7a-methyl-1-[5-[(tetrahydro-2H-pyran-2-yl)oxy]-1-methyl-3-pentinyl-4-[(triethylsilyl)oxy]-1H-indene 5

15.4 g of propargyl-THP-ether is introduced into 350 ml of dioxane, and 43.8 ml of n-butyllithium (2.5 M in hexane) is carefully added in drops at 10–15° C. After one hour, 13.3 g of tosylate 4 in 100 ml of dioxane is added in drops, and it is heated to boiling for 48 hours. It is then quenched with sodium chloride solution, extracted with ethyl acetate, the organic phase is washed with sodium chloride solution and dried on sodium sulfate. After the solvent is removed, the residue is chromatographed on silica gel with ethyl acetate/hexane, whereby 12.1 g of title compound 5 is obtained as a colorless oil.

$^1$H-NMR (CDCl$_3$): δ=0.57 ppm (q, 6H); 0.92 (s, 3H); 0.96 (t, 9H); 1.06 (d, 3H); 3.56 (m, 1H); 3.88 (m, 1H); 4.04 (m, 1H); 4.29 (d, 2H); 4.83 (m, 1H)

5. [1R-[1α(R*),3aβ,4α,7aα]]-Octahydro-7a-methyl-1-5-[(tetrahydro-2H-pyran-2-yl)oxy]-1-methylpentyl-4-[(triethylsilyl)oxy]-1H-indene 6

12.6 g of alkine 5 is dissolved in 250 ml of ethyl acetate, 2.2 g of palladium/carbon (10%) and 5.06 g of sodium bicarbonate are added and hydrogenated under normal pressure in a hydrogenating apparatus. When hydrogen is no longer taken up, the batch is filtered on Celite and concentrated by evaporation. The residue is chromatographed on silica gel with ethyl acetate/hexane, whereby 9.9 g of title compound 6 is obtained as a colorless oil.

$^1$H-NMR (CDCl$_3$): δ=0.56 ppm (q, 6H); 0.91 (s, 3H); 0.95 (t, 9H); 0.97 (d, 3H); 3.38 (m, 1H); 3.51 (m, 1H); 3.70 (m, 1H); 3.88 (m, 1H); 4.02 (m, 1H); 4.59 (m, 1H)

6. [1R-[1α(R*),3aβ,4α,7aα]]-5-[(Octahydro-7a-methyl-4-[(triethylsilyl)oxy]-1H-inden-1-yl]-1-hexanol 7

11.4 g of THP-ether 6 is introduced into 500 ml of dichloromethane, and 50 ml of dimethylaluminum chloride solution is added in drops. After 2 hours at room temperature, it is quenched with isopropanol/water (15:85), toluene is added, and it is stirred overnight. Then, it is suctioned off on Celite and concentrated by evaporation. The residue is chromatographed on silica gel with ethyl acetate/hexane, whereby 6.2 g of title compound 7 is obtained as a colorless oil.

$^1$H-NMR (CDCl$_3$): δ=0.56 ppm (q, 6H); 0.90 (s, 3H); 0.95 (t, 9H); 0.96 (d, 3H); 3.64 (m, 2H); 4.02 (m, 1H)

7. [1R-[1α(R*),3aβ,4α,7aα]]-5-[Octahydro-7a-methyl-4-[(triethylsilyl)oxy]-1H-inden-1-yl]hexanal 8

8.0 g of alcohol 7 is dissolved in 300 ml of dichloromethane, and then 6.5 g of pyridinium chlorochromate is added. It is stirred for 2 hours at room temperature. Then, diethyl ether is added, filtered on Celite and concentrated by evaporation. The residue is chromatographed on silica gel with ethyl acetate/hexane, whereby 6.2 g of title compound 8 is obtained as a colorless oil.

$^1$H-NMR (CDCl$_3$): δ=0.57 ppm (q, 6H); 0.91 (s, 3H); 0.95 (t, 9H); 0.96 (d, 3H); 4.02 (m, 1H); 9.75 (t, 1H)

Example 1

(7E)-(1R,3R,24aR)-24a-(Oxazol-4-yl)-24a-homo-19-nor-9,10-secochola-5,7-diene-1,3,24a-triol 16a and (7E)-(1R,3R,24aS)-24a-(oxazol-4-yl)-24a-homo-19-nor-9,10-secochola-5,7-diene-1,3,24a-triol 16b 8. 939 mg of oxazole is introduced into 20 ml of tetrahydrofuran and cooled to −78° C. Then, 5.44 ml of n-butyllithium (2.5 M in hexane) is added in drops, stirred for 20 more minutes, and then 500 mg of aldehyde 8 in 5 ml of tetrahydrofuran is added. It is stirred overnight, whereby the mixture is heated to room temperature and then quenched with sodium chloride solution. It is extracted with ethyl acetate, the organic phase is washed with sodium chloride solution, dried on sodium sulfate, and the solvent is removed. The residue is chromatographed on silica gel with ethyl acetate/hexane, whereby 234 mg of [1R-[1α(1R*),3aβ,4α,7aα]]-α-[4-[octahydro-7a-methyl-4-[(triethylsilyl)oxy]-1H-inden-1-yl]-pentyl]oxazole-4-methanol 9 is obtained as a colorless oil.

$^1$H-NMR (CDCl$_3$): δ=0.57 ppm (q, 6H); 0.86 (d, 3H); 0.92 (s, 3H); 0.99 (t, 9H); 4.02 (m, 1H); 4.70 (m, 1H); 7.60 (s, 1H); 7.90 (s, 1H)

9. 361 mg of alcohol 9 is introduced into 8 ml of dichloromethane, 0.17 ml of triethylamine, 0.12 ml of acetic acid anhydride and a spatula-tip full of dimethylaminopyridine are added, and it is stirred overnight at room temperature. Then, sodium chloride solution is added, extracted with ethyl acetate, the organic phase is washed with sodium bicarbonate solution and sodium chloride solution, dried on sodium sulfate and concentrated by evaporation. The residue is chromatographed on silica gel with ethyl acetate/hexane, whereby 296 mg of [1R-[1α(1R*),3aβ,4α,7aα]]-5-[octahydro-7a-methyl-4-[(triethylsilyl)oxy]-1H-inden-1-yl]-1-(oxazol-4-yl)hexyl-acetate 10 is obtained as a colorless oil.

$^1$H-NMR (CDCl$_3$): δ=0.57 ppm (q, 6H); 0.86/0.87 (d, 3H); 0.90 (s, 3H); 0.98 (t, 9H); 2.09 (s, 3H); 4.02 (m, 1H); 5.80 (t, 1H); 7.62 (s, 1H); 7.86 (s, 1H)

10. 281 mg of acetate 10 is introduced into 10 ml of tetrahydrofuran, 1 ml of hydrogen fluoride-pyridine complex is added, and it is stirred overnight at room temperature. Then, it is quenched with sodium bicarbonate solution, extracted with ethyl acetate, the organic phase is washed with sodium chloride solution, dried on sodium sulfate, and the solvent is removed. The residue is chromatographed on silica gel with ethyl acetate/hexane, whereby 193 mg of [1R-[1α(1R*),3aβ,4α,7aα]]-1-[5-(acetyloxy)-1-methyl-5-(oxazol-4-yl)pentyl]octahydro-7a-methyl-1H-inden-4-ol 11 is obtained as a colorless oil.

$^1$H-NMR (CDCl$_3$): δ=0.88/0.89 ppm (d, 3H); 0.91 (s, 3H); 2.09 (s, 3H); 4.07 (m, 1H); 5.80 (t, 1H); 7.61 (s, 1H); 7.85 (s, 1H)

11. 193 mg of alcohol 11 is introduced into 8 ml of dichloromethane, 160 mg of pyridinium chlorochromate is added, and it is stirred for 1 hour at room temperature. Then, it is diluted with diethyl ether, filtered on Celite, and the solvent is removed. The residue is chromatographed on silica gel with ethyl acetate/hexane, whereby 160 mg of [1R-[1α(1R*),3aβ,7aα]]-1-[5-(acetyloxy)-1-methyl-5-(oxazol-4-yl)pentyl]octahydro-7a-methyl-4H-inden-4-on 12 is obtained as a colorless oil.

$^1$H-NMR (CDCl$_3$): δ=0.61 ppm (s, 3H); 0.91/0.92 (d, 3H); 2.10 (s, 3H); 4.07 (m, 1H); 5.80 (t, 1H); 7.62 (s, 1H); 7.85 (s, 1H)

12. 461 mg of [2-[(3R-trans)-3,5-bis[[(1,1-dimethylethyl)dimethyl-silyl]oxy]cyclohexylidene]ethyl]-diphenylphosphine oxide 13 [H. F. DeLuca et al. Tetrahedron Lett. 32, 7663 (1991), A. Mourino et al. Tetrahedron Lett. 38, 4713 (1997)] is introduced into 8 ml of tetrahydrofuran, and it is cooled to −78° C. At this temperature, 0.39 ml of n-butyllithium solution (2.5 M in hexane) is added, and it is stirred for 10 minutes at −30° C. Then, 146 mg of ketone 12 in 4 ml of tetrahydrofuran is added in drops, and it is stirred for one more hour. It is quenched with sodium chloride solution, extracted with ethyl acetate, the organic phase is washed with sodium chloride solution, dried on sodium sulfate and concentrated by evaporation. The residue is chromatographed on silica gel with ethyl acetate/hexane, whereby 180 mg of (7E)-(1R,3R)-24a-(acetyloxy)-1,3-bis[[(1,1-dimethylethyl)dimethylsilyl]oxy]-24a-(oxazol-4-yl)-24a-homo-19-nor-9,10-secochola-5,7-diene 14 is obtained as a colorless foam.

$^1$H-NMR (CDCl$_3$): δ=0.06 ppm (s, 12H); 0.52 (s, 3H); 0.89 (s, 18H); 0.90 (d, 3H); 2.09 (s, 3H); 4.08 (m, 2H); 5.80 (t, 1H); 5.81 (d, 1H); 6.18 (d, 1H); 7.61 (s, 1H); 7.87 (s, 1H)

13. 180 mg of acetate 14 is introduced into 8 ml of methanol, 140 mg of potassium carbonate is added, and it is stirred for 1 hour at room temperature. Then, it is mixed with sodium chloride solution, extracted with ethyl acetate, the organic phase is washed with sodium chloride solution, dried on sodium sulfate, and the solvent is removed. The residue is chromatographed on silica gel with ethyl acetate/hexane, whereby 144 mg of (7E)-(1R,3R)-1,3-bis[[(1,1-dimethylethyl)dimethylsilyl]oxy]-24a-(oxazol-4-yl)-24a-homo-19-nor-9,10-secochola-5,7-dien-24a-ol 15 is obtained as a colorless foam.

$^1$H-NMR (CD$_2$Cl$_2$): δ=0.06 ppm (s, 12H); 0.52 (s, 3H); 0.84 (s, 18H); 0.91/0.92 (d, 3H); 4.07 (m, 2H); 4.62 (m, 1H); 5.80 (d, 1H); 6.14 (d, 1H); 7.55 (s, 1H); 7.82 (s, 1H)

14. 144 mg of alcohol 15 is introduced into 10 ml of tetrahydrofuran, 467 mg of tetrabutylammonium fluoride (hydrate) is added, and it is stirred for 2 days at room temperature. Then, sodium bicarbonate solution is added, extracted with ethyl acetate, the organic phase is washed with sodium chloride solution, dried on sodium sulfate and concentrated by evaporation. The residue is chromatographed on silica gel with ethyl acetate/hexane, and then the diastereomers (in terms of C-24a) are separated via HPLC, whereby 25 mg of title compound 16a and 34 mg of title compound 16b accumulate as colorless foams.

$^1$H-NMR (CD$_2$Cl$_2$): 16a: δ=0.52 ppm (s, 3H); 0.89 (d, 3H); 3.98 (m, 1H); 4.03 (m, 1H); 4.62 (m, 1H); 5.82 (d, 1H); 6.28 (d, 1H); 7.57 (s, 1H); 7.84 (s, 1H)

16b: δ=0.52 ppm (s, 3H); 0.90 (d, 3H); 3.98 (m, 1H); 4.03 (m, 1H); 4.62 (m, 1H); 5.82 (d, 1H); 6.28 (d, 1H); 7.57 (s, 1H); 7.83 (s, 1H)

Example 2

(5Z,7E)-(1S,3R,24aR)-24a-(Oxazol-4-yl)-24a-homo-9,10-secochola-5,7,10(19)-triene-1,3,24a-triol 20a and (5Z,7E)-(1S,3R,24aS)-24a-(oxazol-4-yl)-24a-homo-9,10-secochola-5,7,10(19)-triene-1,3,24a-triol 20b 15. 257 mg of (2-[[3S-(1Z,3α,5β)]-0.3,5-bis[[(1,1-dimethylethyl)dimethylsilyl]oxy]-2-methylenecyclohexylidene]ethyl]-diphenylphosphine oxide 17 [M. R. Uskokovic et al. Tetrahedron Let. 33, 7701 (1992)) is introduced into 6 ml of tetrahydrofuran, and it is cooled to −78° C. At this temperature, 0.21 ml of n-butyllithium solution (2.5 M in hexane) is added, and it is stirred for 10 minutes at −30° C. Then, 80 mg of ketone 12 in 4 ml of tetrahydrofuran is added in drops and stirred for one more hour. It is quenched with sodium chloride solution, extracted with ethyl acetate, the organic phase is washed with sodium chloride solution, dried on sodium sulfate and concentrated by evaporation. The residue is chromatographed on silica gel with ethyl acetate/hexane, whereby 140 mg of (5Z,7E)-(1S,3R)-24a-(acetyloxy)-1,3-bis[[(1,1-dimethylethyl)dimethylsilyl]oxy]-24a-(oxazol-4-yl)-24a-homo-9,10-secochola-5,7,10(19)-triene 18 is obtained as a colorless foam.

$^1$H-NMR (CDCl$_3$): δ=0.06 ppm (s, 12H); 0.52 (s, 3H); 0.90 (s, 18H); 0.90 (d, 3H); 2.09 (s, 3H); 4.19 (m, 1H); 4.38 (m, 1H); 4.88 (s, 1H); 5.19 (s, 1H); 5.81 (t, 1H); 6.02 (d, 1H); 6.23 (d, 1H); 7.62 (s, 1H); 7.87 (s, 1H)

16. 140 mg of acetate 18 is treated analogously to 13., and 120 mg of (5Z,7E)-(1S,3R)-1,3-bis[[(1,1-dimethylethyl)dimethylsilyl]-oxy]-24a-(oxazol-4-yl)-24a-homo-9,10-secochola-5,7,10(19)-trien-24a-ol 19 is obtained as a colorless foam.

$^1$H-NMR (CDCl$_3$): δ=0.07 ppm (s, 12H); 0.52 (s, 3H); 0.89 (s, 18H); 0.90 (d, 3H); 4.19 (m, 1H); 4.38 (m, 1H); 4.87 (s, 1H); 5.20 (s, 1H); 5.81 (t, 1H); 6.02 (d, 1H); 6.25 (d, 1H); 7.60 (s, 1H); 7.88 (s, 1H)

17. 120 mg of alcohol 19 is treated analogously to 14., and after the diastereomers (in terms of C-24a) are separated by HPLC, 14 mg of title compound 20a and 18 mg of title compound 20b are obtained as colorless foams.

$^1$H-NMR (CD$_2$Cl$_2$): 20a: δ=0.53 ppm (s, 3H); 0.91 (d, 3H); 4.15 (m, 1H); 4.36 (m, 1H); 4.63 (m, 1H); 4.94 (s, 1H); 5.26 (s, 1H); 6.01 (d, 1H); 6.35 (d, 1H); 7.56 (s, 1H); 7.84 (s, 1H)

20b: δ=0.53 ppm (s, 3H); 0.90 (d, 3H); 4.15 (m, 1H); 4.36 (m, 1H); 4.63 (m, 1H); 4.93 (s, 1H); 5.26 (s, 1H); 6.01 (d, 1H); 6.35 (d, 1H); 7.56 (s, 1H); 7.85 (s, 1H)

Example 3

(7E)-(1R,3R,24aR)-24a-(Thiazol-2-yl)-24a-homo-19-nor-9,10-secochola-5,7-diene-1,3,24a-triol 27a and (7E)-(1R,3R,24aS)-24a-(thiazol-2-yl)-24a-homo-19-nor-9,10-secochola-5,7-diene-1,3,24a-triol 27b 18. 3.1 ml of 2-bromothiazole is introduced into 40 ml of tetrahydrofuran, and 13.8 ml of n-butyllithium solution (2.5 M in hexane) is added at −78° C. After 30 minutes at this temperature, 2.52 g of aldehyde 8 in 10 ml of tetrahydrofuran is added in drops, and it is stirred for one more hour. Then, it is quenched with sodium chloride solution, extracted with ethyl acetate, the organic phase is washed with sodium chloride solution and dried on sodium sulfate. The solvent is removed, and the residue is chromatographed on silica gel with ethyl acetate/hexane, whereby 2.6 g of [1R-[1α(1R*),3aβ,4α,7aα]]-α-[4-[octahydro-7a-methyl-4-[(triethylsilyl)oxy]-1H-inden-1-yl]pentyl]thiazole-2-methanol 21 is obtained as a colorless oil.

$^1$H-NMR (CDCl$_3$): δ=0.57 ppm (q, 6H); 0.88 (d, 3H); 0.91 (s, 3H); 0.97 (t, 9H); 4.02 (m, 1H); 5.01 (m, 1H); 7.30 (d, 1H); 7.71 (d, 1H)

19. 948 mg of alcohol 21 is treated analogously to 9., and 824 mg of [1R-[1α(1R*),3aβ,4α,7aα]]-5-[octahydro-7a-methyl-4-[((triethylsilyl)oxy]-1H-inden-1-yl]-1-(thiazol-2-yl)hexyl-acetate 22 is obtained as a colorless oil.

$^1$H-NMR (CDCl$_3$): δ=0.56 ppm (q, 6H); 0.87/0.88 (d, 3H); 0.90 (s, 3H); 0.96 (t, 9H); 2.14 (s, 3H); 4.02 (m, 1H); 6.10 (t, 1H); 7.31 (d, 1H); 7.78 (d, 1H)

20. 824 mg of acetate 22 is treated analogously to 10., and 583 mg of [1R-[1α(1R*),3aβ,4α,7aα]]-1-[5-(acetyloxy)-1-methyl-5-(thiazol-2-yl)pentyl]octahydro-7a-methyl-1H-inden-4-ol 23 is obtained as a-colorless oil.

$^1$H-NMR (CDCl$_3$): δ=0.88/0.89 ppm (d, 3H); 0.93 (s, 3H); 2.18 (s, 3H); 4.07 (m, 1H); 6.10 (t, 1H); 7.31 (d, 1H); 7.78 (d, 1H)

21. 583 mg of alcohol 23 is treated analogously to 11., and 514 mg of [1R-[1α(1R*),3aβ,7aα]]-1-(5-(acetyloxy)-1-methyl-5-(thiazol-2-yl)pentyl]octahydro-7a-methyl-4H-inden-4-one 24 is obtained as a colorless oil.

$^1$H-NMR (CDCl$_3$): δ=0.56 ppm (s, 3H); 0.91/0.92 (d, 3H); 2.12 (s, 3H); 6.10 (t, 1H); 7.31 (d, 1H); 7.78 (d, 1H)

22. 1.39 g of phosphine oxide 13, which was deprotonated with 1.16 ml of n-butyllithium solution (2.5 M in hexane), is reacted with 460 mg of ketone 24 analogously to 12., and 672 mg of (7E)-(1R,3R)-24a-(acetyloxy)-1,3-bis[[(1,1-dimethylethyl)dimethylsilyl]oxy]-24a-(thiazol-2-yl)-24a-homo-19-nor-9,10-secochola-5,7-diene 25 is obtained as a colorless foam.

$^1$H-NMR (CDCl$_3$): δ=0.07 ppm (s, 12H); 0.53 (s, 3H); 0.89 (s, 18H); 0.93 (d, 3H); 2.18 (s, 3H); 4.09 (m, 2H); 5.82 (d, 1H); 6.10 (t, 1H); 6.18 (d, 1H); 7.31 (d, 1H); 7.78 (d, 1H)

23. 672 mg of acetate 25 is reacted analogously to 13., and 526 mg of (7E)-(1R,3R)-1,3-bis[[(1,1-dimethylethyl)dimethylsilyl]-oxy]-24a-(thiazol-2-yl)-24a-homo-19-nor-9,10-secochola-5,7-dien-24a-ol 26 is obtained as a colorless foam.

$^1$H-NMR (CD$_2$Cl$_2$): δ=0.04 ppm (s, 12H); 0.51 (s, 3H); 0.87 (s, 18H); 0.92 (d, 3H); 4.07 (m, 2H); 4.95 (m, 1H); 5.81 (d, 1H); 6.15 (d, 1H); 7.31 (d, 1H); 7.70 (d, 1H)

24. 426 mg of alcohol 26 is treated analogously to 14., and after the diastereomers (in terms of C-24a) are separated on HPLC, 134 mg of title compound 27a and 149 mg of title compound 27b are obtained as colorless foams.

$^1$H-NMR (CD$_2$Cl$_2$/CD$_3$OD): 27a: δ=0.50 ppm (s, 3H); 0.88 (d, 3H); 3.93 (m, 1H); 4.01 (m, 1H); 4.90 (t, 1H); 5.83 (d, 1H); 6.23 (d, 1H); 7.29 (d, 1H); 7.67 (d, 1H)

27b: δ=0.50 ppm (s, 3H); 0.90 (dd, 3H); 3.93 (m, 1H); 4.01 (m, 1H); 4.90 (t, 1H); 5.83 (d, 1H); 6.23 (d, 1H); 7.29 (d, 1H); 7.67 (d, 1H)

Example 4

(7E)-(1R,3R)-1,3-Dihydroxy-24a-(thiazol-2-yl-)-24-a-homo-19-nor-9,10-secochola-5,7-dien-24a-one 29

25. 100 mg of alcohol 26 is introduced into 6 ml of dichloromethane, and 378 mg of manganese dioxide is added. It is stirred for 2 hours at room temperature, then filtered on Celite, the solvent is removed, and the residue is chromatographed on silica gel, whereby 78 mg of (7E)-(1R,3R)-1,3-bis[[(1,1-dimethylethyl)dimethylsilyl]oxy]-24a-(thiazol-2-yl)-24a-homo-19-nor-9,10-secochola-5,7-dien-24a-one 28 accumulates as a colorless foam.

$^1$H-NMR (CD$_2$Cl$_2$): δ=0.04 ppm (s, 12H); 0.51 (s, 3H); 0.84 (s, 18H); 0.93 (d, 3H); 4.05 (m, 2H); 5.80 (d, 1H); 6.15 (d, 1H); 7.66 (d, 1H); 7.97 (d, 1H)

26. 78 mg of ketone 28 is introduced into 7 ml of methanol/dichloromethane (9:1), 780 mg of activated acid Dowex ion exchanger is added, and it is stirred for 1 day at room temperature. It is filtered on Celite, rewashed thoroughly with dichloromethane, the solvent is removed, and the residue is chromatographed on silica gel, whereby 43 mg of title compound 29 is obtained as a colorless foam.

$^1$H-NMR (CD$_2$Cl$_2$): δ=0.51 ppm (s, 3H); 0.97 (d, 3H); 3.97 (m, 1H); 4.06 (m, 1H); 5.81 (d, 1H); 6.27 (d, 1H); 7.68 (d, 1H); 7.97 (d, 1H)

Example 5

(5Z,7E)-(1S,3R,24aR)-24a-(Thiazol-2-yl)-24a-homo-9,10-secochola-5,7,10(19)-triene-1,3,24a-triol 32a and (5Z,7E)-(1S,3R,24aS)-24a-(thiazol-2-yl)-24a-homo-9,10-secochola-5,7,10(19)-triene-1,3,24a-triol 32b 27. 309 mg of phosphine oxide 17, which was deprotonated with 0.25 ml of n-butyllithium solution (2.5 M in hexane), is reacted with 100 mg of ketone 24 analogously to 15., and 170 mg of (5Z,7E)-(1S,3R)-24a-(acetyloxy)-1,3-bis[[(1,1-dimethylethyl)dimethylsilyl]oxy]-24a-(thiazol-2-yl)-24a-homo-9,10-secochola-5,7,10(19)-triene 30 is obtained as a colorless foam.

$^1$H-NMR (CDCl$_3$): δ=0.07 ppm (s, 12H); 0.52 (s, 3H); 0.89 (s, 18H); 0.90 (d, 3H); 2.18 (s, 3H); 4.19 (m, 1H); 4.38 (m, 1H); 4.87 (s, 1H); 5.19 (s, 1H); 6.01 (d, 1H); 6.10 (t, 1H); 6.23 (d, 1H); 7.31 (d, 1H); 7.83 (d, 1H)

28. 170 mg of acetate 30 is reacted analogously to 13., and 149 mg of (5Z,7E)-(1S,3R)-1,3-bis[[(1,1-dimethylethyl)dimethylsilyl]oxy]-24a-(thiazol-2-yl)-24a-homo-9,10-secochola-5,7,10(19)-trien-24a-ol 31 is obtained as a colorless foam.

$^1$H-NMR (CDCl$_3$): δ=0.07 ppm (s, 12H); 0.51 (s, 3H); 0.89 (s, 18H); 0.90 (d, 3H); 2.18 (s, 3H); 4.18 (m, 1H); 4.38 (m, 1H); 4.87 (s, 1H); 5.02 (m, 1H); 5.19 (s, 1H); 6.01 (d, 1H); 6.23 (d, 1H); 7.31 (d, 1H); 7.74 (d, 1H)

29. 101 mg of alcohol 31 is treated analogously to 14., and after the diastereomers (in terms of C-24a) are separated on HPLC, 24 mg of title compound 32a and 29 mg of title compound 32b are obtained as colorless foams.

¹H-NMR (CD₂Cl₂/CD₃OD): 32a: δ=0.50 ppm (s, 3H); 0.90 (d, 3H); 4.11 (m, 1H); 4.33 (m, 1H); 4.90 (t, 1H); 4.92 (s, 1H); 5.27 (s, 1H); 6.00 (d, 1H); 6.32 (d, 1H); 7.29 (d, 1H); 7.68 (d, 1H)

32b: δ=0.51 ppm (s, 3H); 0.89 (d, 3H); 4.11 (m, 1H); 4.33 (m, 1H); 4.90 (t, 1H); 4.92 (s, 1H); 5.27 (s, 1H); 6.00 (d, 1H); 6.32 (d, 1H); 7.29 (d, 1H); 7.68 (d, 1H)

Example 6

(5Z,7E)-(1S,3R)-1,3-Dihydroxy-24a-(thiazol-2-yl)-24a-homo-9,10-secochola-5,7,10(19)-trien-24a-one 34

30. 149 mg of alcohol 31 is treated analogously to 25., and 127 mg of (5Z,7E)-(1S,3R)-1,3-bis[[(1,1-dimethylethyl)dimethylsilyl]oxy]-24a-(thiazol-2-yl)-24a-homo-9,10-secochola-5,7,10(19)-trien-24a-one 33 is obtained as a colorless foam.

¹H-NMR (CDCl₃): δ=0.07 ppm (s, 12H); 0.53 (s, 3H); 0.90 (s, 18H); 0.97 (d, 3H); 4.19 (m, 1H); 4.38 (m, 1H); 4.88 (s, 1H); 5.19 (s, 1H); 6.02 (d, 1H); 6.24 (d, 1H); 7.68 (d, 1H); 8.00 (d, 1H)

31. 21 mg of ketone 33 is treated analogously to 26., and 8 mg of title compound 34 is obtained as a colorless foam.

¹H-NMR (CD₂Cl₂): δ=0.51 ppm (s, 3H); 0.94 (d, 3H); 4.17 (m, 1H); 4.34 (m, 1H); 4.90 (s, 1H); 5.26 (s, 1H); 6.00 (d, 1H); 6.33 (d, 1H); 7.66 (d, 1H); 7.97 (d, 1H)

Example 7

(7E)-(1R,3R,24aR)-24a-(4-Methylthiazol-2-yl)-24a-homo-19-nor-9,10-secochola-5,7-diene-1,3,24a-triol 41a and (7E)-(1R,3R,24aS)-24a-(4-methylthiazol-2-yl)-24a-homo-19-nor-9,10-secochola-5,7-diene-1,3,24a-triol 41b 32. 1.3 ml of 4-methylthiazole is introduced into 25 ml of tetrahydrofuran, and 5.78 ml of n-butyllithium solution (2.5 M in hexane) is added at −78° C. After 30 minutes at this temperature, 1.06 g of aldehyde 8 in 5 ml of tetrahydrofuran is added in drops, and it is stirred for 1 more hour. Then, it is quenched with sodium chloride solution, extracted with ethyl acetate, the organic phase is washed with sodium chloride solution and dried on sodium sulfate. The solvent is removed, and the residue is chromatographed on silica gel with ethyl acetate/hexane, whereby 601 mg of [1R-[1α(1R*),3aβ,4α,7aα]]-α-[4-octahydro-7a-methyl-4-[(triethylsilyl)oxy]-1H-inden-1-yl]pentyl]-4-methylthiazol-2-methanol 35 is obtained as a colorless oil.

¹H-NMR (CDCl₃): δ=0.56 ppm (q, 6H); 0.88 (d, 3H); 0.90 (s, 3H); 0.97 (t, 9H); 2.41 (s, 3H); 4.02 (m, 1H); 4.94 (m, 1H); 6.82 (s, 1H)

33. 601 mg of alcohol 35 is treated analogously to 9., and 589 mg of [1R-[1α(1R*),3aβ,4α,7aα]]-5-[octahydro-7a-methyl-4-[(triethylsilyl)oxy]-1H-inden-1-yl]-1-(4-methylthiazol-2-yl)hexyl acetate 36 is obtained as a colorless oil.

¹H-NMR (CDCl₃): δ=0.56 ppm (q, 6H); 0.85/0.86 (d, 3H); 0.91 (s, 3H); 0.96 (t, 9H); 2.14 (s, 3H); 2.45 (s, 3H); 4.02 (m, 1H); 6.02 (t, 1H); 6.81 (s, 1H)

34. 589 mg of acetate 36 is treated analogously to 10., and 366 mg of [1R-[1α(1R*),3aβ,4α,7aα]]-1-[5-(acetyloxy)-1-methyl-5-(4-methylthiazol-2-yl)pentyl]octahydro-7a-methyl-1H-inden-4-ol 37 is obtained as a colorless oil.

¹H-NMR (CDCl₃): δ=0.87/0.88 ppm (d, 3H); 0.91 (s, 3H); 2.17 (s, 3H); 2.45 (s, 3H); 4.07 (m, 1H); 6.03 (t, 1H); 6.81 (s, 1H)

35. 360 mg of alcohol 37 is treated analogously to 11., and 340 mg of [1R-[1α(1R*),3aβ,7aα]]-1-[5-(acetyloxy)-1-methyl-5-(2-methylthiazol-2-yl)pentyl]octahydro-7a-methyl-4H-inden-4-one 38 is obtained as a colorless oil.

¹H-NMR (CDCl₃): δ=0.61 ppm (s, 3H); 0.92/0.93 (d, 3H); 2.13 (s, 3H); 2.45 (s, 3H); 6.05 (t, 1H); 6.82 (s, 1H)

36. 329 mg of phosphine oxide 13, which was deprotonated with 0.28 ml of n-butyllithium solution (2.5 M in hexane), is reacted with 113 mg of ketone 38 analogously to 12., and 98 mg of (7E)-(1R,3R)-24a-(acetyloxy)-1,3-bis[[(1,1-dimethylethyl)dimethylsilyl]oxy]-24a-(4-methylthiazol-2-yl)-24a-homo-19-nor-9,10-secochola-5,7-diene 39 is obtained as a colorless foam.

¹H-NMR (CDCl₃): δ=0.07 ppm (s, 12H); 0.53 (s, 3H); 0.89 (s, 18H); 0.90 (d, 3H); 2.15 (s, 3H); 2.46 (s, 3H); 4.09 (m, 2H); 5.81 (d, 1H); 6.04 (t, 1H); 6.18 (d, 1H); 6.83 (s, 1H)

37. 93 mg of acetate 39 is reacted analogously to 13., and 72 mg of (7E)-(1R,3R)-1,3-bis[[(1,1-dimethylethyl)dimethylsilyl]oxy]-24a-(4-methylthiazol-2-yl)-24a-homo-19-nor-9,10-secochola-5,7-dien-24a-ol 40 is obtained as a colorless foam.

¹H-NMR (CDCl₃): δ=0.07 ppm (s, 12H); 0.53 (s, 3H); 0.89 (s, 18H); 0.93 (d, 3H); 2.45 (s, 3H); 4.08 (m, 2H); 4.95 (m, 1H); 5.82 (d, 1H); 6.18 (d, 1H); 6.82 (s, 1H)

38. 72 mg of alcohol 40 is treated analogously to 14., and after the diastereomers (in terms of C-24a) are separated by HPLC, 15 mg of title compound 41a and 21 mg of title compound 41b are obtained as colorless foams.

¹H-NMR (CD₂Cl₂): 41a: δ=0.51 ppm (s, 3H); 0.90 (d, 3H); 2.36 (s, 3H); 3.94 (m, 1H); 4.02 (m, 1H); 4.88 (m, 1H); 5.83 (d, 1H); 6.24 (d, 1H); 6.82 (s, 1H)

41b: δ=0.51 ppm (s, 3H); 0.90 (d, 3H); 2.36 (s, 3H); 3.94 (m, 1H); 4.02 (m, 1H); 4.86 (m, 1H); 5.83 (d, 1H); 6.24 (d, 1H); 6.83 (s, 1H)

Example 8

(7E)-(1R,3R)-1,3-Dihydroxy-24a-(4-methylthiazol-2-yl)-24a-homo-19-nor-9,10-secochola-5,7-dien-24a-one 43

39. 53 mg of alcohol 40 is treated analogously to 25., whereby 42 mg of (7E)-(1R,3R)-1,3-bis[[(1,1-dimethylethyl)dimethylsilyl]oxy]-24a-(4-methylthiazol-2-yl)-24a-homo-19-nor-9,10-secochola-5,7-dien-24a-one 42 accumulates as a colorless foam.

¹H-NMR (CDCl₃): δ=0.07 ppm (s, 12H); 0.53 (s, 3H); 0.89 (s, 18H); 0.97 (d, 3H); 2.54 (s, 3H); 4.09 (m, 2H); 5.81 (d, 1H); 6.18 (d, 1H); 7.23 (s, 1H)

40. 42 mg of ketone 42 is treated analogously to 26., whereby 13 mg of title compound 43 accumulates as a colorless foam.

¹H-NMR (CD₂Cl₂/CD₃OD): δ=0.52 ppm (s, 3H); 0.93 (d, 3H); 2.48 (s, 3H); 3.94 (m, 1H); 4.03 (m, 1H); 5.82 (d, 1H); 6.23 (d, 1H); 7.23 (s, 1H)

Example 9

(5Z,7E)-(1S,3R,24aR)-24a-(4-Methylthiazol-2-yl)-24a-homo-9,10-secochola-5,7,10(19)-triene-1,3,24a-triol 46a and (5Z,7E)-(1S,3R,24aS)-24a-(4-methylthiazol-2-yl)-24a-homo-9,10-secochola-5,7,10(19)-triene-1,3,24a-triol 46b 41. 337 mg of phosphine oxide 17, which was deprotonated with 0.28 ml of n-butyllithium solution (2.5 M in hexane), is reacted with 113 mg of ketone 38 analogously to 15., and 170 mg of (5Z,7E)-(1S,3R)-24a-(acetyloxy)-1,3-bis[[(1,1-dimethylethyl)dimethylsilyl]oxy]-24a-(4-methylthiazol-2-yl)-24a-homo-9,10-secochola-5,7,10(19)-triene 44 is obtained as a colorless foam.

$^1$H-NMR (CDCl$_3$): δ=0.07 ppm (s, 12H); 0.52 (s, 3H); 0.89 (s, 18H); 0.90 (d, 3H); 2.14 (s, 3H); 2.45 (s, 3H); 4.19 (m, 1H); 4.38 (m, 1H); 4.88 (s, 1H); 5.19 (s, 1H); 6.02 (d, 1H); 6.03 (m, 1H); 6.23 (d, 1H); 6.83 (s, 1H)

42. 170 mg of acetate 44 is reacted analogously to 13., and 109 mg of (5Z,7E)-(1S,3R)-1,3-bis[[(1,1-dimethylethyl)dimethylsilyl]oxy]-24a-(4-methylthiazol-2-yl)-24a-homo-9,10-secochola-5,7,10(19)-trien-24a-ol 45 is obtained as a colorless foam.

$^1$H-NMR (CDCl$_3$): δ=0.07 ppm (s, 12H); 0.52 (s, 3H); 0.90 (s, 18H); 0.93 (d, 3H); 2.45 (s, 3H); 4.19 (m, 1H); 4.38 (m, 1H); 4.88 (s, 1H); 4.95 (m, 1H); 5.19 (s, 1H); 6.02 (d, 1H); 6.23 (d, 1H); 6.83 (s, 1H)

43. 105 mg of alcohol 45 is treated analogously to 14., and after the diastereomers (in terms of C-24a) are separated by HPLC, 30 mg of title compound 46a and 29 mg of title compound 46b are obtained as colorless foams.

$^1$H-NMR (CD$_2$Cl$_2$): δ=0.50 ppm (s, 3H); 0.90 (d, 3H); 2.38 (s, 3H); 4.17 (m, 1H); 4.36 (m, 1H); 4.88 (dd, 1H); 4.94 (s, 1H); 5.27 (s, 1H); 6.00 (d, 1H); 6.36 (d, 1H); 6.81 (s, 1H)

46b: δ=0.50 ppm (s, 3H); 0.89 (d, 3H); 2.38 (s, 3H); 4.17 (m, 1H); 4.36 (m, 1H); 4.84 (dd, 1H); 4.94 (s, 1H); 5.27 (s, 1H); 6.00 (d, 1H); 6.35 (d, 1H); 6.81 (s, 1H)

Example 10

(5Z,7E)-(1S,3R)-1,3-Dihydroxy-24a-(4-methylthiazol-2-yl)-24a-homo-9,10-secochola-5,7,10(19)-trien-24a-one 48

44. 48 mg of alcohol 45 is treated analogously to 25., and 40 mg of (5Z,7E)-(1S,3R)-1,3-bis[[(1,1-dimethylethyl)dimethylsilyl]-oxy]-24a-(4-methylthiazol-2-yl)-24a-homo-9,10-secochola-5,7,10(19)-trien-24a-one 47 is obtained as a colorless foam.

$^1$H-NMR (CDCl$_3$): δ=0.07 ppm (s, 12H); 0.52 (s, 3H); 0.88 (s, 18H); 0.95 (d, 3H); 2.52 (s, 3H); 4.19 (m, 1H); 4.37 (m, 1H); 4.84 (s, 1H); 5.18 (s, 1H); 6.00 (d, 1H); 6.23 (d, 1H); 7.21 (s, 1H)

45. 39 mg of ketone 47 is treated analogously to 26., and 11 mg of title compound 48 is obtained as a colorless foam.

$^1$H-NMR (CD$_2$Cl$_2$): δ=0.53 ppm (s, 3H); 0.95 (d, 3H); 2.45 (s, 3H); 4.15 (m, 1H); 4.36 (m, 1H); 4.95 (s, 1H); 5.27 (s, 1H); 6.00 (d, 1H); 6.35 (d, 1H); 7.24 (s, 1H)

Example 11

(7E)-(1R,3R,24aR)-24a-(Thien-2-yl)-24a-homo-19-nor-9,10-secochola-5,7-diene-1,3,24a-triol 55a and (7E)-(1R,3R,24aS)-24a-(thien-2-yl)-24a-homo-19-nor-9,10-secochola-5,7-diene-1,3,24a-triol 55b 46. 0.65 ml of thiophene is introduced into 20 ml of tetrahydrofuran, and 3.27 ml of n-butyllithium solution (2.5 M in hexane) is added at −78° C. After 30 minutes at this temperature, 600 mg of aldehyde 8 in 3 ml of tetrahydrofuran is added in drops, and it is stirred for 1 more hour. Then, it is quenched with sodium chloride solution, extracted with ethyl acetate, the organic phase is washed with sodium chloride solution and dried on sodium sulfate. The solvent is removed, and the residue is chromatographed on silica gel with ethyl acetate/hexane, whereby 673 mg of [1R-[1α(1R*),3aβ,4α,7aα]]-α-[4-[octahydro-7a-methyl-4-[(triethylsilyl)oxy]-1H-inden-1-yl]pentyl]thiophene-2-methanol 49 is obtained as a colorless oil.

$^1$H-NMR (CDCl$_3$): δ=0.56 ppm (q, 6H); 0.89 (d, 3H); 0.91 (s, 3H); 0.97 (t, 9H); 4.03 (m, 1H); 4.93 (m, 1H); 6.98 (m, 2H); 7.27 (m, 1H)

47. 673 mg of alcohol 49 is treated analogously to 9., and 712 mg of [1R-[1α(1R*),3aβ,4α,7aα]]-5-[octahydro-7a-methyl-4-[(triethylsilyl)oxy]-1H-inden-1-yl]-1-(thien-2-yl) hexyl-acetate 50 is obtained as a colorless oil.

$^1$H-NMR (CDCl$_3$): δ=0.56 ppm (q, 6H); 0.87/0.88 (d, 3H); 0.91 (s, 3H); 0.97 (t, 9H); 2.08 (s, 3H); 4.02 (m, 1H); 6.05 (t, 1H); 6.98 (m, 1H); 7.05 (m, 1H); 7.27 (m, 1H)

48. 704 mg of acetate 50 is treated analogously to 10., and 412 mg of [1R-[1α(1R*),3aβ,4α,7aα]]-1-[5-(acetyloxy)-1-methyl-5-(thien-2-yl)pentyl]octahydro-7a-methyl-1H-inden-4-ol 51 is obtained as a colorless oil.

$^1$H-NMR (CDCl$_3$): δ=0.87/0.88 ppm (d, 3H); 0.92 (s, 3H); 2.08 (s, 3H); 4.07 (m, 1H); 6.03 (t, 1H); 6.97 (m, 1H); 7.07 (m, 1H); 7.28 (m, 1H)

49. 407 mg of alcohol 51 is treated analogously to 11., and 373 mg of [1R-[1α(1R*),3aβ,7aα]]-1-[5-(acetyloxy)-1-methyl-5-(thien-2-yl)pentyl]octahydro-7a-methyl-4H-inden-4-one 52 is obtained as a colorless oil.

$^1$H-NMR (CDCl$_3$): δ=0.62 ppm (s, 3H); 0.92/0.93 (d, 3H); 2.08 (s, 3H); 6.04 (t, 1H); 6.98 (m, 1H); 7.05 (m, 1H); 7.28 (m, 1H)

50. 329 mg of phosphine oxide 13, which was deprotonated with 0.28 ml of n-butyllithium solution (2.5 M in hexane), is reacted with 109 mg of ketone 52 analogously to 12., and 183 mg of (7E)-(1R,3R)-24a-(acetyloxy)-1,3-bis [[(1,1-dimethylethyl)dimethylsilyl]oxy]-24a-(thien-2-yl)-24a-homo-19-nor-9,10-secochola-5,7-diene 53 is obtained as a colorless foam.

$^1$H-NMR (CDCl$_3$): δ=0.07 ppm (s, 12H); 0.53 (s, 3H); 0.90 (s, 18H); 0.90 (d, 3H); 2.07 (s, 3H); 4.08 (m, 2H); 5.81 (d, 1H); 6.04 (t, 1H); 6.18 (d, 1H); 6.98 (m, 1H); 7.05 (m, 1H); 7.29 (m, 1H)

51. 178 mg of acetate 53 is reacted analogously to 13., and 138 mg of (7E)-(1R,3R)-1,3-bis[[(1,1-dimethylethyl)dimethylsilyl]-oxy]-24a-(thien-2-yl)-24a-homo-19-nor-9,10-secochola-5,7-dien-24a-ol 54 is obtained as a colorless foam.

$^1$H-NMR (CDCl$_3$): δ=0.07 ppm (s, 12H); 0.53 (s, 3H); 0.89 (s, 18H); 0.91 (d, 3H); 4.09 (m, 2H);-4.94 (m, 1H); 5.82 (d, 1H); 6.18 (d, 1H); 6.98 (m, 2H); 7.28 (m, 1H)

52. 97 mg of alcohol 54 is treated analogously to 14., and after the diastereomers (in terms of C-24a) are separated by HPLC, 19 mg of title compound 55a and 24 mg of title compound 55b are obtained as colorless foams.

$^1$H-NMR (CD$_2$Cl$_2$): 55a: δ=0.52 ppm (s, 3H); 0.90 (d, 3H); 3.95 (m, 1H); 4.02 (m, 1H); 4.87 (dd, 1H); 5.84 (d, 1H); 6.25 (d, 1H); 6.98 (m, 2H); 7.23 (m, 1H)

41b: δ=0.52 ppm (s, 3H); 0.89 (d, 3H); 3.95 (m, 1H); 4.02 (m, 1H); 4.86 (t, 1H); 5.84 (d, 1H); 6.25 (d, 1H); 6.97 (m, 2H); 7.22 (m, 1H)

Example 12

(7E)-(1R,3R)-1,3-Dihydroxy-24a-(thien-2-yl)-24a-homo-19-nor-9,10-secochola-5,7-dien-24a-one 57

53. 40 mg of alcohol 54 is treated analogously to 25., whereby 28 mg of (7E)-(1R,3R)-1,3-bis[[(1,1-dimethylethyl)dimethylsilyl]-oxy]-24a-(thien-2-yl)-24a-homo-19-nor-9,10-secochola-5,7-dien-24a-one 56 accumulates as a colorless foam.

¹H-NMR (CDCl₃): δ=0.07 ppm (s, 12H); 0.53 (s, 3H); 0.88 (s, 18H); 0.98 (d, 3H); 4.09 (m, 2H); 5.81 (d, 1H); 6.18 (d, 1H); 7.14 (dd, 1H); 7.62 (d, 1H); 7.72 (d, 1H)

54. 27 mg of ketone 42 is treated analogously to 26., whereby 13 mg of title compound 57 accumulates as a colorless foam.

¹H-NMR (CD₂Cl₂): δ=0.52 ppm (s, 3H); 0.92 (d, 3H); 3.93 (m, 1H); 4.03 (m, 1H); 5.82 (d, 1H); 6.23 (d, 1H); 7.12 (dd, 1H); 7.60 (d, 1H); 7.67 (d, 1H)

Example 13

(5Z,7E)-(1S,3R,24aR)-24a-(Thien-2-yl)-24a-homo-9,10-secochola-5,7,10(19)-triene-1,3,24a-triol 60a and (5Z,7E)-(1S,3R,24aS)-24a-(thien-2-yl)-24a-homo-9,10-secochola-5,7,10(19)-triene-1,3,24a-triol 60b 55. 350 mg of phosphine oxide 17, which was deprotonated with 0.29 ml of n-butyllithium solution (2.5 M in hexane), is reacted with 113 mg of ketone 52 analogously to 15, and 93 mg of (5Z,7E)-(1S,3R)-24a-(acetyloxy)-1,3-bis-[[(1,1-dimethylethyl)dimethylsilyl]oxy]-24a-(thien-2-yl)-24a-homo-9,10-secochola-5,7,10(19)-triene 58 is obtained as a colorless foam.

¹H-NMR (CDCl₃): δ=0.07 ppm (s, 12H); 0.53 (s, 3H); 0.90 (s, 18H); 0.90 (d, 3H); 2.07 (s, 3H); 4.19 (m, 1H); 4.38 (m, 1H); 4.88 (s, 1H); 5.20 (s, 1H); 6.01 (d, 1H); 6.02 (t, 1H); 6.24 (d, 1H); 6.98 (m, 1H); 7.06 (m, 1H); 7.28 (m, 1H)

56. 92 mg of acetate 58 is reacted analogously to 13., and 79 mg of (5Z,7E)-(1S,3R)-1,3-bis[[dimethyl(1,1-dimethylethyl)silyl]-oxy]-24a-(thien-2-yl)-24a-homo-9,10-secochola-5,7,10(19)-trien-24a-ol 59 is obtained as a colorless foam.

¹H-NMR (CDCl₃): δ=0.07 ppm (s, 12H); 0.52 (s, 3H); 0.88 (s, 18H); 0.90 (d, 3H); 4.18 (m, 1H); 4.38 (m, 1H); 4.88 (s, 1H); 4.93 (m, 1H); 5.18 (s, 1H); 6.00 (d, 1H); 6.22 (d, 1H); 6.98 (m, 2H); 7.28 (m, 1H)

57. 78 mg of alcohol 59 is treated analogously to 14., and after the diastereomers (in terms of C-24a) are separated by HPLC, 21 mg of title compound 60a and 24 mg of title compound 60b are obtained as colorless foams.

¹H-NMR (CD₂Cl₂/CD₃OD): 60a: δ=0.50 ppm (s, 3H); 0.88 (d, 3H); 4.10 (m, 1H); 4.32 (m, 1H); 4.86 (dd, 1H); 494 (s, 1H); 5.26 (s, 1H); 6.00 (d, 1H); 6.27 (d, 1H); 6.92 (m, 2H); 7.20 (m, 1H)

60b: δ=0.50 ppm (s, 3H); 0.86 (d, 3H); 4.10 (m, 1H); 4.31 (m, 1H); 4.83 (t, 1H); 4.94 (s, 1H); 5.26 (s, 1H); 6.00 (d, 1H); 6.27 (d, 1H); 6.92 (m, 2H); 7.20 (m, 1H)

Example 14

(7E)-(1R,2S,3R,24aR)-24a-Thien-2-yl-24a-homo-19-nor-9,10-secochola-5,7-diene-1,2,3,24-tetrol 64a and (7E)-(1R,2S,3R,24aS)-24a-thien-2-yl-24a-homo-19-nor-9,10-secochola-5,7-diene-1,2,3,24-tetrol 64b 58. 405 mg of [2-[[3R-(3R,4S,5R)]-3,4,5-tris[[(1,1-dimethylethyl)dimethylsilyl]oxy]cyclo-hexylidene]ethyl]diphenylphosphine oxide 61a [H. F. DeLuca et al. J. Med. Chem. 37, 3730 (1994)] is introduced into 6 ml of tetrahydrofuran, and 0.28 ml of n-butyllithium solution (2.5 M in hexane) is added in drops at −78° C. At −30° C., 109 mg of ketone 52 is added after 10 minutes, and it is stirred for 1 hour at this temperature. Then, it is quenched with sodium chloride solution, extracted with ethyl acetate, the organic phase is washed with sodium chloride solution, dried on sodium sulfate, and the solvent is removed. The residue is chromatographed on silica gel with ethyl acetate/hexane, whereby 206 mg of (7E)-(1R,2S,3R)-24a-(acetyloxy)-24a-(thien-2-yl)-1,2,3-tris[[(1,1-dimethylethyl)dimethylsilyl]-oxy]-24a-homo-19-nor-9,10-secochola-5,7-diene 62 is obtained as a colorless foam.

¹H-NMR (CDCl₃): δ=0.02–0.07 ppm (4×s, 18H); 0.53 (s, 3H); 0.83 (s, 9H); 0.89 (s, 18H); 0.90 (d, 3H); 2.07 (s, 3H); 3.64 (m, 1H); 3.80 (m, 1H); 3.85 (m, 1H); 5.84 (d, 1H); 6.03 (t, 1H); 6.04 (d, 1H); 6.97 (m, 2H); 7.05 (m, 1H)

59. 205 mg of acetate 62 is reacted analogously to 13., and 180 mg of (7E)-(1R,2S,3R)-24a-(thien-2-yl)-1,2,3-tris[[(1,1-dimethylethyl)dimethylsilyl]oxy]-24a-homo-19-nor-9,10-secochola-5,7-dien-24a-ol 63 is obtained as a colorless foam.

¹H-NMR (CDCl₃): δ=0.02–0.07 ppm (4×s, 18H); 0.53 (s, 3H); 0.83 (s, 9H); 0.89 (s, 18H); 0.90 (d, 3H); 3.63 (m, 1H); 3.79 (m, 1H); 3.83 (m, 1H); 4.93 (m, 1H); 5.83 (d, 1H); 6.04 (d, 1H); 6.99 (m, 2H); 7.28 (m, 1H)

60. 134 mg of alcohol 63 is treated analogously to 14., and after the diastereomers (in terms of C-24a) are separated by HPLC, 18 mg of title compound 64a and 25 mg of title compound 64b are obtained as colorless foams.

¹H-NMR (CD₂Cl₂): 64a: δ=0.52 ppm (s, 3H); 0.89 (d, 3H); 3.44 (dd, 1H); 3.72 (m, 1H); 4.00 (m, 1H); 4.87 (dd, 1H); 5.76 (d, 1H); 6.28 (d, 1H); 6.93 (m, 2H); 7.22 (m, 1H)

64b: δ=0.53 ppm (s, 3H); 0.90 (d, 3H); 3.46 (dd, 1H); 3.70 (m, 1H); 4.00 (m, 1H); 4.87 (t, 1H); 5.77 (d, 1H); 6.28 (d, 1H); 6.93 (m, 2H); 7.21 (m, 1H)

Example 15

(7E)-(1R,2S,3R)-24a-Thien-2-yl-1,2,3-trihydroxy-24a-homo-9,10-secochola-5,7-dien-24a-one 66

61. 45 mg of alcohol 63 is treated analogously to 25., whereby 38 mg of (7E)-(1R,2S,3R)-24a-(thien-2-yl)-1,2,3-tris[[(1,1-dimethylethyl)dimethylsilyl]oxy]-24a-homo-19-nor-9,10-secochola-5,7-dien-24a-one 65 accumulates as a colorless foam.

¹H-NMR (CDCl₃): δ=0.02–0.07 ppm (4×s, 18H); 0.53 (s, 3H); 0.83 (s, 9H); 0.90 (s, 18H); 0.97 (d, 3H); 3.62 (m, 1H); 3.80 (m, 1H); 3.85 (m, 1H); 5.85 (d, 1H) 6.06 (d, 1H); 7.12 (dd, 1H); 7.61 (d, 1H); 7.70 (d, 1H)

62. 38 mg of ketone 65 is treated analogously to 26., whereby 13 mg of title compound 66 accumulates as a colorless foam.

¹H-NMR (CD₂Cl₂): δ=0.53 ppm (s, 3H); 0.95 (d, 3H); 3.48 (m, 1H); 3.74 (m, 1H); 4.03 (m, 1H); 5.85 (d, 1H); 6.30 (d, 1H); 7.13 (dd, 1H); 7.61 (d, 1H); 7.69 (d, 1H)

Example 16

(7E)-(1R,3R,24aR)-24a-(4-Methylthien-2-yl)-24a-homo-19-nor-9,10-secochola-5,7-diene-1,3,24a-triol 73a and (7E)-(1R,3R,24aS)-24a-(4-methylthien-2-yl)-24a-homo-19-nor-9,10-secochola-5,7-diene-1,3,24a-triol 73b 63. 0.79 ml of 3-methylthiophene is introduced into 20 ml of tetrahydrofuran, and 3.27 ml of n-butyllithium solution (2.5 M in hexane) is aded at −78° C. After 30 minutes at this temperature, 600 mg of aldehyde 8 in 3 ml of tetrahydrofuran is added in drops, and it is stirred for 1 more hour. Then, it is quenched with sodium chloride solution, extracted with ethyl acetate, the organic phase is washed with sodium chloride solution and dried on sodium sulfate. The solvent is removed, and the residue is chromatographed on silica gel with ethyl acetate/hexane, whereby 681 mg of [1R-[1α(1R*),3aβ,4α,7aα]]-α-[4-(octahydro-7a-methyl-4-[(triethylsilyl)oxy]-1H-inden-1-yl]pentyl]-4-methylthiophene-2-methanol 67 is obtained as a colorless oil.

$^1$H-NMR (CDCl$_3$): δ=0.55 ppm (q, 6H); 0.88 (d, 3H); 0.90 (s, 3H); 0.96 (t, 9H); 2.23 (s, 3H); 4.03 (m, 1H); 4.83 (m, 1H); 6.80 (s, 1H); 6.82 (s, 1H)

64. 671 mg of alcohol 67 is treated analogously to 9., and 692 mg of [1R-[1α(R*),3aβ,4α,7aα]]-5-[octahydro-7a-methyl-4-[(triethylsilyl)oxy]-1H-inden-1-yl]-1-(4-methylthien-2-yl)hexyl-acetate 68 is obtained as a colorless oil.

$^1$H-NMR (CDCl$_3$): δ=0.56 ppm (q, 6H); 0.87/0.88 (d, 3H); 0.90 (s, 3H); 0.96 (t, 9H); 2.08 (s, 3H); 2.25 (s, 3H); 4.03 (m, 1H); 5.98 (t, 1H); 6.83 (s, 1H); 6.85 (s, 1H)

65. 682 mg of acetate 68 is treated analogously to 10., and 425 mg of [1R-[1α(1R*),3aβ,4α,7aα]]-1-[5-(acetyloxy)-1-methyl-5-(4-methylthien-2-yl)pentyl]octahydro-7a-methyl-1H-inden-4-ol 69 is obtained as a colorless oil.

$^1$H-NMR (CDCl$_3$): δ=0.87/0.88 ppm (d, 3H); 0.92 (s, 3H); 2.08 (s, 3H); 2.23 (s, 3H); 4.07 (m, 1H); 5.98 (t, 1H); 6.82 (s, 1H); 6.85 (s, 1H)

66. 415 mg of alcohol 69 is treated analogously to 11., and 352 mg of [1R-[1α(1R*),3aβ,7aα]]-1-[5-(acetyloxy)-1-methyl-5-(4-methylthien-2-yl)pentyl]octahydro-7a-methyl-4H-inden-4-one 70 is obtained as a colorless oil.

$^1$H-NMR (CDCl$_3$): δ=0.62 ppm (s, 3H); 0.92/0.93 (d, 3H); 2.08 (s, 3H); 2.25 (s, 3H); 5.97 (t, 1H); 6.83 (s, 1H); 6.84 (s, 1H)

67. 306 mg of phosphine oxide 13, which was deprotonated with 0.26 ml of n-butyllithium solution, is reacted with 105 mg of ketone (7E)-(1R,3R)-24a-(acetyloxy)-1,3-bis[[(1,1-dimethylethyl)dimethylsilyl]oxy]-24a-(4-methylthien-2-yl)-24a-homo-19-nor-9,10-secochola-5,7-diene 70 analogously to 12., and 166 mg of 71 is obtained as a colorless foam.

$^1$H-NMR (CDCl$_3$): δ=0.07 ppm (s, 12H); 0.53 (s, 3H); 0.90 (s, 18H); 0.91 (d, 3H); 2.07 (s, 3H); 2.23 (s, 3H); 4.09 (m, 2H); 5.81 (d, 1H); 5.97 (t, 1H); 6.18 (d, 1H); 6.82 (s, 1H); 6.84 (s, 1H)

68. 165 mg of acetate 71 is treated analogously to 13., and 128 mg of (7E)-(1R,3R)-1,3-bis[[dimethyl(1,1-dimethylethyl)silyl]oxy]-24a-(4-methylthien-2-yl)-24a-homo-19-nor-9,10-secochola-5,7-dien-24a-ol 72 is obtained as a colorless foam.

$^1$H-NMR (CDCl$_3$): δ=0.07 ppm (s, 12H); 0.54 (s, 3H); 0.89 (s, 18H); 0.91 (d, 3H); 2.25 (s, 3H); 4.09 (m, 2H); 4.85 (m, 1H); 5.82 (d, 1H); 6.18 (d, 1H); 6.80 (s, 1H); 6.82 (s, 1H)

69. 91 mg of alcohol 72 is treated analogously to 14., and after the diastereomers (in terms of C-24a) are separated by HPLC, 16 mg of title compound 73a and 19 mg of title compound 73b are obtained as colorless foams.

$^1$H-NMR (CD$_2$Cl$_2$/CD$_3$OD): 73a: δ=0.51 ppm (s, 3H); 0.91 (d, 3H); 2.18 (s, 3H); 3.94 (m, 1H); 4.02 (m, 1H); 4.76 (t, 1H); 5.84 (d, 1H); 6.25 (d, 1H); 6.75 (s, 1H); 6.77 (s, 1H);

73b: δ=0.51 ppm (s, 3H); 0.90 (d, 3H); 2.18 (s, 3H); 3.94 (m, 1H); 4.02 (m, 1H); 4.78 (t, 1H); 5.84 (d, 1H); 6.25 (d, 1H); 6.75 (s, 1H); 6.77 (s, 1H)

Example 17

(7E)-(1R,3R)-1,3-Dihydroxy-24a-(4-methylthien-2-yl)-24a-homo-19-nor-9,10-secochola-5,7-dien-24a-one 75

70. 36 mg of alcohol 72 is treated analogously to 25., whereby 30 mg of (7E)-(1R,3R)-1,3-bis[[dimethyl(1,1-dimethylethyl)silyl]oxy]-24a-(4-methylthien-2-yl)-24a-homo-19-nor-9,10-secochola-5,7-dien-24a-one 74 accumulates as a colorless foam.

$^1$H-NMR (CDCl$_3$): δ=0.07 ppm (s, 12H); 0.54 (s, 3H); 0.88 (s, 18H); 0.98 (d, 3H); 2.30 (s, 3H); 4.09 (m, 2H); 5.82 (d, 1H); 6.18 (d, 1H); 7.22 (s, 1H); 7.52 (s, 1H)

71. 29 mg of ketone 74 is treated analogously to 26., whereby 13 mg of 75 of the title compound accumulates as a colorless foam.

$^1$H-NMR (CD$_2$Cl$_2$): δ=0.52 ppm (s, 3H); 0.94 (d, 3H); 2.27 (s, 3H); 3.95 (m, 1H); 4.04 (m, 1H); 5.82 (d, 1H); 6.24 (d, 1H); 7.19 (s, 1H); 7.48 (s, 1H)

Example 18

(5Z,7E)-(1S,3R,24aR)-24a-(4-Methylthien-2-yl)-24a-homo-9,10-secochola-5,7,10(19)-triene-1,3,24a-triol 78a and (5Z,7E)-(1S,3R,24aS)-24a-(4-methylthien-2-yl)-24a-homo-9,10-secochola-5,7,10(19)-triene-1,3,24a-triol 78b 72. 316 mg of phosphine oxide 17, which was deprotonated with 0.26 ml of n-butyllithium solution (2.5 M in hexane), is reacted with 106 mg of ketone 70 analogously to 15., and 177 mg of (5Z,7E)-(1S,3R)-24a-(acetyloxy)-1,3-bis[[(1,1-dimethylethyl)dimethylsilyl]oxy]-24a-(4-methylthien-2-yl)-24a-homo-9,10-secochola-5,7,10(19)-triene 76 is obtained as a colorless foam.

$^1$H-NMR (CDCl$_3$): δ=0.07 ppm (s, 12H); 0.53 (s, 3H); 0.89 (s, 18H); 0.90 (d, 3H); 2.08 (s, 3H); 2.23 (s, 3H); 4.19 (m, 1H); 4.38 (m, 1H); 4.88 (s, 1H); 5.20 (s, 1H); 5.98 (t, 1H); 6.01 (d, 1H); 6.23 (d, 1H); 6.83 (s, 1H); 6.85 (s, 1H)

73. 176 mg of acetate 76 is reacted analogously to 13., and 149 mg of (5Z,7E)-(1S,3R)-1,3-bis[[(1,1-dimethylethyl)dimethylsilyl]-oxy]-24a-(4-methylthien-2-yl)-24a-homo-9,10-secochola-5,7,10(19)-trien-24a-ol 77 is obtained as a colorless foam.

$^1$H-NMR (CDCl$_3$): δ=0.07 ppm (s, 12H); 0.53 (s, 3H); 0.89 (s, 18H); 0.90 (d, 3H); 2.23 (s, 3H); 4.19 (m, 1H); 4.38 (m, 1H); 4.88 (s, 1H); 4.95 (m, 1H); 5.19 (s, 1H); 6.02 (d, 1H); 6.25 (d, 1H); 6.80 (s, 1H); 6.82 (s, 1H)

74. 103 mg of alcohol 77 is treated analogously to 14., and after the diastereomers (in terms of C-24a) are separated by HPLC, 26 mg of title compound 78a and 27 mg of title compound 78b are obtained as colorless foams.

$^1$H-NMR (CD$_2$Cl$_2$/CD$_3$OD): 78a: δ=0.50 ppm (s, 3H); 0.88 (d, 3H); 2.17 (s, 3H); 4.09 (m, 1H); 4.30 (m, 1H); 4.76 (t, 1H); 4.92 (s, 1H); 5.27 (s, 1H); 6.00 (d, 1H); 6.28 (d, 1H); 6.82 (s, 1H); 6.84 (s, 1H)

78b: δ=0.50 ppm (s, 3H); 0.89 (d, 3H); 2.17 (s, 3H); 4.09 (m, 1H): 4.30 (m, 1H); 4.78 (t, 1H); 4.92 (s, 1H); 5.27 (s, 1H); 6.00 (d, 1H); 6.28 (d, 1H); 6.82 (s, 1H); 6.84 (s, 1H)

Example 19

(5Z,7E)-(1S,3R)-1,3-Dihydroxy-24a-(4-methylthien-2-yl)-24a-homo-9,10-secochola-5,7,10(19)-trien-24a-one 80

75. 45 mg of alcohol 77 is treated analogously to 25., whereby 20 mg of (5Z,7E)-(1S,3R)-1,3-bis[[(1,1-dimethylethyl)dimethylsilyl]oxy]-24a-(4-methylthien-2-yl)-24a-homo-9,10-secochola-5,7,10(19)-trien-24a-one 79 accumulates as a colorless foam.

$^1$H-NMR (CDCl$_3$): δ=0.06 ppm (s, 12H); 0.53 (s, 3H); 0.88 (s, 18H); 0.97 (d, 3H); 2.29 (s, 3H); 4.18 (m, 1H); 4.38

(m, 1H); 4.96 (s, 1H); 5.18 (s, 1H); 6.00 (d, 1H); 6.23 (d, 1H); 7.22 (s, 1H); 7.52 (s, 1H)

76. 19 mg of ketone 79 is treated analogously to 26., whereby 9 mg of title compound 80 accumulates as a colorless foam.

$^1$H-NMR (CD$_2$Cl$_2$): δ=0.52 ppm (s, 3H); 0.94 (d, 3H); 2.27 (s, 3H); 4.16 (m, 1H); 4.36 (m, 1H); 4.94 (s, 1H); 5.28 (s, 1H); 5.98 (d, 1H); 6.36 (d, 1H); 7.20 (s, 1H); 7.48 (s, 1H)

Example 20

(7E)-(1R,2S,3R,24aR)-24a-(4-Methylthien-2-yl)-24a-homo-19-nor-9,10-secochola-5,7-diene-1,2,3,24-tetrol 83a and (7E)-(1R,2S,3R,24aS)-24a-(4-methylthien-2-yl)-24a-homo-19-nor-9,10-secochola-5,7-diene-1,2,3,24-tetrol 83b 77. 377 mg of phosphine oxide 61a is introduced into 6 ml of tetrahydrofuran, and 0.26 ml of n-butyllithium solution (2.5 M in hexane) is added in drops at −78° C. 105 mg of ketone 70 is added at −30° C. after 10 minutes, and it is stirred for 1 hour at this temperature. Then, it is quenched with sodium chloride solution, extracted with ethyl acetate, the organic phase is washed with sodium chloride solution, dried on sodium sulfate, and the solvent is removed. The residue is chromatographed on silica gel with ethyl acetate/hexane, whereby 174 mg of (7E)-(1R,2S,3R)-24a-(acetyloxy)-24a-(4-methylthien-2-yl)-1,2,3-tris[[(1,1-dimethylethyl)dimethylsilyl]oxy]-24a-homo-19-nor-9,10-secochola-5,7-diene 81 is obtained as a colorless foam.

$^1$H-NMR (CDCl$_3$): δ=0.02–0.07 ppm (4×s, 18H); 0.53 (s, 3H); 0.83 (s, 9H); 0.89 (s, 18H); 0.90 (d, 3H); 2.06 (s, 3H); 2.22 (s, 3H); 3.63 (m, 1H); 3.80 (m, 1H); 3.85 (m, 1H); 5.85 (d, 1H); 5.97 (t, 1H); 6.05 (d, 1H); 6.82 (s, 2H); 6.84 (s, 1H)

78. 173 mg of acetate 81 is reacted analogously to 13., and 146 mg of (7E)-(1R,2S,3R)-24a-(4-methylthien-2-yl)-1,2,3-tris[[(1,1-dimethylethyl)dimethylsilyl]oxy]-24a-homo-19-nor-9,10-secochola-5,7-dien-24a-ol 82 is obtained as a colorless foam.

$^1$H-NMR (CDCl$_3$): δ=0.02–0.07 ppm (4×s, 18H); 0.53 (s, 3H); 0.83 (s, 9H); 0.89 (s, 18H); 0.90 (d, 3H); 2.22 (s, 3H); 3.63 (m, 1H); 3.79 (m, 1H); 3.84 (m, 1H); 4.93 (m, 1H); 5.83 (d, 1H); 6.04 (d, 1H); 6.78 (s, 1H); 6.80 (s, 1H)

79. 99 mg of alcohol 82 is treated analogously to 14., and after the diastereomers (in terms of C-24a) are separated by HPLC, 19 mg of title compound 83a and 23 mg of title compound 83b are obtained as colorless foams.

$^1$H-NMR (CD$_2$Cl$_2$): 83a: δ=0.52 ppm (s, 3H); 0.88 (d, 3H); 2.18 (s, 3H); 3.45 (m, 1H); 3.70 (m, 1H); 4.00 (m, 1H); 4.78 (t, 1H); 5.77 (d, 1H); 6.28 (d, 1H); 6.86 (s, 1H); 6.88 (s, 1H)

83b: δ=0.52 ppm (s, 3H); 0.89 (d, 3H); 2.18 (s, 3H); 3.45 (m, 1H); 3.70 (m, 1H); 4.00 (m, 1H); 4.80 (t, 1H); 5.77 (d, 1H); 6.28 (d, 1H); 6.86 (s, 1H); 6.89 (s, 1H)

Example 21

(7E)-(1R,2S,3R)-24a-(4-Methylthien-2-yl)-1,2,3-trihydroxy-24a-homo-19-nor-9,10-secochola-5,7-dien-24a-one 85

80. 46 mg of alcohol 82 is treated analogously to 25., whereby 41 mg of (7E)-(1R,2S,3R)-24a-(4-methylthien-2-yl)-1,2,3-tris[[(1,1-dimethylethyl)dimethylsilyl]oxy]-24a-homo-19-nor-9,10-secochola-5,7-dien-24a-one 84 accumulates as a colorless foam.

$^1$H-NMR (CDCl$_3$): δ=0.02–0.07 ppm (4×s, 18H); 0.53 (s, 3H); 0.83 (s, 9H); 0.89 (s, 18H); 0.97 (d, 3H); 2.28 (s, 3H); 3.63 (m, 1H); 3.79 (m, 1H); 3.84 (m, 1H); 5.83 (d, 1H); 6.05 (d, 1H); 7.21 (s, 1H); 7.51 (s, 1H)

81. 40 mg of ketone 84 is treated analogously to 26., whereby 18 mg of title compound 85 accumulates as a colorless foam.

$^1$H-NMR (CD$_2$Cl$_2$): δ=0.53 ppm (s, 3H); 0.95 (d, 3H); 2.26 (s, 3H); 3.47 (m, 1H); 3.70 (m, 1H); 4.01 (m, 1H); 5.77 (d, 1H); 6.30 (d, 1H); 7.20 (s, 1H); 7.50 (s, 1H)

Example 22

(7E)-(1R,3R,24aR)-24a-(5-Ethylthien-2-yl)-24a-homo-19-nor-9,10-secochola-5,7-diene-1,3,24a-triol 92a and (7E)-(1R,3R,24aS)-24a-(5-ethylthien-2-yl)-24a-homo-19-nor-9,10-secochola-5,7-diene-1,3,24a-triol 92b 82. 1.19 ml of 2-ethylthiophene is introduced into 20 ml of tetrahydrofuran, and 4.2 ml of n-butyllithium solution (2.5 M in hexane) is added at −78° C. After 30 minutes at this temperature, 770 mg of aldehyde 8 in 5 ml of tetrahydrofuran is added in drops, and it is stirred for 1 more hour. Then, it is quenched with sodium chloride solution, extracted with ethyl acetate, the organic phase is washed with sodium chloride solution and dried on sodium sulfate. The solvent is removed, and the residue is chromatographed on silica gel with ethyl acetate/hexane, whereby 773 mg of [1R-[1α(1R*),3aβ,4α,7aα]]-5-ethyl-α-[4-[octahydro-7a-methyl-4-[(triethylsilyl)oxy]-1H-inden-1-yl]pentyl]thiophene-2-methanol 86 is obtained as a colorless oil.

$^1$H-NMR (CDCl$_3$): δ=0.56 ppm (q, 6H); 0.89 (d, 3H); 0.90 (s, 3H); 0.97 (t, 9H); 1.31 (t, 3H); 2.82 (q, 2H); 4.03 (m, 1H); 4.81 (m, 1H); 6.62 (d, 1H); 6.80 (d, 1H)

83. 763 mg of alcohol 86 is treated analogously to 9., and 745 mg of [1R-[1α(1R*),3aβ,4α,7aα]]-1-(5-ethylthien-2-yl)-5-[octahydro-7a-methyl-4-[(triethyl-silyl)oxy]-1H-inden-1-yl]hexyl-acetate 87 is obtained as a colorless oil.

$^1$H-NMR (CDCl$_3$): δ=0.55 ppm (q, 6H); 0.87/0.88 (d, 3H); 0.90 (s, 3H); 0.95 (t, 9H); 1.30 (t, 3H); 2.07 (s, 3H); 2.82 (q, 2H); 4.03 (m, 1H); 5.97 (t, 1H); 6.62 (d, 1H); 6.87 (d, 1H)

84. 682 mg of acetate 87 is treated analogously to 10., and 287 mg of [1R-[1α(1R*),3aβ,4α,7aα]]-1-[5-(acetyloxy)-5-(5-ethylthien-2-yl)-1-methylpentyl]octahydro-7a-methyl-1H-inden-4-ol 88 is obtained as a colorless oil.

$^1$H-NMR (CDCl$_3$): δ=0.87/0.88 ppm (d, 3H); 0.92 (s, 3H); 1.31 (t, 3H); 2.08 (s, 3H); 2.82 (q, 2H); 4.07 (m, 1H); 5.97 (t, 1H); 6.63 (d, 1H); 6.85 (d, 1H)

85. 142 mg of alcohol 88 is treated analogously to 11., and 123 mg of [1R-[1α(1R*),3aβ,7aα]]-1-[5-(acetyloxy)-5-(5-ethylthien-2-yl)-1-methylpentyl]octahydro-7a-methyl-4H-inden-4-one 89 is obtained as a colorless oil.

$^1$H-NMR (CDCl$_3$): δ=0.62 ppm (s, 3H); 0.92/0.93 (d, 3H); 1.30 (t, 3H); 2.07 (s, 3H); 2.82 (q, 2H); 5.97 (t, 1H); 6.62 (d, 1H); 6.86 (d, 1H)

86. 347 mg of phosphine oxide 13, which was deprotonated with 0.3 ml of n-butyllithium solution (2.5 M in hexane), is reacted with 123 mg of ketone 89 analogously to 12., and 129 mg of (7E)-(1R,3R)-24a-(acetyloxy)-1,3-bis[[(1,1-dimethylethyl)dimethylsilyl]oxy]-24a-(5-ethylthien-2-yl)-24a-homo-19-nor-9,10-secochola-5,7-diene 90 is obtained as a colorless foam.

$^1$H-NMR (CDCl$_3$): δ=0.07 ppm (s, 12H); 0.53 (s, 3H); 0.90 (s, 18H); 0.91 (d, 3H); 1.30 (t, 3H); 2.07 (s, 3H); 2.82

(q, 2H); 4.09 (m, 2H); 5.82 (d, 1H); 5.96 (t, 1H); 6.18 (d, 1H); 6.62 (d, 1H); 6.86 (d, 1H).

87. 129 mg of acetate 90 is reacted analogously to 13., and 98 mg of (7E)-(1R,3R)-1,3-bis[[(1,1-dimethylethyl)dimethylsilyl]-oxy]-24a-(5-ethylthien-2-yl)-24a-homo-19-nor-9,10-secochola-5,7-dien-24a-ol 91 is obtained as a colorless foam.

$^1$H-NMR (CDCl$_3$): δ=0.07 ppm (s, 12H); 0.54 (s, 3H); 0.89 (s, 18H); 0.91 (d, 3H); 1.30 (t, 3H); 2.82 (q, 2H); 4.10 (m, 2H); 4.84 (m, 1H); 5.82 (d, 1H); 6.18 (d, 1H); 6.63 (d, 1H); 6.80 (d, 1H)

88. 98 mg of alcohol 91 is treated analogously to 14., and after the diastereomers (in terms of C-24a) are separated by HPLC, 18 mg of title compound 92a and 19 mg of title compound 92b are obtained as colorless foams.

$^1$H-NMR (CD$_2$Cl$_2$/CD$_3$OD): 92a: δ=0.51 ppm (s, 3H); 0.89 (d, 3H); 1.27 (t, 3H); 2.78 (q, 2H); 3.94 (m, 1H); 4.02 (m, 1H); 4.75 (t, 1H); 5.84 (d, 1H); 6.25 (d, 1H); 6.59 (d, 1H); 6.71 (d, 1H)

92b: δ=0.51 ppm (s, 3H); 0.90 (d, 3H); 1.27 (t, 3H); 2.78 (q, 2H); 3.94 (m, 1H); 4.02 (m, 1H); 4.76 (t, 1H); 5.84 (d, 1H); 6.25 (d, 1H); 6.59 (d, 1H); 6.71 (d, 1H)

Example 23

(7E)-(1R,3R,24aR)-24a-[5-(2-Hydroxyethyl)-4-methylthiazol-2-yl]-24a-homo-19-nor-9,10-secochola-5,7-diene-1,3,24a-54iol 102a and (7E)-(1R,3R,24aS)-24a-[5-(2-hydroxyethyl)-4-methylthiazol-2-yl]-24a-homo-19-nor-9,10-secochola-5,7-diene-1,3,24a-triol 102b 89. 2.09 ml of 5-(2-hydroxyethyl)-4-methylthiazole 93 is introduced into 150 ml of dichloromethane, 7.8 ml of 2,3-dihydropyran and 400 mg of pyridinium-p-toluenesulfonate are added, and it is stirred for 5 days at room temperature. Then, sodium chloride solution is added, extracted with ethyl acetate, the organic phase is washed with sodium bicarbonate solution and sodium chloride solution, dried on sodium sulfate and concentrated by evaporation. The residue is chromatographed on silica gel with ethyl acetate/hexane, whereby 3.8 g of 5-[2-[(tetrahydro-2H-pyran-2-yl)oxy]ethyl]-4-methylthiazole 94 is obtained as a colorless oil.

$^1$H-NMR (CDCl$_3$): δ=1.48–1.90 ppm (m, 6H); 2.41 (s, 3H); 3.05 (t, 2H); 3.48 (m, 1H); 3.56 (dt, 1H); 3.75 (m, 1H); 3.93 (dt, 1H); 4.61 (m, 1H); 8.54 (s, 1H)

90. 2.78 g of thiazole 94 is introduced into 25 ml of tetrahydrofuran, and 4.9 ml of n-butyllithium solution (2.5 M in hexane) is added at −78° C. After 30 minutes at this temperature, 900 mg of aldehyde 8 in 5 ml of tetrahydrofuran is added in drops, and it is stirred for 1 more hour. Then, it is quenched with sodium chloride solution, extracted with ethyl acetate, the organic phase is washed with sodium chloride solution and dried on sodium sulfate. The solvent is removed, and the residue is chromatographed on silica gel with ethyl acetate/hexane, whereby 1.12 g of [1R-[1α(1R*),3aβ,4α,7aα]]-α-[4-[octahydro-7a-methyl-4-[(triethylsilyl)oxy]-1H-inden-1-yl]pentyl]-5-[2-[(tetrahydro-2H-pyran-2-yl)oxy]ethyl]-4-methylthiazol-2-methanol 95 is obtained as a colorless oil.

$^1$H-NMR (CDCl$_3$): δ=0.56 ppm (q, 6H); 0.89 (d, 3H); 0.90 (s, 3H); 0.96 (t, 9H); 2.32 (s, 3H); 3.00 (t, 2H); 3.48 (m, 1H); 3.58 (dt, 1H); 3.75 (m, 1H); 3.90 (dt, 1H); 4.03 (m, 1H); 4.61 (m, 1H); 4.87 (m, 1H); 6.6.2 (d, 1H); 6.80 (d, 1H)

91. 1.12 q of alcohol 95 is treated analogously to 9., and 104 mg of [1R-[1α(1R*),3aβ,4α,7aα]]-5-[octahydro-7a-methyl-4-[(triethylsilyl)oxy]-1H-inden-1-yl]-1-[5-[2-[(tetrahydro-2H-pyran-2-yl)oxy]ethyl]-4-methylthiazol-2-yl]hexyl-acetate 96 is obtained as a colorless oil.

$^1$H-NMR (CDCl$_3$): δ=0.55 ppm (q, 6H); 0.88/0.89 (d, 3H); 0.90 (s, 3H); 0.96 (t, 9H); 2.11 (s, 3H); 2.35 (s, 3H); 3.00 (t, 2H); 3.50(m, 1H); 3.53 (dt, 1H); 3.74 (m, 1H); 3.90 (dt, 1H); 4.02 (m, 1H); 4.61 (m, 1H); 5.97 (t, 1H)

92. 1.04 g of acetate 96 is treated analogously to 10., and 540 mg of [1R-[1α(1R*),3aβ,4α,7aα]]-1-[5-(acetyloxy)-5-[5-[2-[(tetrahydro-2H-pyran-2-yl)oxy]ethyl]-4-methylthiazol-2-yl]-1-methylpentyl]octahydro-7a-methyl-1H-inden-4-ol 97 is obtained as a colorless oil.

$^1$H-NMR (CDCl$_3$): δ=0.88/0.89 ppm (d, 3H); 0.91 (s, 3H); 2.11 (s, 3H); 2.35 (s, 3H); 3.00 (t, 2H); 3.50 (m, 1H); 3.55 (dt, 1H); 3.74 (m, 1H); 3.90 (dt, 1H); 4.07 (m, 1H); 4.61 (m, 1H); 5.97 (t, 1H)

93. 540 mg of alcohol 97 is treated analogously to 11., and 498 mg of [1R-[1α(1R*),3aβ,7aα]]-1-[5-(acetyloxy)-5-[5-[2-[(tetrahydro-2H-pyran-2-yl)oxy]ethyl]-4-methylthiazol-2-yl]-1-methylpentyl]octahydro-7a-methyl-4H-inden-4-one 98 is obtained as a colorless oil.

$^1$H-NMR (CDCl$_3$): δ=0.62 ppm (s, 3H); 0.92/0.93 (d, 3H); 2.13 (s, 3H); 2.37 (s, 3H); 3.00 (t, 2H); 3.49 (m, 1H); 3.54 (dt, 1H); 3.73 (m, 1H); 3.90 (dt, 1H); 4.61 (m, 1H); 5.97 (t, 1H)

94. 656 mg of phosphine oxide 13, which was deprotonated with 0.55 ml of n-butyllithium solution (2.5 M in hexane), is reacted with 300 mg of ketone 98 analogously to 12., and 310 mg of (7E)-(1R,3R)-1,3-bis[[(1,1-dimethylethyl)dimethylsilyl]oxy]-24a-[5-[2-[(tetrahydro-2H-pyran-2-yl)oxy]ethyl]-4-methylthiazol-2-yl]-24a-homo-19-nor-9,10-secochola-5,7-dien-24a-yl-acetate 99 is obtained as a colorless foam.

$^1$H-NMR (CDCl$_3$): δ=0.07 ppm (s, 12H); 0.53 (s, 3H); 0.90 (s, 18H); 0.91 (d, 3H); 2.12 (s, 3H); 2.38 (s, 3H); 3.01 (t, 2H); 3.50 (m, 1H); 3.56 (dt, 1H); 3.75 (m, 1H); 3.90 (dt, 1H); 4.09 (m, 2H); 4.61 (m, 1H); 5.82 (d, 1H); 5.97 (t, 1H); 6.18 (d, 1H)

95. 151 mg of acetate 99 is reacted analogously to 13., and 104 mg of (7E)-(1R,3R)-1,3-bis[[(1,1-dimethylethyl)dimethylsilyl]-oxy]-24a-[5-[2-[(tetrahydro-2H-pyran-2-yl)oxy]ethyl]-4-methylthiazol-2-yl]-24a-homo-19-nor-9,10-secochola-5,7-dien-24a-ol 100 is obtained as a colorless foam.

$^1$H-NMR (CD$_2$Cl$_2$): δ=0.04 ppm (s, 12H); 0.51 (s, 3H); 0.85 (s, 18H); 0.90 (d, 3H); 2.28 (s, 3H); 2.95 (t, 2H); 3.40 (m, 1H); 3.50 (dt, 1H); 3.70 (m, 1H); 3.82 (dt, 1H); 4.07 (m, 2H); 4.80 (m, 1H); 5.80 (d, 1H); 6.17 (d, 1H)

96. 170 mg of THP ether 100 is introduced into 20 ml of dichloromethane, 0.41 ml of dimethyl aluminum chloride solution is added at −25° C., and it is stirred for 1 more hour, whereby the mixture is heated to 0° C. Then, it is quenched with sodium bicarbonate solution, extracted with ethyl acetate, the organic phase is washed with sodium chloride solution, dried on sodium sulfate, and the solvent is removed in a vacuum. The residue is chromatographed on silica gel with ethyl acetate/hexane, whereby 153 mg of (7E)-(1R,3R)-1,3-bis[[(1,1-dimethylethyl)dimethylsilyl]oxy]-24a-[5-(2-hydroxyethyl)-4-methylthiazol-2-yl]-24a-homo-19-nor-9,10-secochola-5,7-dien-24a-ol 101 is obtained as a colorless foam.

$^1$H-NMR (CD$_2$Cl$_2$): δ=0.04 ppm (s, 12H); 0.51 (s, 3H); 0.85 (s, 18H); 0.90 (d, 3H); 2.28 (s, 3H); 2.92 (t, 2H); 3.26 (t, 2H); 4.08 (m, 2H); 4.80 (m, 1H); 5.80 (d, 1H); 6.17 (d, 1H)

97. 113 mg of alcohol 101 is treated analogously to 14., and after the diastereomers (in terms of C-24a) are separated by HPLC, 21 mg of title compound 102a and 24 mg of title compound 102b are obtained as colorless foams.

¹H-NMR (CD₂Cl₂/CD₃OD): 102a: δ=0.50 ppm (s, 3H); 0.88 (d, 3H); 2.27 (s, 3H); 2.88 (t, 2H); 3.68 (d, 2H); 3.92 (m, 1H); 4.00 (m, 1H); 4.74 (m, 1H); 5.82 (d, 1H); 6.24 (d, 1H)

102b: δ=0.50 ppm (s, 3H); 0.89 (d, 3H); 2.28 (s, 3H); 2.88 (t, 2H); 3.68 (d, 2H); 3.92 (m, 1H); 4.00 (m, 1H); 4.75 (dd, 1H); 5.82 (d, 1H); 6.24 (d, 1H)

Example 24

(7E)-(1R,3R)-1,3-Dihydroxy-24a-[5-(2-hydroxyethyl)-4-methylthiazol-2-yl]-24a-homo-19-nor-9,10-secochola-5,7-dien-24a-one 104

98. 70 mg of alcohol 100 is treated analogously to 25., whereby 40 mg of (7E)-(1R,3R)-1,3-bis[[(1,1-dimethylethyl)dimethylsilyl]-oxy]-24a-[5-(2-hydroxyethyl)-4-methylthiazol-2-yl]-24a-homo-19-nor-9,10-secochola-5,7-dien-24a-one 103 accumulates as a colorless foam.

¹H-NMR (CD₂Cl₂): δ=0.04 ppm (s, 12H); 0.51 (s, 3H) 0.84 (s, 18H); 0.93 (d, 3H); 2.37 (s, 3H); 3.01 (t, 2H); 3.40 (m, 1H); 3.53 (dt, 1H); 3.68 (m, 1H); 3.89 (dt, 1H); 4.08 (m, 2H); 4.54 (m, 1H); 5.80 (d, 1H); 6.15 (d, 1H)

99. 40 mg of ketone 103 is treated analogously to 26., whereby 12 mg of title compound 104 accumulates as a colorless foam.

¹H-NMR (CD₂Cl₂): δ=0.52 ppm (s, 3H); 0.95 (d, 3H); 2.41 (s, 3H); 3.01 (t, 2H); 3.80 (t, 2H); 3.95 (m, 1H); 4.05 (m, 1H); 5.82 (d, 1H); 6.25 (d, 1H)

Example 25

(7E)-(1R,3R,24aR)-24a-(Benzothiazol-2-yl)-24a-homo-19-nor-9,10-secochola-5,7-diene-1,3,24a-triol 111a and (7E)-(1R,3R,24aS)-24a-(benzothiazol-2-yl)-24a-homo-19-nor-9,10-secochola-5,7-diene-1,3, 24a-triol 111b 100. 0.85 ml of benzothiazole is introduced into 20 ml of tetrahydrofuran, and 3.1 ml of n-butyllithium solution (2.5 M in hexane) is added at −78° C. After 30 minutes at this temperature, 574 mg of aldehyde 8 in 3 ml of tetrahydrofuran is added in drops, and it is stirred for 1 more hour. Then, it is quenched with sodium chloride solution, extracted with ethyl acetate, the organic phase is washed with sodium chloride solution and dried on sodium sulfate. The solvent is removed, and the residue is chromatographed on silica gel with ethyl acetate/hexane, whereby 751 mg of [1R-[1α(1R*),3aβ,4α,7aα]]-α-[4-[octahydro-7a-methyl-4-[(triethylsilyl)oxy]-1H-inden-1-yl]pentyl]benzothiazol-2-methanol 105 is obtained as a colorless oil.

¹H-NMR (CDCl₃): δ=0.55 ppm (q, 6H); 0.89 (d, 3H); 0.91 (s, 3H); 0.95 (t, 9H); 4.02 (m, 1H); 5.10 (m, 1H); 7.40 (t, 1H); 7.48 (t, 1H); 7.90 (d, 1H); 8.00 (d, 1H)

101. 751 mg of alcohol 105 is treated analogously to 9., and 764 mg of [1R-[1α(1R*),3aβ,4α,7aα]]-1-(benzothiazol-2-yl)-5-[octahydro-7a-methyl-4-[(triethyl-silyl)oxy]-1H-inden-1-yl)hexyl-acetate 106 is obtained as a colorless oil.

¹H-NMR (CDCl₃): δ=0.55 ppm (q, 6H); 0.88/0.89 (d, 3H); 0.90 (s, 3H); 0.96 (t, 9H); 2.20 (s, 3H); 4.02 (m, 1H); 6.15 (t, 1H); 7.40 (t, 1H); 7.49 (t, 1H); 7.90 (d, 1H); 8.03 (d, 1H)

102. 764 mg of acetate 106 is treated analogously to 10., and 310 mg of [1R-[1α(1R*),3aβ,4α,7aα]]-1-5-(acetyloxy)-5-(benzothiazol-2-yl)-1-methylpentyl]octahydro-7a-methyl-1H-inden-4-ol 107 is obtained as a colorless oil.

¹H-NMR (CDCl₃): δ=0.88/0.89 (d, 3H); 0.91 (s, 3H); 2.19 (s, 3H); 4.07 (m, 1H); 6.17 (t, 1H); 7.40 (t, 1H); 7.49 (t, 1H); 7.90 (d, 1H); 8.03 (d, 1H)

103. 310 mg of alcohol 107 is treated analogously to 11., and 277 mg of [1R-[1α(1R*),3aβ,7aα]]-1-[5-(acetyloxy)-5-(benzothiazol-2-yl)-1-methylpentyl]octahydro-7a-methyl-4H-inden-4-one 108 is obtained as a colorless oil.

¹H-NMR (CDCl₃): δ=0.62 ppm (s, 3H); 0.92/0.93 (d, 3H); 2.19 (s, 3H); 6.17 (t, 1H); 7.40 (t, 1H); 7.49 (t, 1H); 7.89 (d, 1H); 8.02 (d, 1H)

104. 736 mg of phosphine oxide 13, which was deprotonated with 0.62 ml of n-butyllithium solution (2.5 M in hexane), is reacted with 277 mg of ketone 108 analogously to 12., and 193 mg of (7E)-(1R,3R)-24a-(acetyloxy)-24a-(2-benzothiazol-2-yl)-1,3-bis[[(1,1-dimethylethyl)dimethylsilyl]oxy]-24a-homo-19-nor-9,10-secochola-5,7-diene 109 is obtained as a colorless foam.

¹H-NMR (CDCl₃): δ=0.07 ppm (s, 12H); 0.53 (s, 3H); 0.90 (s, 18H); 0.91 (d, 3H); 2.19 (s, 3H); 4.08 (m, 2H); 5.82 (d, 1H); 6.18 (d, 1H); 6.18 (m, 1H); 7.38 (t, 1H); 7.49 (t, 1H); 7.88 (d, 1H); 8.02 (d, 1H)

105. 193 mg of acetate 109 is reacted analogously to 13., and 177 mg of (7E)-(1R,3R)-24a-(benzothiazol-2-yl)-1,3-bis[[(1,1-dimethylethyl)dimethylsilyl]oxy]-24a-homo-19-nor-9,10-secochola-5,7-dien-24a-ol 110 is obtained as a colorless foam.

¹H-NMR (CD₂Cl₂): δ=0.04 ppm (s, 12H); 0.51 (s, 3H); 0.86 (s, 18H); 0.92 (d, 3H); 4.06 (m, 2H); 5.04 (m, 1H); 5.80 (d, 1H); 6.16 (d, 1H); 7.33 (t, 1H); 7.43 (t, 1H); 7.87 (d, 1H); 7.92 (d, 1H)

106. 124 mg of alcohol 110 is treated analogously to 14., and after the diastereomers (in terms of C-24a) are separated by HPLC, 23 mg of title compound 111a and 22-mg of title compound 111b are obtained as colorless foams.

¹H-NMR (CD₂Cl₂): 111a: δ=0.50 ppm (s, 3H); 0.90 (d, 3H); 3.95 (m, 1H); 4.02 (m, 1H); 5.07 (m, 1H); 5.82 (d, 1H); 6.24 (d, 1H); 7.36 (t, 1H); 7.46 (t, 1H); 7.90 (d, 1H); 7.93 (d, 1H)

111b: δ=0.51 ppm (s, 3H); 0.91 (d, 3H); 3.95 (m, 1H); 4.02 (m, 1H); 5.06 (m, 1H); 5.82 (d, 1H); 6.24 (d, 1H); 7.36 (t, 1H); 7.46 (t, 1H); 7.90 (d, 1H); 7.93 (d, 1H)

Example 26

(7E)-(1R,3R)-24a-(Benzothiazol-2-yl)-1,3-dihydroxy-24a-homo-19-nor-9,10-secochola-5,7-dien-24a-one 113

107. 53 mg of alcohol 110 is treated analogously to 25., whereby 39 mg of (7E)-(1R,3R)-24a-(benzothiazol-2-yl)-1, 3-bis[[(1,1-dimethylethyl)dimethylsilyl]oxy]-24a-homo-19-nor-9,10-secochola-5,7-dien-24a-one 112 accumulates as a colorless foam.

¹H-NMR (CD₂Cl₂): δ=0.04 ppm (s, 12H); 0.52 (s, 3H); 0.85 (s, 18H); 0.96 (d, 3H); 4.06 (m, 2H); 4.54 (m, 1H); 5.80 (d, 1H); 6.15 (d, 1H); 7.25 (t, 1H); 7.59 (t, 1H); 8.01 (d, 1H); 8.15 (d, 1H)

108. 39 mg of ketone 112 is treated analogously to 26., whereby 20 mg of title compound 113 accumulates as a colorless foam.

¹H-NMR (CD₂Cl₂): δ=0.53 ppm (s, 3H); 0.95 (d, 3H); 3.94 (m, 1H); 4.02 (m, 1H); 5.82 (d, 1H); 6.25 (d, 1H); 7.53 (t, 1H); 7.56 (t, 1H); 7.98 (d, 1H); 8.13 (d, 1H)

Example 27

(7E)-(1R,3R,24aR)-24a-(Benzofuran-2-yl)-24a-homo-19-nor-9,10-secochola-5,7-diene-1,3,24a-triol 120a and (7E)-(1R,3R,24aS)-24a-(benzofuran-2-yl)-24a-homo-19-nor-9,10-secochola-5,7-diene-1,3,24a-triol 120b 109. 1.44 mg of 2,3-benzofuran is introduced into 25 ml of tetrahydrofuran, and 5.2 ml of n-butyllithium solution (2.5 M in hexane) is added at −78° C. After 30-minutes at this temperature, 960 mg of aldehyde 8 in 5 ml of tetrahydrofuran is added in drops, and it is stirred for 1 more hour. Then, it is quenched with sodium chloride solution, extracted with ethyl acetate, the organic phase is washed with sodium chloride solution and dried on sodium sulfate. The solvent is removed, and the residue is chromatographed on silica gel with ethyl acetate/hexane, whereby 1.06 g of [1R-[1α(1R*),3aβ,4α,7aα]]-α-[4-[octahydro-7a-methyl-4-[(triethylsilyl)oxy]-1H-inden-1-yl]pentyl]benzofuran-2-methanol 114 is obtained as a colorless oil.

$^1$H-NMR (CDCl$_3$): δ=0.56 ppm (q, 6H); 0.89 (d, 3H); 0.91 (s, 3H); 0.95 (t, 9H); 4.02 (m, 1H); 4.83 (m, 1H); 7.22 (t, 1H); 7.29 (t, 1H); 7.48 (d, 1H); 7.57 (d, 1H)

110. 1.06 g of alcohol 114 is introduced into 18 ml of dichloromethane, and 0.83 ml of 2,3-dihydropyran and 48 mg of pyridinium-p-toluene sulfonate are added. It is stirred for 1 day at room temperature, and then sodium chloride solution is added. It is extracted with ethyl acetate, the organic phase is washed with sodium chloride solution, dried on sodium sulfate and concentrated by evaporation. The residue is chromatographed on silica gel with ethyl acetate/hexane, whereby 1.11 q of [1R-[1α(1R*),3aβ,4α,7aα]]-1-[5-(benzofuran-2-yl)-1-methyl-5-[(tetrahydro-2H-pyran-2-yl)oxy]pentyl]octahydro-7a-methyl-4-[(triethylsilyl)oxy]-1H-indene 115 is obtained as a colorless oil.

$^1$H-NMR (CDCl$_3$): δ=0.55 ppm (q, 6H); 0.88/0.89 (d, 3H); 0.90 (s, 3H); 0.96 (t, 9H); 3.40 (m, 1H); 3.55 (m, 1H); 4.02 (m, 1H); 4.77 (t, 1H); 6.65 (m, 1H); 7.23 (m, 2H); 7.49 (d, 1H); 7.54 (d, 1H)

111. 1.11 g of silyl ether 115 is introduced into 50 ml of tetrahydrofuran, 1.81 g of tetrabutylammonium fluoride is added, and it is stirred for 1 day at room temperature. Then, sodium chloride solution is added, extracted with ethyl acetate, washed with sodium chloride solution, dried on sodium sulfate and concentrated by evaporation. The residue is chromatographed on silica gel with ethyl acetate/hexane, whereby 760 mg of [1R-[1α(1R*),3aβ,4α,7aα]]-1-[5-(benzofuran-2-yl)-1-methyl-5-[(tetrahydro-2H-pyran-2-yl)oxy]pentyl]octahydro-7a-methyl-1H-inden-4-ol 116 is obtained as a colorless oil.

$^1$H-NMR (CDCl$_3$): δ=0.88/0.89 ppm (d, 3H); 0.91 (s, 3H); 3.40 (m, 1H); 3.55 (m, 1H); 4.04 (m, 1H); 4.60 (m, 1H); 4.78 (t, 1H); 6.65 (m, 1H); 7.25 (m, 2H); 7.48 (d, 1H); 7.55 (d, 1H)

112. 750 mg of alcohol 116 is treated analogously to 11., and 669 mg of [1R-[1α(1R*),3aβ,7aα]]-1-[5-(benzofuran-2-yl)-1-methyl-5-[(tetrahydro-2H-pyran-2-yl)oxy]pentyl]octahydro-7a-methyl-4H-inden-4-one 117 is obtained as a colorless oil.

$^1$H-NMR (CDCl$_3$): δ=0.62 ppm (s, 3H); 0.92/0.93 (d, 3H); 3.40 (m, 1H); 3.54 (m, 1H); 4.60 (m, 1H); 4.80 (t, 1H); 6.65 (m, 1H); 7.25 (m, 2H); 7.49 (d, 1H); 7.55 (d, 1H)

113. 314 mg of THP-ether 117 is introduced into 10 ml of methanol, and 244 mg of pyridinium-p-toluenesulfonate is added. It is stirred for 1 hour at room temperature and then treated with sodium chloride solution. It is extracted with ethyl acetate, the organic phase is washed with sodium bicarbonate solution and sodium chloride solution, dried on sodium sulfate and concentrated by evaporation. The residue is chromatographed on silica gel with ethyl acetate/hexane, whereby 760 mg of [1R-[1α(1R*),3aβ,7aα]]-1-[5-(benzofuran-2-yl)-5-hydroxy-1-methylpentyl]octahydro-7a-methyl-4H-inden-4-one 118 is obtained as a colorless oil.

$^1$H-NMR (CDCl$_3$): δ=0.62 ppm (s, 3H); 0.92/0.93 (d, 3H); 4.81 (m, 1H); 6.61 (s, 1H); 7.22 (t, 1H); 7.28 (t, 1H); 7.47 (d, 1H); 7.54 (d, 1H)

114. 180 mg of alcohol 118 is treated analogously to 9., and 169 mg of [1R-[1α(1R*),3aβ,7aα]]-1-[5-(acetyloxy)-5-(benzofuran-2-yl)-1-methylpentyl]octahydro-7a-methyl-4H-inden-4-one 119 is obtained as a colorless oil.

$^1$H-NMR (CDCl$_3$): δ=0.62 ppm (s, 3H); 0.92/0.93 (d, 3H); 2.10 (s, 3H); 5.97 (m, 1H); 6.69 (s, 1H); 7.23 (t, 1H); 7.30 (t, 1H); 7.50 (d, 1H); 7.55 (d, 1H)

115. 444 mg of phosphine oxide 13, which was deprotonated with 0.37 ml of n-butyllithium solution (2.5 M in hexane), is reacted with 160 mg of ketone 119 analogously to 12., and 189 mg of (7E)-(1R,3R)-24a-(acetyloxy)-24a-(2-benzofuran-2-yl)-1,3-bis[[(1,1-dimethylethyl)dimethylsilyl]oxy]-24a-homo-19-nor-9,10-secochola-5,7-diene 120 is obtained as a colorless foam.

$^1$H-NMR (CDCl$_3$): δ=0.07 ppm (s, 12H); 0.53 (s, 3H); 0.90 (s, 18H); 0.91 (d, 3H); 2.10 (s, 3H); 4.08 (m, 2H); 5.81 (d, 1H); 5.97 (t, 1H); 6.18 (m, 1H); 6.70 (s, 1H); 7.22 (t, 1H); 7.30 (t, 1H); 7.49 (d, 1H); 7.55 (d, 1H)

116. 142 mg of acetate 120 is reacted analogously to 13., and 134 mg of (7E)-(1R,3R)-24a-(benzothiazol-2-yl)-1,3-bis[[(1,1-dimethylethyl)dimethylsilyl]oxy]-24a-homo-19-nor-9,10-secochola-5,7-dien-24a-ol 121 is obtained as a colorless foam.

$^1$H-NMR (CDCl$_3$): δ=0.07 ppm (s, 12H); 0.53 (s, 3H); 0.89 (s, 18H); 0.94 (d, 3H); 4.08 (m, 2H); 4.83 (m, 1H); 5.82 (d, 1H); 6.18 (d, 1H); 6.62 (s, 1H); 7.22 (t, 1H); 7.28 (t, 1H); 7.47 (d, 1H); 7.55 (d, 1H)

117. 134 mg of alcohol 121 is treated analogously to 14., and after the diastereomers (in terms of C-24a) are separated by HPLC, 29 mg of title compound 122a and 26 mg of title compound 122b are obtained as colorless foams.

$^1$H-NMR (CD$_2$Cl$_2$/CD$_3$OD): 122a: δ=0.50 ppm (s, 3H); 0.88 (d, 3H); 3.92 (m, 1H); 4.00 (m, 1H); 4.71 (t, 1H); 5.81 (d, 1H); 6.22 (d, 1H); 6.58 (s, 1H); 7.18 (t, 1H); 7.21 (t, 1H); 7.41 (d, 1H); 7.52 (d, 1H)

122b: δ=0.50 ppm (s, 3H); 0.89 (d, 3H); 3.92 (m, 1H); 4.00 (m, 1H); 4.72 (t, 1H); 5.81 (d, 1H); 6.22 (d, 1H); 6.58 (s, 1H); 7.18 (t, 1H); 7.21 (t, 1H); 7.41 (d, 1H); 7.53 (d, 1H)

Example 28

(7E)-(1R,3R)-24a-(Benzofuran-2-yl)-1,3-dihydroxy-24a-homo-19-nor-9,10-secochola-5,7-dien-24a-one 124

118. 49 mg of alcohol 121 is treated analogously to 25., whereby 39 mg of (7E)-(1R,3R)-24a-(benzofuran-2-yl)-1,3-bis[[(1,1-dimethylethyl)dimethylsilyl]oxy]-24a-homo-19-nor-9,10-secochola-5,7-dien-24a-one 123 accumulates as a colorless foam.

$^1$H-NMR (CD$_2$Cl$_2$): δ=0.04 ppm (s, 12H); 0.52 (s, 3H); 0.85 (s, 18H); 0.97 (d, 3H); 4.06 (m, 2H); 4.54 (m, 1H); 5.81 (d, 1H); 6.16 (d, 1H); 7.29 (t, 1H); 7.46 (t, 1H); 7.47 (s, 1H); 7.59 (d, 1H); 7.72 (d, 1H)

119. 39 mg of ketone 123 is treated analogously to 26., whereby 12 mg of title compound 124 accumulates as a colorless foam.

¹H-NMR (CD₂Cl₂): δ=0.53 ppm (s, 3H); 0.95 (d, 3H); 3.95 (m, 1H); 4.03 (m, 1H); 5.84 (d, 1H); 6.25 (d, 1H); 7.30 (t, 1H); 7.46 (t, 1H); 7.49 (s, 1H); 7.56 (d, 1H); 7.72 (d, 1H)

Example 29

(7E)-(1R,3R,24aR)-24a-(Benzothiophen-2-yl)-24a-homo-19-nor-9,10-secochola-5,7-diene-1,3,24a-triol 131a and (7E)-(1R,3R,24aS)-24a-(benzothiophen-2-yl)-24a-homo-19-nor-9,10-secochola-5,7-diene-1,3, 24a-triol 131b 120. 0.79 ml of 1-benzothiophene is introduced into 12 ml of tetrahydrofuran, and 2.72 ml of n-butyllithium solution (2.5 M in hexane) is added at −78° C. After 30 minutes at this temperature, 500 mg of aldehyde 8 in 3 ml of tetrahydrofuran is added in drops, and it is stirred for 1 more hour. Then, it is quenched with sodium chloride solution, extracted with ethyl acetate, the organic phase is washed with sodium chloride solution and dried on sodium sulfate. The solvent is removed, and the residue is chromatographed on silica gel with ethyl acetate/hexane, whereby 679 mg of [1R-[1α(1R*),3aβ,4α,7aα]]-α-[4-[octahydro-7a-methyl-4-[(triethylsilyl)oxy]-1H-inden-1-yl]pentyl]benzothiophene-2-methanol 125 is obtained as a colorless oil.

¹H-NMR (CDCl₃): δ=0.56 ppm (q, 6H); 0.89 (d, 3H); 0.91 (s, 3H); 0.96 (t, 9H); 4.03 (m, 1H); 5.02 (m, 1H); 7.36 (m, 3H); 7.45 (d, 1H); 7.88 (d, 2H)

121. 670 mg of alcohol 125 is treated analogously to 9., and 699 mg of [1R-[1α(1R*),3aβ,4α,7aα]]-1-(benzothiophen-2-yl)-5-[octahydro-7a-methyl-4-[(triethylsilyl)oxy]-1H-inden-1-yl)hexyl-acetate 126 is obtained as a colorless oil.

¹H-NMR (CDCl₃): δ=0.55 ppm (q, 6H); 0.88/0.89 (d, 3H); 0.90 (s, 3H); 0.95 (t, 9H); 2.10 (s, 3H); 4.02 (m, 1H); 6.10 (t, 1H); 7.33 (m, 3H); 7.75 (d, 1H); 7.81 (d, 1H)

122. 336 mg of acetate 126 is treated analogously to 10., and 221 mg of [1R-[1α(1R*),3aβ,4,7aα]]-1-[5-(acetyloxy)-5-(benzothiophen-2-yl)-1-methylpentyl]octahydro-7a-methyl-1H-inden-4-ol 127 is obtained as a colorless oil.

¹H-NMR (CDCl₃): δ=0.88/0.89 ppm (d, 3H); 0.91/0.92 (s, 3H); 2.10 (s, 3H); 4.07 (m, 1H); 6.10 (t, 1H); 7.33 (m, 3H); 7.74 (d, 1H); 7.81 (d, 1H)

123. 215 mg of alcohol 127 is treated analogously to 11., and 195 mg of [1R-[1α(1R*),3aβ,7aα]]-1-[5-(acetyloxy)-5-(benzothiophen-2-yl)-1-methylpentyl]octahydro-7a-methyl-4H-inden-4-one 128 is obtained as a colorless oil.

¹H-NMR (CDCl₃): δ=0.62 ppm (s, 3H); 0.92/0.93 (d, 3H); 2.10 (s, 3H); 6.10 (t, 1H); 7.35 (m, 3H); 7.73 (d, 1H); 7.82 (d, 1H)

124. 480 mg of phosphine oxide 13., which was deprotonated with 0.4 ml of n-butyllithium solution (2.5 M in hexane), is reacted with 180 mg of ketone 128 analogously to 12., and 266 mg of (7E)-(1R,3R)-24a-(acetyloxy)-24a-(2-benzothiophen-2-yl)-1,3-bis[[(1,1-dimethylethyl)dimethyl-silyl]oxy]-24a-homo-19-nor-9,10-secochola-5,7-diene 129 is obtained as a colorless foam.

¹H-NMR (CDCl₃): δ=0.07 ppm (s, 12H); 0.53 (s, 3H); 0.90 (s, 18H); 0.91 (d, 3H); 2.10 (s, 3H); 4.08 (m, 2H); 5.80 (d, 1H); 6.10 (t, 1H); 6.18 (m, 1H); 7.33 (m, 2H); 7.72 (d, 1H); 7.82 (d, 1H)

125. 260 mg of acetate 129 is reacted analogously to 13., and 228 mg of (7E)-(1R,3R)-24a-(benzothiophen-2-yl)-1,3-bis[[(1,1-dimethylethyl)dimethylsilyl]oxy]-24a-homo-19-nor-9,10-secochola-5,7-dien-24a-ol 130 is obtained as a colorless foam.

¹H-NMR (CDCl₃): δ=0.07 ppm (s, 12H); 0.53 (s, 3H); 0.89 (s, 18H); 0.93 (d, 3H); 4.08 (m, 2H); 5.00 (m, 1H); 5.82 (d, 1H); 6.19 (d, 1H); 7.21 (s, 1H) 7.33 (m, 2H); 7.73 (d, 1H); 7.83 (d, 1H)

126. 172 mg of alcohol 130 is treated analogously to 14., and after the diastereomers (in terms of C-24a) are separated by HPLC, 22 mg of title compound 131a and 24 mg of title compound 131b are obtained as colorless foams.

¹H-NMR (CD₂Cl₂/CD₃OD): 131a: δ=0.50 ppm (s, 3H); 0.88 (d, 3H); 3.92 (m, 1H); 4.00 (m, 1H); 4.90 (t, 1H); 5.81 (d, 1H); 6.22 (d, 1H); 7.16 (s, 1H); 7.26 (t, 1H); 7.28 (t, 1H); 7.68 (d, 1H); 7.77 (d, 1H)

131b: δ=0.50 ppm (s, 3H); 0.89 (d, 3H); 3.92 (m, 1H); 4.00 (m, 1H); 4.91 (t, 1H); 5.81 (d, 1H); 6.22 (d, 1H); 7.16 (s, 1H); 7.26 (t, 1H); 7.27 (t, 1H); 7.68 (d, 1H); 7.77 (d, 1H)

Example 30

(7E)-(1R,3R)-24a-(Benzothiophen-2-yl)-1,3-dihydroxy-24a-homo-19-nor-9,10-secochola-5,7-dien-24a-one 133

127. 50 mg of alcohol 130 is treated analogously to 25., whereby 38 mg of (7E)-(1R,3R)-24a-(benzothiophen-2-yl)-1,3-bis[[(1,1-dimethylethyl)dimethylsilyl]oxy]-24a-homo-19-nor-9,10-secochola-5,7-dien-24a-one 132 accumulates as a colorless foam.

¹H-NMR (CD₂Cl₂): δ=0.04 ppm (s, 12H); 0.52 (s, 3H); 0.85 (s, 18H); 0.96 (d, 3H); 4.05 (m, 2H); 5.82 (d, 1H); 6.16 (d, 1H); 7.41 (t, 1H); 7.46 (t, 1H); 7.88 (d, 1H); 7.91 (d, 1H); 7.95 (s, 1H)

128. 38 mg of ketone 132 is treated analogously to 26., whereby 21 mg of title compound 133 accumulates as a colorless foam.

¹H-NMR (CD₂Cl₂): δ=0.53 ppm (s, 3H); 0.97 (d, 3H); 3.96 (m, 1H); 4.03 (m, 1H); 5.84 (d, 1H); 6.26 (d, 1H); 7.39 (t, 1H); 7.46 (t, 1H); 7.88 (d, 1H); 7.90 (d, 1H); 7.97 (s, 1H)

Example 31

(7E)-(R,3R,24aR)-24a-(1-Methylbenzimidazol-2-yl)-19-nor-9,10-secochola-5,7-diene-1,3,24a-triol 140a and (7E)-(1R,3R,24aS)-24a-(1-methylbenzimidazol-2-yl)-19-nor-9,10-secochola-5,7-diene-1,3, 24a-triol 140b 129. 899 mg of 1-methylbenzimidazole is introduced into 12 ml of tetrahydrofuran, and 2.72 ml of n-butyllithium solution (2.5 M in hexane) is added at −78° C. After 30 minutes at this temperature, 500 mg of aldehyde 8 in 3 ml of tetrahydrofuran is added in drops, and it is stirred for 1 more hour. Then, it is quenched with sodium chloride solution, extracted with ethyl acetate, the organic phase is washed with sodium chloride solution and dried on sodium sulfate. The solvent is removed, and the residue is chromatographed on silica gel with ethyl acetate/hexane, whereby 487 mg of [1R-[1α(1R*),3aβ,4α,7a]]-α-[4-[octahydro-7a-methyl-4-[(triethylsilyl)oxy]-1H-inden-1-yl] pentyl]-1-methylbenzimidazole-2-methanol 134 is obtained as a colorless oil.

¹H-NMR (CDCl₃): δ=0.56 ppm (q, 6H); 0.89 (d, 3H); 0.91 (s, 3H); 0.96 (t, 9H); 3.78 (s, 3H); 4.02 (m, 1H); 4.93 (m, 1H); 7.25 (m, 3H); 7.71 (d, 1H)

130. 480 mg of alcohol 134 is treated analogously to 9., and 382 mg of [1R-[1α(1R*),3aβ,4α,7aα]]-5-octahydro-7a- methyl-4-[(triethylsilyl)oxy]-1H-inden-1-yl]-1-(1-methyl-benzimidazol-2-yl)hexyl-acetate 135 is obtained as a colorless oil.

¹H-NMR (CDCl₃): δ=0.56 ppm (q, 6H); 0.88/0.89 (d, 3H); 0.90 (s, 3H); 0.95 (t, 9H); 2.11 (s, 3H); 3.87 (s, 3H); 4.02 (m, 1H); 6.02 (t, 1H); 7.32 (m, 3H); 7.80 (d, 1H)

131. 375 mg of acetate 135 is treated analogously to 10., and 259 mg of [1R-[1α(1R*),3aβ,4α,7aα]]-1-[5-(acetyloxy)-1-methyl-5-(1-methylbenzimidazol-2-yl)pentyl]octahydro-7a-methyl-1H-inden-4-ol 136 is obtained as a colorless oil.

¹H-NMR (CDCl₃): δ=0.88/0.89 ppm (d, 3H); 0.91/0.92 (s, 3H); 2.11 (s, 3H); 3.88 (s, 3H); 4.07 (m, 1H); 6.03 (t, 1H); 7.32 (m, 3H); 7.79 (d, 1H)

132. 250 mg of alcohol 136 is treated analogously to 11., and 118 mg of [1R-[1α(1R*),3aβ,7aα]]-1-[5-(acetyloxy)-1-methyl-5-(1-methylbenzimidazol-2-yl)pentyl]octahydro-7a-methyl-4H-inden-4-one 137 is obtained as a colorless oil.

¹H-NMR (CDCl₃): δ=0.62/0.63 ppm (s, 3H); 0.92/0.93 (d, 3H); 2.14 (s, 3H); 3.88 (e, 3H); 6.03 (t, 1H); 7.32 (m, 3H); 7.80 (d, 1H)

133. 317 mg of phosphine oxide 13, which was deprotonated with 0.27 ml of n-butyllithium solution (2.5 M in hexane), is reacted with 118 mg of ketone 137 analogously to 12., and 208 mg of (7E)-(1R,3R)-24a-(acetyloxy)-1,3-bis[[(1,1-dimethylethyl)dimethylsilyl]oxy]-24a-(1-methylbenzimidazol-2-yl)-24a-homo-19-nor-9,10-secochola-5,7-diene 138 is obtained as a colorless foam.

¹H-NMR (CDCl₃): δ=0.07 ppm (s, 12H); 0.52 (s, 3H); 0.90 (s, 18H); 0.91 (d, 3H); 2.10 (s, 3H); 3.85 (s, 3H); 4.08 (m, 2H); 5.80 (d, 1H); 6.02 (t, 1H); 6.16 (d, 1H); 7.33 (m, 3H); 7.78 (d, 1H)

134. 218 mg of acetate 138 is reacted analogously to 13., and 167 mg of (7E)-(1R,3R)-1,3-bis[[dimethyl(1,1-dimethylethyl)silyl]oxy]-24a-(1-methylbenzimidazol-2-yl)-24a-homo-19-nor-9,10-secochola-5,7-dien-24a-ol 139 is obtained as a colorless foam.

¹H-NMR (CD₂Cl₂): δ=0.04 ppm (s, 12H); 0.50 (s, 3H); 0.85 (s, 18H); 0.90 (d, 3H); 3.73 (s, 3H); 4.06 (m, 2H); 4.89 (m, 1H); 5.80 (d, 1H); 6.15 (d, 1H); 7.22 (m, 3H); 7.60 (m, 1H)

135. 115 mg of alcohol 139 is treated analogously to 14., and after the diastereomers (in terms of C-24a) are separated by HPLC, 23 mg of title compound 140a and 22 mg of title compound 140b are obtained as colorless foams.

¹H-NMR (CD₂Cl₂): 140a: δ=0.50 ppm (s, 3H); 0.88 (d, 3H); 3.72 (s, 3H); 3.96 (m, 1H); 4.02 (m, 1H); 4.88 (t, 1H); 5.82 (d, 1H); 6.23 (d, 1H); 7.23 (m, 3H); 7.62 (d, 1H)

140b: δ=0.50 ppm (s, 3H); 0.89 (d, 3H); 3.72 (s, 3H); 3.96 (m, 1H); 4.02 (m, 1H); 4.89 (t, 1H); 5.82 (d, 1H); 6.23 (d, 1H); 7.23 (m, 3H); 7.62 (d, 1H)

Example 32

(7E)-(1R,3R)-1,3-Dihydroxy-24a-(1-methylbenzimidazol-2-yl)-24a-homo-19-nor-9,10-secochola-5,7-dien-24a-one 142

136. 45 mg of alcohol 139 is treated analogously to 25., whereby 26 mg of (7E)-(1R,3R)-1,3-bis[[(1,1-dimethylethyl)dimethylsilyl]-oxy]-24a-(1-methylbenzimidazol-2-yl)-24a-homo-19-nor-9,10-secochola-5,7-dien-24a-one 141 accumulates as a colorless foam.

¹H-NMR (CD₂Cl₂): δ=0.04 ppm (s, 12H); 0.52 (s, 3H); 0.86 (s, 18H); 0.97 (d, 3H); 3.81 (s, 3H); 4.07 (m, 2H); 5.82 (d, 1H); 6.16 (d, 1H); 7.32 (t, 1H); 7.43 (m, 2H); 7.80 (d, 1H)

137. 26 mg of ketone 141 is treated analogously to 26., whereby 8 mg of title compound 142 accumulates as a colorless foam.

¹H-NMR (CD₂Cl₂): δ=0.53 ppm (s, 3H); 0.97 (d, 3H); 3.82 (s, 3H); 3.96 (m, 1H); 4.03 (m, 1H); 4.05 (s, 3H); 5.84 (d, 1H); 6.26 (d, 1H); 7.31 (t, 1H); 7.43 (m, 2H); 7.80 (d, 1H)

Example 33

(7E)-(1R,3R)-1-(1,3-Dihydroxy-24a-homo-19-nor-9,10-secochola-5,7-dien-24a-yl)-3-[(4-methoxyphenyl)methoxy]-1H-pyrazole-4-carboxylic acid ethyl ester 153

138. 10.1 ml of ethoxymethylene malonic acid diethyl ester 143 and 3.3 ml of hydrazine are introduced into 100 ml of ethanol and heated to boiling for 1 hour. After cooling, sodium chloride solution is added, extracted with ethyl acetate, the organic phase is washed with sodium chloride solution, dried on sodium sulfate, and the solvent is removed. The residue is chromatographed on silica gel with ethyl acetate/hexane, whereby 11.2 g of ethoxymethylene malonic acid-ethyl ester hydrazide 144 is obtained as a colorless oil.

¹H-NMR (CDCl₃/CD₃OD): δ=1.25 ppm (t, 3H); 1.29 (t, 3H); 3.78 (sbr, 1H); 4.12 (q, 2H); 4.23 (q, 2H); 8.18 (s, 1H)

139. 11.2 g of hydrazide 144 is treated with 30 ml of aqueous sodium hydroxide solution (25%) and stirred for 1 hour at room temperature. Then, it is neutralized with dilute hydrochloric acid, extracted with ethyl acetate, the organic phase is washed with sodium chloride solution, dried on sodium sulfate and concentrated by evaporation. The residue is chromatographed on silica gel with ethyl acetate/hexane, whereby 2.6 g of 3-hydroxypyrazole-4-carboxylic acid ethyl ester 145 is obtained as a colorless oil.

¹H-NMR (CDCl₃/CD₃OD): δ=1.25 ppm (t, 3H); 4.20 (q, 2H); 4.25 (sbr, 1H); 7.63 (s, 1H)

140. 516 mg of sodium hydride (80% suspension) is introduced into 10 ml of tetrahydrofuran/dimethylformamide (1:1), and pyrazole 145 in 1 ml of tetrahydrofuran/dimethylformamide (1:1) is added in drops. It is stirred for 10 more minutes, and then 2.3 ml of p-methoxybenzyl bromide is added. It is heated to boiling for 4 hours, and then after cooling, sodium chloride solution is added, extracted with ethyl acetate, the organic phase is washed with sodium chloride solution, dried on sodium sulfate, and the solvent is removed. The residue is chromatographed on silica gel with ethyl acetate/hexane, whereby 1.6 g of 3-hydroxy-1-[(4-methylphenyl)methyl]pyrazole-4-carboxylic acid ester 146 and 600 mg of 3-[[(4-methoxyphenyl)methyl]oxy]pyrazole-4-carboxylic acid ethyl ester 147 are obtained in succession as colorless oils.

¹H-NMR (CDCl₃): 146: δ=1.27 ppm (t, 3H); 3.80 (s, 3H); 4.22 (q, 2H); 5.04 (s, 2H); 7.18 (d, 2H); 7.41 (d, 2H); 7.60 (s, 1H)

147: δ=1.30 ppm (t, 3H); 3.80 (s, 3H); 4.28 (q, 2H); 5.30 (s, 2H); 6.89 (d, 2H); 7.42 (d, 2H); 7.88 (s, 1H)

141. 540 mg of alcohol 7 is introduced into 30 ml of dichloromethane, and 0.4 ml of triethylamine and 0.24 ml of methanesulfonyl chloride are added at 0° C. It is stirred for 1 hour at 0° C., then sodium chloride solution is added, extracted with dichloromethane, the organic phase is washed with sodium chloride solution, dried on sodium sulfate, and the solvent is removed, whereby 510 mg of [1R-[1α(1R*),3aβ,4α,7aα]]-5-[octahydro-7a-methyl-4-[(triethylsilyl)oxy]-1H-inden-1-yl]hexyl(methylsulfonate) 148 accumulates as a yellowish oil, which is further reacted in crude form.

142. 36 mg of sodium hydride (80% suspension) is introduced into 10 ml of dimethylformamide, and 240 mg of mesylate 148 and 88 mg of sodium iodide are added at 0° C. After 30 minutes, it is added to benzyl ether 147 in 2 ml of dimethylformamide, and stirring is continued overnight at room temperature. Then, it is quenched with sodium chloride solution, extracted with ethyl acetate, washed with sodium chloride solution, dried on sodium sulfate, and the solvent is removed. The residue is chromatographed on silica gel with ethyl acetate/hexane, whereby 580 mg of [1R-[1α(1R*),3aβ,4α,7aα]]-1-[5-[octahydro-7a-methyl-4-[(triethylsilyl)oxy]-1H-inden-1-yl]hexyl]-3-[(4-methoxyphenyl)methoxy]-1H-pyrazole-4-carboxylic acid ethyl ester 149 is obtained as a colorless oil.

$^1$H-NMR (CDCl$_3$): δ=0.55 ppm (q, 6H); 0.88/0.89 (d, 3H); 0.90 (s, 3H); 0.96 (t, 9H); 1.33 (t, 3H); 3.80 (s, 3H); 3.92 (t, 2H); 4.03 (m, 1H); 4.24-(q, 2H); 5.22 (s, 2H); 6.90 (d, 2H); 7.42 (d, 2H); 7.69 (s, 1H)

143. 500 mg of silyl ether 149 is introduced into 50 ml of tetrahydrofuran, and 262 mg of tetrabutylammonium fluoride (hydrate) is added to it. It is stirred for 24 hours at room temperature and then diluted with sodium chloride solution. It is extracted with ethyl acetate, the organic phase is washed with sodium chloride solution, dried on sodium sulfate, and the solvent is removed. The residue is chromatographed on silica gel with ethyl acetate/hexane, whereby 183 mg of [1R-[1α(1R*),3aβ,4α,7aα]]-1-[5-(octahydro-4-hydroxy-7a-methyl-1H-inden-1-yl]hexyl]-3-[(4-methoxyphenyl)methoxy]-1H-pyrazole-4-carboxylic acid ethyl ester 150 is obtained as a colorless oil.

$^1$H-NMR (CD$_2$Cl$_2$): δ=0.88 ppm (d, 3H); 0.91 (s, 3H); 1.28 (t, 3H); 3.78 (s, 3H); 3.90 (t, 2H); 4.03 (m, 1H); 4.22 (q, 2H); 5.18 (s, 2H); 6.88 (d, 2H); 7.38 (d, 2H); 7.67 (s, 1H)

144. 180 mg of alcohol 150 is treated analogously to 11., and 110 mg of [1R-[1α(1R*),3aβ,7aα]]-1-[5-(octahydro-7a-methyl-4-oxo-1H-inden-1-yl]hexyl]-3-[(4-methoxyphenyl)-methoxy]-1H-pyrazole-4-carboxylic acid ethyl ester 151 is obtained as a colorless oil.

$^1$H-NMR (CD$_2$Cl$_2$) δ=0.62 ppm (s, 3H); 0.97 (d, 3H); 1.28 (t, 3H); 3.80 (s, 3H); 3.91 (t, 2H); 4.18 (q, 2H); 5.20 (s, 2H); 6.88 (d, 2H); 7.39 (d, 2H); 7.69 (s, 1H)

145. 137 mg of phosphine oxide 13, which was deprotonated with 0.12 ml of n-butyllithium solution (2.5 M in hexane), is reacted with 60 mg of ketone 151 analogously to 12., and 76 mg of (7E)-(1R,3R)-1-[1,3-bis[[(1,1-dimethylethyl)dimethylsilyl]oxy]-24a-homo-19-nor-9,10-secochola-5,7-dien-24a-yl]-3-[(4-methoxyphenyl)methoxy]-1H-pyrazole-4-carboxylic acid ester 152 is obtained as a colorless foam.

$^1$H-NMR (CD$_2$Cl$_2$): δ=0.04 ppm (s, 12H); 0.50 (s, 3H); 0.85 (s, 18H); 0.91 (d, 3H); 1.28 (t, 3H); 3.77 (s, 3H); 3.88 (t, 2H); 4.04 (m, 2H); 4.18 (q, 2H); 5.17 (s, 2H); 5.79 (d, 1H); 6.14 (d, 1H); 6.88 (d, 2H); 7.38 (d, 2H); 7.65 (s, 1H)

146. 20 mg of silyl ether 152 is reacted analogously to 14., and after chromatographic purification with ethyl acetate/hexane on silica gel, 8 mg of title compound 153 is obtained as a colorless foam.

$^1$H-NMR (CD$_2$Cl$_2$) δ=0.50 ppm (s, 3H); 0.88 (d, 3H); 1.24 (t, 3H); 3.73 (s, 3H); 3.88 (t, 2H); 3.98 (m, 1H); 4.02 (m, 1H); 4.18 (q, 2H); 5.15 (s, 2H); 5.80 (d, 1H); 6.23 (d, 1H); 6.86 (d, 2H); 7.358 (d, 2H); 7.64 (s, 1H)

Example 34

(7E)-(1R,3R)-1-(1,3-Dihydroxy-24a-homo-19-nor-9, 10-secochola-5,7-dien-24a-yl)-3-hydroxy-1H-pyrazole-4-carboxylic acid ethyl ester 157

147. 110 mg of ketone 151 is introduced into 5 ml of ethanol, 40 mg of palladium/carbon is added, and it is hydrogenated until hydrogen is no longer taken up. The catalyst is filtered off, then the organic phase is removed, and the residue is chromatographed with ethyl acetate/hexane on silica gel, whereby 90 mg of [1R-[1α(1R*),3aβ,7aα]]-1-[5-[octahydro-7a-methyl-4-oxo-1H-inden-1-yl]hexyl]-3-hydroxy-1H-pyrazole-4-carboxylic acid ethyl ester 154 accumulates as a colorless oil.

$^1$H-NMR (CD$_2$Cl$_2$): δ=0.58 ppm (s, 3H); 0.90 (d, 3H); 1.30 (t, 3H); 3.90 (t, 2H); 4.28 (q, 2H); 7.57 (s, 1H)

148. 90 mg of alcohol 154 is introduced into 3 ml of dimethylformamide, 0.06 ml of triethylamine and 0.42 ml of t-butyldimethylsilyl chloride (1 M in hexane) are added, and it is stirred for 2 hours at room temperature. Then, it is diluted with sodium chloride solution, extracted with ethyl acetate, the organic phase is washed with sodium chloride solution and dried on sodium sulfate. The solvent is removed, and the residue is chromatographed on silica gel with ethyl acetate/hexane, whereby 111 mg of [1R-[1α(R*), 3aβ,7aα]]-1-[5-(octahydro-7a-methyl-4-oxo-1H-inden-1-yl]hexyl]-3-[[(1,1-dimethylethyl)dimethylsilyl]oxy]-1H-pyrazole-4-carboxylic acid-ethyl ester 155 is obtained as a colorless oil.

$^1$H-NMR (CD$_2$Cl$_2$): δ=0.23 ppm (s, 6H); 0.56 (s, 3H); 0.90 (d, 3H); 0.99 (s, 9H); 1.26 (t, 3H); 3.84 (t, 2H); 4.20 (q, 2H); 7.64 (s, 1H)

149. 171 mg of phosphine oxide 13, which was deprotonated with 0.15 ml of n-butyllithium solution (2.5 M in hexane), is reacted with 77 mg of ketone 155 analogously to 12., and 41 mg of (7E)-(1R,3R)-1-[1,3-bis[[(1,1-dimethylethyl)dimethylsilyl]oxy]-24a-homo-19-nor-9,10-secochola-5,7-dien-24a-yl)-3-([[1,1-dimethylethyl)dimethylsilyl]oxy]-1H-pyrazole-4-carboxylic acid ethyl ester 156 is obtained as a colorless foam.

$^1$H-NMR (CDCl$_3$): δ=0.07 ppm (s, 12H); 0.29 (s, 6H); 0.53 (s, 3H); 0.91 (s, 18H); 0.92 (d, 3H); 1.02 (s, 9H); 1.32 (t, 3H); 3.90 (t, 2H); 4.09 (m, 2H); 4.27 (q, 2H); 5.82 (d, 1H); 6.18 (d, 1H); 7.65 (s, 1H)

150. 41 mg of silyl ether 156 is reacted analogously to 14., and after chromatographic purification with ethyl acetate/hexane on silica gel, 19 mg of title compound 157 is obtained as a colorless foam.

$^1$H-NMR (CD$_2$Cl$_2$/CD$_3$OD): δ=0.50 ppm (s, 3H); 0.83 (d, 3H); 1.27 (t, 3H); 3.83 (t, 2H); 3.92 (m, 1H); 3.99 (m, 1H); 4.23 (q, 2H); 5.82 (d, 1H);-6.21 (d, 1H); 7.57 (s, 1H)

Example 35

(7E)-(1R,3R,24aR)-24a-(4-Methylphenyl)-24a-homo-19-nor-9,10-secochola-5,7-diene-1,3,24a-triol 164a and (7E)-(1R,3R,24aS)-24a-(4-methylphenyl)-24a-homo-19-nor-9,10-secochola-5,7-diene-1,3,24a-triol 164b 151. 0.84 ml of 4-bromotoluene is introduced into 18 ml of tetrahydrofuran, and 2.72 ml of n-butyllithium solution (2.5 M in hexane) is added at −78° C. After 30 minutes at this temperature, 500 mg of aldehyde 8 in 3 ml of tetrahydrofuran is added in drops, and it is stirred for 1 more hour. Then, it is quenched with sodium chloride solution, extracted with ethyl acetate, the organic phase is washed with sodium chloride solution and dried on sodium sulfate. The solvent is removed, and the residue is chromatographed on silica gel with ethyl acetate/hexane, whereby 381 mg of [1R-[1α(1R*),3aβ,4α,7aα]]-α-[4-[octahydro-7a-methyl-4-[(triethylsilyl)oxy]-1H-inden-1-yl]pentyl]-4-methylphenyl-methanol 158 is obtained as a colorless oil.

$^1$H-NMR (CDCl$_3$): δ=0.56 ppm (q, 6H); 0.89 (d, 3H); 0.91 (s, 3H); 0.95 (t, 9H); 2.33 (s, 3H); 4.02 (m, 1H); 4.62 (m, 1H); 7.13 (d, 2H); 7.23 (d, 2H)

152. 315 mg of alcohol 158 is treated analogously to 9., and 302 mg of [1R-[1α(1R*),3aβ,4α,7aα]]-5-[octahydro- 7a-methyl-4-[(triethylsilyl)oxy]-1H-inden-1-yl]-1-(4-methylphenyl)hexyl-acetate 159 is obtained as a colorless oil.

$^1$H-NMR (CDCl$_3$): δ=0.56 ppm (q, 6H); 0.88/0.89 (d, 3H); 0.90 (s, 3H); 0.95 (t, 9H); 2.05 (s, 3H); 2.35 (s, 3H); 4.02 (m, 1H); 5.70 (m, 1H); 7.14 (d, 2H); 7.22 (d, 2H)

153. 300 mg of acetate 159 is treated analogously to 10., and 228 mg of [1R-[1α(1R*),3aβ,4α,7aα]]-1-[5-(acetyloxy)-1-methyl-5-(4-methylphenyl)pentyl]octahydro-7a-methyl-1H-inden-4-ol 160 is obtained as a colorless oil.

$^1$H-NMR (CDCl$_3$): δ=0.87/0.88 ppm (d, 3H); 0.90/0.91 (s, 3H); 2.07 (s, 3H); 2.35 (s, 3H); 4.08 (m, 1H); 5.70 (m, 1H); 7.15 (d, 2H); 7.22 (d, 2H)

154. 227 mg of alcohol 160 is treated analogously to 11., and 185 mg of [1R-[1α(1R*),3aβ,7aα]]-1-[5-(acetyloxy)-1-methyl-5-(4-methylphenyl)pentyl]octahydro-7a-methyl-4H-inden-4-one 161 is obtained as a colorless oil.

$^1$H-NMR (CDCl$_3$): δ=0.62/0.63 ppm (s, 3H); 0.92/0.93 (d, 3H); 2.05 (s, 3H); 2.35 (s, 3H); 5.69 (m, 1H); 7.12 (d, 2H); 7.21 (d, 2H)

155. 267 mg of phosphine oxide 13, which was deprotonated with 0.23 ml of n-butyllithium solution (2.5 M in hexane), is reacted with 90 mg of ketone 161 analogously to 12., and 163 mg of (7E)-(1R,3R)-24a-(acetyloxy)-1,3-bis[[(1,1-dimethylethyl)dimethylsilyl]oxy]-24a-(4-methylphenyl)-24a-homo-19-nor-9,10-secochola-5,7-diene 162 is obtained as a colorless foam.

$^1$H-NMR (CDCl$_3$): δ=0.07 ppm (s, 12H); 0.52/0.53 (s, 3H); 0.90 (s, 18H); 0.91 (d, 3H); 2.07 (s, 3H); 2.35 (s, 3H); 4.08 (m, 2H); 5.70 (m, 1H); 5.80 (d, 1H); 6.18 (d, 1H); 7.15 (d, 2H); 7.22 (d, 2H)

156. 162 mg of acetate 162 is reacted analogously to 13., and 147 mg of (7E)-(1R,3R)-1,3-bis[[(1,1-dimethylethyl)dimethylsilyl]oxy]-24a-(4-methylphenyl)-24a-homo-19-nor-9,10-secochola-5,7-dien-24a-ol 163 is obtained as a colorless foam.

$^1$H-NMR (CDCl$_3$): δ=0.04 ppm (s, 12H); 0.52/0.53 (s, 3H); 0.88 (s, 18H); 0.89 (d, 3H); 2.25 (s, 3H); 4.08 (m, 2H); 4.63 (m, 1H); 5.82 (d, 1H); 6.18 (d, 1H); 7.17 (d, 2H); 7.25 (d, 2H)

157. 115 mg of alcohol 163 is treated analogously to 14., and after the diastereomers (in terms of C-24a) are separated by HPLC, 27 mg of title compound 164a and 30 mg of title compound 164b are obtained as colorless foams.

$^1$H-NMR (CD$_2$Cl$_2$/CD$_3$OD): 164a: δ=0.48 ppm (s, 3H); 0.86 (d, 3H); 2.28 (s, 3H); 3.91 (m, 1H); 3.98 (m, 1H); 4.51 (t, 1H); 5.80 (d, 1H); 6.21 (d, 1H); 7.10 (d, 2H); 7.17 (d, 2H)

164b: δ=0.49 ppm (s, 3H); 0.86 (d, 3H); 2.28 (s, 3H); 3.91(m, 1H); 3.98 (m, 1H); 4.52 (t, 1H); 5.80 (d, 1H); 6.22 (d, 1H); 7.10 (d, 2H); 7.17 (d, 2H)

Example 36

(7E)-(1R,3R)-1,3-Dihydroxy-24a-(4-methylphenyl)-24a-homo-19-nor-9,10-secochola-5,7-dien-24a-one 166

158. 31 mg of alcohol 163 is treated analogously to 25., whereby 19 mg of (7E)-(1R,3R)-1,3-bis[[(1,1-dimethylethyl)dimethylsilyl]-oxy]-24a-(4-methylphenyl)-24a-homo-19-nor-9,10-secochola-5,7-dien-24a-one 165 accumulates as a colorless foam.

$^1$H-NMR (CD$_2$Cl$_2$): δ=0.04 ppm (s, 12H); 0.52 (s, 3H); 0.86 (s, 18H); 0.93 (d, 3H); 2.38 (s, 3H); 4.06 (m, 2H); 5.80 (d, 1H); 6.15 (d, 1H); 7.22 (d, 2H); 7.80 (d, 2H)

159. 18 mg of ketone 165 is treated analogously to 26., whereby 9 mg of title compound 166 accumulates as a colorless foam.

$^1$H-NMR (CD$_2$Cl$_2$): δ=0.53 ppm (s, 3H); 0.95 (d, 3H); 2.38 (s, 3H); 3.96 (m, 1H); 4.03 (m, 1H); 5.84 (d, 1H); 6.26 (d, 1H); 7.26 (d, 2H); 7.84(d, 2H)

Example 37

(7E)-(1R,2R,3R,24aR)-24a-(4-Methylphenyl)-24a-homo-19-nor-9,10-secochola-5,7-diene-1,2,3,24a-tetrol 169a and (7E)-(1R,2S,3R,24aS)-24a-(4-methylphenyl)-24a-homo-19-nor-9,10-secochola-5,7-diene-1,2,3,24a-tetrol 169b 160. 327 mg of [2-[[(3S-(3R,4S,5R)]-3,4,5-tris[[(1,1-dimethylethyl)dimethylsilyl]oxy]cyclo-hexylidene]ethyl]diphenylphosphine oxide 61b [H. F. DeLuca et al. J. Med. Chem. 37, 3730 (1994)], which was deprotonated with 0.22 ml of n-butyllithium solution, is reacted with 90 mg of ketone 161 analogously to 58., and 118 mg of (7E)-(1R,2R,3R)-24a-(acetyloxy)-1,2,3-tris[[(1,1-dimethylethyl)dimethylsilyl]oxy]-24a-(4-methylphenyl)-24a-homo-19-nor-9,10-secochola-5,7-diene 167 is obtained as a colorless foam.

$^1$H-NMR (CDCl$_3$): δ=0.03–0.08 ppm (4×s, 18H); 0.52 (s, 3H); 0.86 (s, 9H); 0.90 (s, 18H); 0.91 (d, 3H); 2.07 (s, 3H); 2.35 (s, 3H); 3.65 (m, 1H); 3.85 (m, 1H); 3.96 (m, 1H); 5.69 (m, 1H); 5.80 (d, 1H); 6.18 (d, 1H); 7.15 (d, 2H); 7.22 (d, 2H)

161. 117 mg of (7E)-(1R,2R,3R)-1,2,3-tris[[(1,1-dimethylethyl)dimethylsilyl]oxy]-24a-(4-methylphenyl)-24a-homo-19-nor-9,10-secochola-5,7-dien-24a-ol 167 is reacted analogously to 13., and 109 mg of 168 is obtained as a colorless foam.

$^1$H-NMR (CDCl$_3$): δ=0.03–0.08 ppm (4×s, 18H); 0.52 (s, 3H); 0.85 (s, 9H); 0.90 (s, 18H); 0.91 (d, 3H); 2.35 (s, 3H); 3.65 (m, 1H); 3.84 (m, 1H); 3.95 (m, 1H); 4.63 (m, 1H); 5.80 (d, 1H); 6.17 (d, 1H); 7.18 (d, 2H); 7.24 (d, 2H)

162. 108 mg of alcohol 168 is treated analogously to 14., and after the diastereomers (in terms of C-24a) are separated by HPLC, 12 mg of title compound 169a and 16 mg of title compound 169b are obtained as colorless foams.

$^1$H-NMR (CD$_2$Cl$_2$): 169a: δ=0.51 ppm (s, 3H); 0.89 (d, 3H); 2.29 (s, 3H); 3.45 (m, 1H); 3.60 (m, 1H); 4.00 (m, 1H); 4.59 (m, 1H); 5.81 (d, 1H); 6.22 (d, 1H); 7.11 (d, 2H); 7.20 (d, 2H)

169b: δ=0.50 ppm (s, 3H); 0.88 (d, 3H); 2.29 (s, 3H); 3.45 (m, 1H); 3.60 (m, 1H); 4.00 (m, 1H); 4.60 (t, 1H); 5.81 (d, 1H); 6.22 (d, 1H); 7.11 (d, 2H); 7.20 (d, 2H)

Example 38

(7E)-(1R,3R,24aR)-24a-(4-Trifluoromethylphenyl)-19-nor-9,10-secochola-5,7-diene-1,3,24a-triol 176a and (7E)-(1R,3R,24aS)-24a-(4-trifluoromethylphenyl)-19-nor-9,10-secochola-5,7-diene-1,3,24a-triol 176b 163. 1.39 ml of 4-trifluoromethylbromobenzene is introduced into 20 ml of tetrahydrofuran, and 3.96 ml of n-butyllithium solution (2.5 M in hexane) is added at −78° C. After 30 minutes at this temperature, 762 mg of aldehyde 8 in 5 ml of tetrahydrofuran is added in drops, and it is stirred for 1 more hour. Then, it is quenched with sodium chloride solution, extracted with ethyl acetate, the organic phase is washed with sodium chloride solution and dried on sodium sulfate. The solvent is removed, and the residue is chromatographed on silica gel with ethyl acetate/hexane, whereby 587 mg of [1R-[1α(1R*),3aβ,4α,7aα]]-α-[4-[octahydro-7a-methyl-4-[(triethylsilyl)oxy]-1H-inden-1-yl]pentyl]-4-(trifluoromethylphenyl)methanol 170 is obtained as a colorless oil.

$^1$H-NMR (CDCl$_3$): δ=0.56 ppm (q, 6H); 0.89 (d, 3H); 0.91 (s, 3H); 0.95 (t, 9H); 2.33 (s, 3H); 4.02 (m, 1H); 4.75 (m, 1H); 7.48 (d, 2H); 7.61 (d, 2H)

164. 580 mg of alcohol 170 is treated analogously to 9., and 566 mg of [1R-[1α(1R*),3aβ,4α,7aα]]-5-[octahydro-7a-methyl-4-[(triethylsilyl)oxy]-1H-inden-1-yl]-1-(4-trifluoromethylphenyl)hexyl-acetate 171 is obtained as a colorless oil.

$^1$H-NMR (CDCl$_3$): δ=0.56 ppm (q, 6H); 0.88/0.89 (d, 3H); 0.90/0.91 (s, 3H); 0.95(t, 9H); 2.10 (s, 3H); 4.02 (m, 1H); 5.74 (m, 1H); 7.42 (d, 2H); 7.61 (d, 2H)

165. 556 mg of acetate 171 is treated analogously to 10., and 208 mg of [1R-[1α(1R*),3aβ,4α,7aα]]-1-[5-(acetyloxy)-1-methyl-5-(4-trifluoromethylphenyl)pentyl]octahydro-7a-methyl-1H-inden-4-ol 172 is obtained as a colorless oil.

$^1$H-NMR (CDCl$_3$): δ=0.88/0.89 ppm (d, 3H); 0.91/0.92 (s, 3H); 2.11 (s, 3H); 4.08 (m, 1H); 5.75 (m, 1H); 7.43 (d, 2H); 7.61 (d, 2H)

166. 160 mg of alcohol 172 is treated analogously to 11., and 138 mg of [1R-[1α(1R*),3aβ,7aα]]-1-[5-(acetyloxy)-1-methyl-5-(4-trifluoromethylphenyl)pentyl]octahydro-7a-methyl-4H-inden-4-one 173 is obtained as a colorless oil.

$^1$H-NMR (CDCl$_3$): δ=0.61/0.62 ppm (s, 3H); 0.92/0.93 (d, 3H); 2.09 (s, 3H); 5.75 (m, 1H); 7.45 (d, 2H); 7.61 (d, 2H)

167. 348 mg of phosphine oxide 13, which was deprotonated with 0.29 ml of n-butyllithium solution (2.5 M in hexane), is reacted with 134 mg of ketone 173 analogously to 12., and 173 mg of (7E)-(1R,3R)-24a-(acetyloxy)-1,3-bis[[(1,1-dimethylethyl)dimethylsilyl]oxy]-24a-(4-trifluoromethyl-phenyl)-24a-homo-19-nor-9,10-secochola-5,7-diene 174 is obtained as a colorless foam.

$^1$H-NMR (CDCl$_3$): δ=0.07 ppm (s, 12H); 0.52/0.53 (s, 3H); 0.90 (s, 18H); 0.91 (d, 3H); 2.10)(s, 3H); 4.08 (m, 2H); 5.73 (m, 1H); 5.80 (d, 1H); 6.18 (d, 1H); 7.61 (d, 2H)

168. 173 mg of acetate 174 is treated analogously to 13., and 147 mg of (7E)-(1R,3R)-1,3-bis[[(1,1-dimethylethyl)dimethylsilyl]oxy]-24a-(4-trifluoromethylphenyl)-24a-homo-19-nor-9,10-secochola-5,7-dien-24a-ol 175 is obtained as a colorless foam.

$^1$H-NMR (CDCl$_3$): δ=0.05 ppm (s, 12H); 0.52/0.53 (s, 3H); 0.89 (s, 18H); 0.90 (d, 3H); 4.09 (m, 2H); 4.76 (m, 1H); 5.81 (d, 1H); 6.18 (d, 1H); 7.48 (d, 2H); 7.61 (s, 2H)

169. 113 mg of alcohol 175 is treated analogously to 14., and after the diastereomers (in terms of C-24a) are separated by HPLC, 21 mg of title compound 176a and 19 mg of title compound 176b are obtained as colorless foams.

$^1$H-NMR (CD$_2$Cl$_2$): 176a: δ=0.51 ppm (s, 3H); 0.86 (d, 3H); 3.95 (m, 1H); 4.02 (m, 1H); 4.73 (t, 1H); 5.82 (d, 1H); 6.25 (d, 1H); 7.45 (d, 2H); 7.60 (d, 2H)

176b: δ=0.51 ppm (s, 3H); 0.86 (d, 3H); 3.95 (m, 1H); 4.02 (m, 1H); 4.74 (t, 1H); 5.82 (d, 1H); 6.25 (d, 1H); 7.45 (d, 2H); 7.60 (d, 2H)

Example 39

(7E)-(1R,3R)-1,3-Dihydroxy-24a-(4-trifluoromethylphenyl)-24a-homo-19-nor-9,10-secochola-5,7-dien-24a-one 178

170. 33 mg of alcohol 175 is treated analogously to 25., whereby 18 mg of (7E)-(1R,3R)-1,3-bis[[(1,1-dimethylethyl)dimethylsilyl]oxy]-24a-(4-trifluoromethylphenyl)-24a-homo-19-nor-9,10-secochola-5,7-dien-24a-one 177 accumulates as a colorless foam.

$^1$H-NMR (CDCl$_3$): δ=0.07 ppm (s, 12H); 0.54 (s, 3H); 0.89 (s, 18H); 0.98 (d, 3H); 4.08 (m, 2H); 5.82 (d, 1H); 6.18 (d, 1H); 7.73 (d, 2H); 8.08 (d, 2H)

171. 18 mg of ketone 177 is treated analogously to 26., whereby 9 mg of title compound 178 accumulates as a colorless foam.

$^1$H-NMR (CD$_2$Cl$_2$): δ=0.54 ppm (s, 3H); 0.95 (d, 3H); 3.96 (m, 1H); 4.03 (m, 1H); 5.85 (d, 1H); 6.26 (d, 1H); 7.73 (d, 2H); 8.05 (d, 2H)

Example 40

(7E)-(1R,3R,24aR)-24a-(4-Methoxyphenyl)-24a-homo-19-nor-9,10-secochola-5,7-diene-1,3,24a-triol 185a and (7E)-(1R,3R,24aS)-24a-(4-methoxyphenyl)-24a-homo-19-nor-9,10-secochola-5,7-diene-1,3, 24a-triol 185b 172. 0.85 ml of 4-bromoanisole is introduced into 18 ml of tetrahydrofuran, and 2.72 ml of n-butyllithium solution (2.5 M in hexane) is added at −78° C. After 30 minutes at this temperature, 500 mg of aldehyde 8 in 4 ml of tetrahydrofuran is added in drops, and it is stirred for 1 more hour. Then, it is quenched with sodium chloride solution, extracted with ethyl acetate, the organic phase is washed with sodium chloride solution and dried on sodium sulfate. The solvent is removed, and the residue is chromatographed on silica gel with ethyl acetate/hexane, whereby 497 mg of [1R-[1α(1R*),3aβ,4α,7aα]]-α-[4-[octahydro-7a-methyl-4-[(triethylsilyl)oxy]-1H-inden-1-yl]pentyl]-4-(methoxyphenyl)methanol 179 is obtained as a colorless oil.

$^1$H-NMR (CDCl$_3$): δ=0.54 ppm (q, 6H); 0.89 (d, 3H); 0.90 (s, 3H); 0.94 (t, 9H); 3.80 (s, 3H); 4.01 (m, 1H); 4.61 (m, 1H); 6.88 (d, 2H); 7.28 (d, 2H)

173. 490 mg of alcohol 179 is treated analogously to 9., and 509 mg of [1R-[1α(1R*),3aβ,4α,7aα]]-5-[octahydro-7a-methyl-4-[(triethylsilyl)oxy]-1H-inden-1-yl]-1-(4-methoxyphenyl)hexyl-acetate 180 is obtained as a colorless oil.

$^1$H-NMR (CDCl$_3$): δ=0.56 ppm (q, 6H); 0.88/0.89 (d, 3H); 0.90/0.91 (s, 3H); 0.95 (t, 9H); 2.06 (s, 3H); 3.80 (s, 3H); 4.02 (m, 1H); 5.69 (m, 1H); 6.88 (d, 2H); 7.28 (d, 2H)

174. 504 mg of acetate 180 is treated analogously to 10., and 280 mg of [1R-[1α(1R*),3aβ,4α,7aα]]-1-[5-(acetyloxy)-1-methyl-5-(4-methoxyphenyl)pentyl]octahydro-7a-methyl-1H-inden-4-ol 181 is obtained as a colorless oil.

$^1$H-NMR (CDCl$_3$): δ=0.87/0.88 ppm (d, 3H); 0.91/0.92 (s, 3H); 2.07 (s, 3H); 3.80 (s, 3H); 4.08 (m, 1H); 5.68 (m, 1H); 6.88 (d, 2H); 7.28 (d, 2H)

175. 275 mg of alcohol 181 is treated analogously to 11., and 252 mg of [1R-[1α(1R*),3aβ,7aα]]-1-[5-(acetyloxy)-1-methyl-5-(4-methoxyphenyl)pentyl]octahydro-7a-methyl-4H-inden-4-one 182 is obtained as a colorless oil.

$^1$H-NMR (CDCl$_3$): δ=0.61/0.62 ppm (s, 3H); 0.91/0.92 (d, 3H); 2.07 (s, 3H); 3.80 (s, 3H); 5.68 (m, 1H); 6.88 (d, 2H); 7.28 (d, 2H)

176. 370 mg of phosphine oxide 13, which was deprotonated with 0.30 ml of n-butyllithium solution (2.5 M in hexane), is reacted with 130 mg of ketone 182 analogously to 12., and 206 mg of (7E)-(1R,3R)-24a-(acetyloxy)-1,3-bis[[(1,1-dimethylethyl)dimethylsilyl]oxy]-24a-(4-methoxyphenyl)-24a-homo-19-nor-9,10-secochola-5,7-diene 183 is obtained as a colorless foam.

$^1$H-NMR (CDCl$_3$): δ=0.07 ppm (s, 12H); 0.52/0.53 (s, 3H); 0.90 (s, 18H); 0.91 (d, 3H); 2.03 (s, 3H); 3.81 (s, 3H); 4.08 (m, 2H); 5.69 (m, 1H); 5.81 (d, 1H); 6.18 (d, 1H); 6.88 (d, 2H); 7.28 (d, 2H)

177. 200 mg of acetate 183 is reacted analogously to 13., and 175 mg of (7E)-(1R,3R)-1,3-bis[[(1,1-dimethylethyl)dimethylsilyl]oxy]-24a-(4-methoxyphenyl)-24a-homo-19-nor-9,10-secochola-5,7-dien-24a-ol 184 is obtained as a colorless foam.

¹H-NMR (CDCl₃): δ=0.07 ppm (s, 12H); 0.52/0.53 (s, 3H); 0.89 (s, 18H); 0.90 (d, 3H); 3.80 (s, 3H); 4.09 (m, 2H); 4.63 (m, 1H); 5.81 (d, 1H); 6.18 (d, 1H); 6.90 (d, 2H); 7.30 (d, 2H)

178. 130 mg of alcohol 184 is treated analogously to 14., and after diastereomers (in terms of C-24a) are separated by HPLC, 26 mg of title compound 185a and 22 mg of title compound 185b are obtained as colorless foams.

¹H-NMR (CD₂Cl₂): 185a: δ=0.52 μm (s, 3H); 0.89 (d, 3H); 3.80 (s, 3H); 3.97 (m, 1H); 4.04 (m, 1H); 4.59 (t, 1H); 5.82 (d, 1H); 6.27 (d, 1H); 6.88 (d, 2H); 7.25 (d, 2H)

185b: δ=0.52 ppm (s, 3H); 0.89 (d, 3H); 3.79 (s, 3H); 3.97 (m, 1H); 4.04 (m, 1H); 4.60 (t, 1H); 5.82 (d, 1H); 6.27 (d, 1H); 6.88 (d, 2H); 7.25 (d, 2H)

Example 41

(7E)-(1R,3R)-1,3-Dihydroxy-24a-(4-methoxyphenyl)-24a-homo-19-nor-9,10-secochola-5,7-dien-24a-one 187

179. 44 mg of alcohol 184 is treated analogously to 25., whereby 27 mg of (7E)-(1R,3R)-1,3-bis[[(1,1-dimethylethyl)dimethylsilyl]oxy]-24a-(4-methoxyphenyl)-24a-homo-19-nor-9,10-secochola-5,7-dien-24a-one 186 accumulates as a colorless foam.

¹H-NMR (CD₂Cl₂): δ=0.04 ppm (s, 12H); 0.51 (s, 3H); 0.84 (s, 18H); 0.94 (d, 3H); 3.82 (s, 3H); 4.08 (m, 2H); 5.81 (d, 1H); 6.15 (d, 1H); 6.91 (d, 2H); 7.90 (d, 2H)

180. 27 mg of ketone 186 is treated analogously to 26., whereby 16 mg of title compound 187 accumulates as a colorless foam.

¹H-NMR (CD₂Cl₂): δ=0.51 ppm (s, 3H); 0.92 (d, 3H); 3.80 (s, 3H); 3.96 (m, 1H); 4.02 (m, 1H); 5.83 (d, 1H); 6.24 (d, 1H); 6.92 (d, 2H); 7.91 (d, 2H)

Example 42

(7E)-(1R,3R,20S,24aR)-24a-(Thiazol-2-yl)-24a-homo-19-nor-9,10-secochola-5,7-diene-1,3,24a-triol 202a and (7E)-(1R,3R,20S,24aS)-24a-(thiazol-2-yl)-24-a-homo-19-nor-9,10-secochola-5,7-diene-1,3,24a-triol 202b 181. 3.89 g of alcohol 3 is introduced into 250 ml of dichloromethane, and 7.74 g of pyridinium chlorochromate is added. It is stirred for 3 hours at room temperature and then diluted with diethyl ether, suctioned off on Celite and concentrated by evaporation. The residue is chromatographed on silica gel with ethyl acetate/hexane, whereby 3.19 g of [1R-[1α(1S*),3aβ,4α,7aα]]-2-[octahydro-7a-methyl-4-[(triethylsilyl)oxy]-1H-inden-1-yl]propanol 188 is obtained as a colorless oil.

¹H-NMR (CDCl₃): δ=0.56 ppm (q, 6H); 0.93 (s, 3H); 0.94 (t, 9H); 1.10 (t, 9H); 4.07 (m, 1H); 9.58 (s, 1H)

182. 6.23 g of aldehyde 188 is introduced into 60 ml of toluene and 60 ml of methanol, 4 ml of diazabicycloundecane is added, and it is stirred for 4 days at room temperature. The crude product is concentrated by evaporation and chromatographed on silica gel with ethyl acetate/hexane, whereby 5.63 g of the diastereomer mixture [1R-[1α(1S*), 3aβ,4α,7aα]]-2-[octahydro-7a-methyl-4-[(triethylsilyl)-oxy]-1H-inden-1-yl]propanal 188 and [1R-[1α(1R*),3aβ, 4α,7aα]]-2-[octahydro-7a-methyl-4-[(triethylsilyl)oxy]-1H-inden-1-yl]propanal 189 are obtained as a colorless oil.

¹H-NMR (CDCl₃): 189: δ=0.56 ppm (q, 6H); 0.93 (d, 3H); 0.94 (t, 9H); 1.02 (d, 3H); 4.07 (m, 1H); 9.53 (d, 1H)

183. 5.63 g of the epimer mixture of aldehyde 188/189 is dissolved in 100 ml of ethanol and 10 ml of tetrahydrofuran, and 377 mg of sodium borohydride is added in portions. It is stirred for 1 hour at room temperature and then carefully quenched with ammonium chloride solution. It is extracted with dichloromethane, the organic phase is washed with sodium chloride solution, dried on sodium sulfate and concentrated by evaporation. The residue is chromatographed on silica gel with ethyl acetate/hexane, whereby 2.61 g of [1R-[1α(1R*),3aβ,4α,7aα]]-2-[octahydro-7a-methyl-4-[(triethylsilyl)oxy]-1H-inden-1-yl]-1-propanol 190 in addition to 2.10 g of compound 3 that is normally configured at 20 are obtained as colorless oils.

¹H-NMR (CDCl₃): δ=0.55 ppm (q, 6H); 0.92 (d, 3H); 0.94 (t, 9H); 0.98 (d, 3H); 3.46 (dd, 1H); 3.72 (dd, 1H); 4.03 (m, 1H)

184. 2.61 g of alcohol 190 is introduced into 80 ml of pyridine, cooled to 0° C., and 3.04 g of p-toluenesulfonyl chloride is added. It is stirred for 5 more hours at this temperature, and then the reaction mixture is poured onto sodium bicarbonate solution. It is extracted with ethyl acetate, the organic phase is washed with sodium chloride solution and dried on sodium sulfate. The residue is chromatographed on silica gel with ethyl acetate/hexane, whereby 3.19 g of [1R-[1α(1R*),3aβ,4α,7aα]]-2-[octahydro-7a-methyl-4-[(triethylsilyl)oxy]-1H-inden-1-yl]propyl-(4-methylbenzenesulfonate) 191 is obtained as a colorless oil.

¹H-NMR (CDCl₃): δ=0.54 ppm (q, 6H); 0.81 (s, 3H); 0.88 (d, 3H); 0.94 (t, 9H); 2.47 (s, 3H); 3.78 (dd, 1H); 4.01 (m, 1H); 4.12 (dd, 1H); 7.34 (d, 1H); 7.79 (d, 1H)

185. 4.5 ml of propargyl-THP-ether is introduced into 100 ml of dioxane, and 12.8 ml of n-butyllithium solution (2.5 M in hexane) is added in drops. After 1 hour, 3.18 g of tosylate 191 in 20 ml of dioxane is added in drops. For 2 days, it is now heated to boiling. After cooling, it is quenched with sodium bicarbonate solution, extracted with ethyl acetate, the organic phase is washed with sodium chloride solution and concentrated by evaporation. The residue is chromatographed on silica gel with ethyl acetate/hexane, whereby 2.62 g of [1R-[1α(1S*),3aβ,4α,7aα]]-octahydro-7a-methyl-1-[5-[(tetrahydro-2H-pyran-2-yl)oxy]-1-methyl-3-pentinyl]-4-[(triethylsilyl)oxy]-1H-indene 192 is obtained as a colorless oil.

¹H-NMR (CDCl₃): δ=0.55 ppm (q, 6H); 0.89 (s, 3H); 0.92 (d, 3H); 0.94 (t, 9H); 4.02 (m, 1H); 4.28 (m, 2H); 4.94 (m, 1H)

186. 2.62 g of alkine 192 is introduced into 50 ml of ethyl acetate, 465 mg of palladium/carbon (10%) and 1.06 g of sodium bicarbonate are added and hydrogenated at normal pressure. The reaction mixture is then filtered on Celite and concentrated by evaporation. The crude product (2.08 g) of [1R-[1α(1S*),3aβ,4α,7aα]]-octahydro-7a-methyl-1-[5-[(tetrahydro-2H-pyran-2-yl)oxy]-1-methyl-pentyl]-4-[(triethylsilyl)oxy]-1H-indene 193 is immediately further reacted.

187. 2.08 g of THP-ether 193 is introduced into 100 ml of dichloromethane, and 9.2 ml of diethylaluminum chloride solution (1.8 M in toluene) is added in drops. After 2 hours at room temperature, it is quenched with isopropanol/water (15:85), toluene is added, and stirring is continued overnight. Then, it is suctioned off on Celite and concentrated by evaporation. The residue is chromatographed on silica gel with ethyl acetate/hexane, whereby 1.02 g of [1R-[1α(1S*), 3aβ,4α,7aα]]-5-[octahydro-7a-methyl-4-[(triethylsilyl) oxy]-1H-inden-1-yl]-1-hexanol 194 is obtained as a colorless oil.

$^1$H-NMR (CDCl$_3$): δ=0.56 ppm (q, 6H); 0.82 (d, 3H); 0.92 (s, 3H); 0.96 (t, 9H); 3.64 (t, 2H); 4.02 (m, 1H)

188. 1.02 g of alcohol 194 is dissolved in 40 ml of dichloromethane, and then 835 mg of pyridinium chlorochromate is added. It is stirred for 2 hours at room temperature, then diethyl ether is added, filtered on Celite and concentrated by evaporation. The residue is chromatographed on silica gel with ethyl acetate/hexane, whereby 810 mg of [1R-[1α(1S*),3aβ,4α,7aα]]-5-[octahydro-7a-methyl-4-[(triethylsilyl)oxy]-1H-inden-1-yl]hexanal 195 is obtained as a colorless oil.

$^1$H-NMR (CDCl$_3$): δ=0.56 ppm (q, 6H); 0.83 (d, 3H); 0.91 (s, 3H); 0.96 (t, 9H); 2.40 (t, 2H); 4.02 (m, 1H); 9.78 (sbr, 1H)

189. 0.99 ml of 2-bromothiazole is introduced into 20 ml of tetrahydrofuran, and 4.42 ml of n-butyllithium solution (2.5 M in hexane) is added at −78° C. After 30 minutes at this temperature, 810 mg of aldehyde 195 in 5 ml of tetrahydrofuran is added in drops, and it is stirred for 1 more hour. Then, it is quenched with sodium chloride solution, extracted with ethyl acetate, the organic phase is washed with sodium chloride solution and dried on sodium sulfate. The solvent is removed, and the residue is chromatographed on silica gel with ethyl acetate/hexane, whereby 878 mg of [1R-[1α(1S*),3aβ,4α,7aα]]-α-[4-[octahydro-7a-methyl-4-[(triethylsilyl)oxy]-1H-inden-1-yl]pentyl]thiazole-2-methanol 196 is obtained as a colorless oil.

$^1$H-NMR (CDCl$_3$): δ=0.57 ppm (q, 6H); 0.80 (d, 3H); 0.90 (s, 3H); 0.97 (t, 9H); 4.02 (m, 1H); 5.01 (m, 1H); 7.30 (d, 1H); 7.72 (d, 1H)

190. 878 mg of alcohol 196 is treated analogously to 9., and 709 mg of [1R-[1α(1S*),3aβ,4α,7aα]]-5-[octahydro-7a-methyl-4-[(triethylsilyl)oxy]-1H-inden-1-yl]-1-(thiazol-2-yl)hexyl-acetate 197 is obtained as a colorless oil.

$^1$H-NMR (CDCl$_3$): δ=0.56 ppm (q, 6H); 0.78/0.79 (d, 3H); 0.89 (s, 3H); 0.96 (t, 9H); 2.14 (s, 3H); 4.02 (m, 1H); 6.10 (t, 1H); 7.30 (d, 1H); 7.78 (d, 1H)

191. 704 mg of acetate 197 is treated analogously to 10., and 490 mg of [1R-[1α(1S*),3aβ,4α,7aα]]-1-[5-(acetyloxy)-1-methyl-5-(thiazol-2-yl)pentyl]octahydro-7a-methyl-1H-inden-4-ol 198 is obtained as a colorless oil.

$^1$H-NMR (CDCl$_3$): δ=0.78/0.79 ppm (d, 3H); 0.92 (s, 3H); 2.16 (s, 3H); 4.07 (m, 1H); 6.10 (t, 1H); 7.30 (d, 1H); 7.78 (d, 1H)

192. 485 mg of alcohol 198 is treated analogously to 11., and 480 mg of [1R-[1α(1S*),3aβ,7aα]]-1-[5-(acetyloxy)-1-methyl-5-(thiazol-2-yl)pentyl]octahydro-7a-methyl-4H-inden-4-one 199 is obtained as a colorless oil.

$^1$H-NMR (CDCl$_3$): δ=0.60 ppm (s, 3H); 0.81/0.82 (d, 3H); 2.13 (s, 3H); 6.10 (t, 1H); 7.31 (d, 1H); 7.78 (d, 1H)

193. 665 mg of phosphine oxide 13, which was deprotonated with 0.56 ml of n-butyllithium solution (2.5 M in hexane), is reacted with 220 mg of ketone 199 analogously to 12., and 299 mg of (7E)-(1R,3R,20S)-24a-(acetyloxy)-1, 3-bis[[(1,1-dimethylethyl)dimethylsilyl]oxy]-24a-(thiazol-2-yl)-24a-homo-19-nor-9,10-secochola-5,7-diene 200 is obtained as a colorless foam.

$^1$H-NMR (CDCl$_3$): δ=0.07 ppm (s, 12H); 0.53 (s, 3H); 0.83 (d, 3H); 0.89 (s, 18H); 2.18 (s, 3H); 4.08 (m, 2H); 5.82 (d, 1H); 6.10 (t, 1H); 6.18 (d, 1H); 7.31 (d, 1H); 7.78 (d, 1H)

194. 299 mg of acetate 200 is reacted analogously to 13., and 240 mg of (7E)-(1R,3R,20S)-1,3-bis[[(1,1-dimethylethyl)dimethylsilyl]oxy]-24a-(thiazol-2-yl)-24a-homo-19-nor-9,10-secochola-5,7-dien-24a-ol 201 is obtained as a colorless foam.

$^1$H-NMR (CDCl$_3$): δ=0.07 ppm (s, 12H); 0.53 (s, 3H); 0.83 (d, 3H); 0.89 (s, 18H); 4.07 (m, 2H); 5.01 (m, 1H); 5.81 (d, 1H); 6.18 (d, 1H); 7.30 (d, 1H); 7.72 (d, 1H)

195. 192 mg of alcohol 201 is treated analogously to 14., and after the diastereomers (in terms of C-24a) are separated by HPLC, 41 mg of title compound 202a and 49 mg of title compound 202b are obtained as colorless foams.

$^1$H-NMR (CD$_2$Cl$_2$/CD$_3$OD): 202a: δ=0.50 ppm (s, 3H); 0.80 (d, 3H); 3.93 (m, 1H); 4.01 (m, 1H); 4.90 (t, 1H); 5.82 (d, 1H); 6.24 (d, 1H); 7.29 (d, 1H); 7.68 (d, 1H)

202b: δ=0.50 ppm (s, 3H); 0.80 (d, 3H); 3.93 (m, 1H); 4.01 (m, 1H); 4.91 (t, 1H); 5.82 (d, 1H); 6.24 (d, 1H); 7.30 (d, 1H); 7.68 (d, 1H)

Example 43

(7E)-(1R,3R,20S)-1,3-Dihydroxy-24a-(thiazol-2-yl)-24-a-homo-19-nor-9,10-secochola-5,7-dien-24a-one 204

196. 43 mg of alcohol 201 is treated analogously to 25., whereby 32 mg of (7E)-(1R,3R,20S)-1,3-bis[[(1,1-dimethylethyl)dimethylsilyl]oxy]-24a-(thiazol-2-yl)-24a-homo-19-nor-9,10-secochola-5,7-dien-24a-one 203 accumulates as a colorless foam.

$^1$H-NMR (CDCl$_3$): δ=0.07 ppm (s, 12H); 0.52 (s, 3H); 0.88 (s, 18H); 0.89 (d, 3H); 4.08 (m, 2H); 5.81 (d, 1H); 6.18 (d, 1H); 7.68 (d, 1H); 8.00 (d, 12H)

197. 31 mg of ketone 203 is treated analogously to 26., whereby 12 mg of title compound 204 accumulates as a colorless foam.

$^1$H-NMR (CD$_2$Cl$_2$): δ=0.51 ppm (s, 3H); 0.88 (d, 3H); 3.97 (m, 1H); 4.03 (m, 1H); 5.82 (d, 1H); 6.26 (d, 1H); 7.67 (d, 1H); 7.97 (d, 1H)

Example 44

(5Z,7E)-(1S,3R,20S,24aR)-24a-(Thiazol-2-yl)-24a-homo-9,10-secochola-5,7,10(19)-triene-1,3,24a-triol 205a and (5Z,7E)-(1S,3R,20S,24aS)-24a-(thiazol-2-yl)-24a-homo-9,10-secochola-5,7,10(19)-triene-1,3, 24a-triol 205b 198. 740 mg of phosphine oxide 17, which was deprotonated with 0.61 ml of n-butyllithium solution (2.5 M in hexane), is reacted with 240 mg of ketone 199 analogously to 15., and 392 mg of (5Z,7E)-(1S,3R,20S)-24a-(acetyloxy)-1,3-bis[[(1,1-dimethylethyl)dimethylsilyl]oxy]-24a-(thiazol-2-yl)-24a-homo-9,10-secochola-5,7,10(19)-triene 205 is obtained as a colorless foam.

$^1$H-NMR (CDCl$_3$): δ=0.07 ppm (s, 12H); 0.52 (s, 3H); 0.83 (d, 3H); 0.90 (s, 18H); 2.16 (s, 3H); 4.19 (m, 1H); 4.38 (m, 1H); 4.88 (s, 1H); 5.19 (s, 1H); 6.01 (d, 1H); 6.10 (t, 1H); 6.24 (d, 1H); 7.31 (d, 1H); 7.78 (d, 1H)

199. 392 mg of acetate 205 is reacted analogously to 13., and 274 mg of (5Z,7E)-(1S,3R,20S)-1,3-bis[[(1,1-dimethylethyl)dimethylsilyl]oxy]-24a-(thiazol-2-yl)-24a-homo-9, 10-secochola-5,7,10(19)-trien-24a-ol 206 is obtained as a colorless foam.

$^1$H-NMR (CDCl$_3$): δ=0.07 ppm (s, 12H); 0.52 (s, 3H); 0.83 (d, 3H): 0.90 (s, 18H); 4.19 (m, 1H); 4.38 (m, 1H); 4.88 (s, 1H); 5.01 (m, 1H); 5.18 (s, 1H); 6.01 (d, 1H); 6.23 (d, 1H); 7.30 (d, 1H); 7.72 (d, 1H)

200. 218 mg of alcohol 206 is treated analogously to 14., and after the diastereomers (in terms of C-24a) are separated by HPLC, 40 mg of title compound 207a and 39 mg of title compound 207b are obtained as colorless foams.

$^1$H-NMR (CD$_2$Cl$_2$/CD$_3$OD): 207a: δ=0.50 ppm (s, 3H); 0.79 (d, 3H); 4.13 (m, 1H); 4.34 (m, 1H); 4.90 (t, 1H); 4.93 (s, 1H); 5.28 (s, 1H); 6.00 (d, 1H); 6.32 (d, 1H); 7.30 (d, 1H); 7.69 (d, 1H)

207b: δ=0.50 ppm (s, 3H); 0.80 (d, 3H); 4.13 (m, 1H); 4.34 (m, 1H); 4.91 (t, 1H); 4.93 (s, 1H); 5.28 (s, 1H); 6.00 (d, 1H); 6.32 (d, 1H); 7.30 (d, 1H); 7.69 (d, 1H)

Example 45

(5Z,7E)-(1S,3R,20S)-1,3-Dihydroxy-24a-(thiazol-2-yl)-24a-homo-9,10-secochola-5,7,10(19)-trien-24a-one 209

201. 51 mg of alcohol 206 is treated analogously to 25., whereby 42 mg of (5Z,7E)-(1S,3R,20S)-1,3-bis[[(1,1-dimethylethyl)dimethylsilyl]oxy]-24a-(thiazol-2-yl)-24a-homo-9,10-secochola-5,7,10(19)-trien-24a-one 208 accumulates as a colorless foam.

$^1$H-NMR (CDCl$_3$): δ=0.07 ppm (s, 12H); 0.52 (s, 3H); 0.89 (s, 18H); 0.90 (d, 3H); 4.19 (m, 1H); 4.38 (m, 1H); 4.88 (s, 1H); 5.19 (s, 1H); 6.02 (d, 1H); 6.24 (d, 1H); 7.68 (d, 1H); 8.00 (d, 1H)

202. 41 mg of ketone 208 is treated analogously to 26., whereby 14 mg of title compound 209 accumulates as a colorless foam.

$^1$H-NMR (CD$_2$Cl$_2$): δ=0.50 ppm (s, 3H); 0.86 (d, 3H); 4.15 (m, 1H); 4.36 (m, 1H); 4.94 (s, 1H); 5.28 (s, 1H); 6.00 (d, 1H); 6.34 (d, 1H); 7.66 (d, 1H); 7.96 (d, 1H)

Example 46

(5Z,7E)-(1S,3R,24S)-24-(Thiazol-2-yl)-9,10-secochola-5,7,10(19)-trien-1,3,24-triol 217a and (5Z,7E)-(1S,3R,24R)-24-(thiazol-2-yl)-9,10-secochola-5,7,10(19)-trien-1,3,24-triol 217b 203. 21 g of (5Z,7E)-(1S,3R,20S)-1,3-bis[[(1,1-dimethylethyl)dimethylsilyl]oxy]-20-methyl-9,10-secopregna-5,7,10(19)-trien-21-al 210 (Schering A G, WO 97/41096) is dissolved in 70 ml of tetrahydrofuran and 140 ml of ethanol, and 715 mg of sodium borohydride is added at 0° C. It is stirred for 1 hour at 0° C. and then quenched with ammonium chloride solution. It is extracted with ethyl acetate, the organic phase is washed with sodium chloride solution, dried on sodium sulfate and concentrated by evaporation. The residue is chromatographed on silica gel with ethyl acetate/hexane, whereby 20.54 g of 211 is obtained as a colorless foam.

$^1$H-NMR (CDCl$_3$): δ=0.07 ppm (s, 12H); 0.56 (s, 3H); 0.89 (s, 18H); 1.08 (d, 3H); 3.40 (dd, 1H); 3.67 (dd, 1H); 4.19 (m, 1H); 4.38 (m, 1H); 4.87 (s, 1H); 5.19 (s, 1H); 6.02 (d, 1H); 6.23 (d, 1H)

204. 14.54 g of alcohol 211 is dissolved in 233 ml of pyridine, 11.14 g of p-toluenesulfonyl chloride is added, and it is stirred for 4 hours at room temperature. It is carefully quenched with sodium bicarbonate solution, extracted with ethyl acetate, the organic phase is washed with sodium chloride solution and dried on sodium sulfate. The residue is chromatographed with ethyl acetate/hexane on silica gel, whereby 14.73 g of (5Z,7E)-(1S,3R,20S)-1,3-bis[[(1,1-dimethyl-ethyl-ethyl)dimethylsilyl]oxy]-20-methyl-9,10-secopregna-5,7,10(19)-triene-21-(4-methylbenzenesulfonate) 212 is obtained as a colorless foam.

$^1$H-NMR (CDCl$_3$): δ=0.07 ppm (s, 12H); 0.51 (s, 3H); 0.89 (s, 18H); 1.00 (d, 3H); 2.47 (s, 3H); 3.71 (dd, 1H); 3.99 (dd, 1H); 4.19 (m, 1H); 4.38 (m, 1H); 4.87 (s, 1H); 5.19 (s, 1H); 6.00 (d, 1H); 6.22 (d, 1H); 7.37 (d, 2H); 7.80 (d, 2H)

205. 14.73 g of tosylate 212 is dissolved in 295 ml of dichloromethane and 295 ml of acetonitrile, 16.9 g of lithium bromide and 700 mg of 1,8-bis(dimethylamino) naphthalene are added, and it is stirred overnight at 60° C. It is then quenched with sodium chloride solution, extracted with dichloromethane, the organic phase is washed with sodium chloride solution, dried on sodium sulfate and concentrated by evaporation. The residue is chromatographed with ethyl acetate/hexane on silica gel, whereby 9.70 g of (5Z,7E)-(1S,3R,20S)-1,3-bis[[(1,1-dimethylethyl)dimethylsilyl]oxy]-21-bromo-20-methyl-9,10-secopregna-5,7,10(19)-triene 213 is obtained as a colorless foam.

$^1$H-NMR (CDCl$_3$): δ=0.07 ppm (s, 12H); 0.58 (s, 3H); 0.89 (s, 18H); 1.11 (d, 3H); 3.38 (dd, 1H); 3.52 (dd, 1H); 4.19 (m, 1H); 4.38 (m, 1H); 4.88 (s, 1H); 5.20 (s, 1H); 6.02 (d, 1H); 6.25 (d, 1H)

206. Lithium diisopropylamide is produced from 15.5 ml of diisopropylamine and. 49 ml of n-butyllithium (2.5 M in hexane) in 150 ml of tetrahydrofuran, cooled to −78° C., and 6.34 ml of acetonitrile is added in drops. After 30 minutes, 7.8 g of bromide 213 in 20 ml of tetrahydrofuran is added. The reaction mixture is now allowed to heat to room temperature, stirred for 2 more hours and then quenched with sodium chloride solution. It is extracted with ethyl acetate, the organic phase is washed with sodium chloride solution, dried on sodium sulfate and concentrated by evaporation. The residue is chromatographed with ethyl acetate/hexane on silica gel, whereby 5.9 g of (5Z,7E)-(1S,3R)-1,3-bis[[(1,1-dimethylethyl)dimethylsilyl]oxy]-9,10-secochola-5,7,10(19)-triene-24-nitrile 214 is obtained as a colorless foam.

$^1$H-NMR (CDCl$_3$): δ=0.07 ppm (s, 12H); 0.57 (s, 3H); 0.89 (s, 18H); 0.97 (d, 3H); 4.19 (m, 1H); 4.38 (m, 1H); 4.88 (s, 1H); 5.19 (s, 1H); 6.02 (d, 1H); 6.23 (d, 1H)

207. 3.2 g of nitrile 214 is dissolved in 50 ml of tetrahydrofuran and cooled to 0° C. At this temperature, 16.8 ml of diisobutyl aluminum hydride (1.2 M in toluene) is added in drops, and it is stirred for 2 more hours. Then, ammonium chloride solution is added, the precipitate is suctioned off and extracted with ethyl acetate. The organic phase is washed with sodium chloride solution, dried on sodium sulfate and concentrated by evaporation. The residue is chromatographed on silica gel with ethyl acetate/hexane, whereby 2.5 g of (5Z,7E)-(1S,3R)-1,3-bis[[(1,1-dimethylethyl)dimethyl-silyl]oxy]-9,10-secochola-5,7,10(19)-trien-24-al 215 is obtained as a colorless foam.

$^1$H-NMR (CDCl$_3$): δ=0.07 ppm (s, 12H); 0.54 (s, 3H); 0.89 (s, 18H); 0.94 (d, 3H); 4.19 (m, 1H); 4.38 (m, 1H); 4.88 (s, 1H); 5.19 (s, 1H); 6.01 (d, 1H); 6.23 (d, 1H); 9.79 (sbr, 1H)

208. 285 mg of thiazole is introduced into 5 ml of tetrahydrofuran, and 1.34 ml of n-butyllithium solution (2.5 M in hexane) is added at −78° C. After 30 minutes at this temperature, 400 mg of aldehyde. 215 in 2 ml of tetrahydrofuran is added, and it is stirred for 1 more hour. Then, it is quenched with sodium chloride solution, extracted with ethyl acetate, the organic phase is washed with sodium chloride solution and dried on sodium sulfate. The solvent is removed, and the residue is chromatographed on silica gel with ethyl acetate/hexane, whereby 311 mg of (5Z,7E)-(1S, 3R)-1,3-bis[[(1,1-dimethylethyl)dimethylsilyl]oxy]-24-(thiazol-2-yl)-9,10-secochola-5,7,10(19)-trien-24-ol 216 is obtained as a colorless oil.

$^1$H-NMR (CDCl$_3$): δ=0.07 ppm (s, 12H); 0.53 (s, 3H); 0.89 (s, 18H); 0.95 (d, 3H); 4.19 (m, 1H); 4.38 (m, 1H); 4.88 (s, 1H); 4.98 (m, 1H); 5.19 (s, 1H); 6.01 (d, 1H); 6.23 (d, 1H); 7.30 (d, 1H); 7.72 (d, 1H)

209. 130 mg of alcohol 216 is treated analogously to 14., and after the diastereomers (in terms of C-24a) are separated by HPLC, 19 mg of title compound 217a and 16 mg of title compound 217b are obtained as colorless foams.

$^1$H-NMR (CD$_2$Cl$_2$/CD$_3$OD): 217a: δ=0.50 ppm (s, 3H); 0.92 (d, 3H); 4.10 (m, 1H); 4.33 (m, 1H); 4.85 (m, 1H); 4.93 (s, 1H); 5.28 (s, 1H); 6.01 (d, 1H); 6.32 (d, 1H); 7.32 (d, 1H); 7.64 (d, 1H)

217b: δ=0.51 ppm (s, 3H); 0.92 (d, 3H); 4.10 (m, 1H); 4.33 (m, 1H); 4.86 (m, 1H); 4.93 (s, 1H); 5.28 (s, 1H); 6.01 (d, 1H); 6.33 (d, 1H); 7.32 (d, 1H); 7.65 (d, 1H)

Example 47

(5Z,7E)-(1S,3R)-1,3-Dihydroxy-24-(thiazol-2-yl)-9,10-secochola-5,7,10(19)-trien-24-one 219

210. 40 mg of alcohol 216 is treated analogously to 25., whereby 24 mg of (5Z,7E)-(1S,3R)-1,3-bis[[(1,1-dimethylethyl)dimethylsilyl]oxy]-24-(thiazol-2-yl)-9,10-secochola-5,7,10(19)-trien-24-one 218 accumulates as a colorless foam.

$^1$H-NMR (CD$_2$Cl$_2$): δ=0.04 ppm (s, 12H); 0.52 (s, 3H); 0.84 (s, 18H); 0.97 (d, 3H); 4.17 (m, 1H); 4.36 (m, 1H); 4.84 (s, 1H); 5.16 (s, 1H); 6.01 (d, 1H); 6.23 (d, 1H); 7.65 (d, 1H); 7.97 (d, 1H)

211. 24 mg of ketone 218 is treated analogously to 26., whereby 14 mg of title compound 219 accumulates as a colorless foam.

$^1$H-NMR (CD$_2$Cl$_2$): δ=0.55 ppm (s, 3H); 0.99 (d, 3H); 4.15 (m, 1H); 4.36 (m, 1H); 4.93 (s, 1H); 5.28 (s, 1H); 6.00 (d, 1H); 6.33 (d, 1H); 7.65 (d, 1H); 7.98 (d, 1H)

Example 48

(5Z,7E)-(1S,3R,24S)-24-(4-Methylthiazol-2-yl)-9,10-secochola-5,7,10(19)-triene-1,3,24-triol 221a and (5Z,7E)-(1S,3R,24R)-24-(4-methylthiazol-2-yl)-9,10-secochola-5,7,10(19)-triene-1,3,24-triol 221b 212. 991 mg of 4-methylthiazole is introduced into 15 ml of tetrahydrofuran, and 4 ml of n-butyllithium solution (2.5 M in hexane) is added at −78° C. After 30 minutes at this temperature, 1.2 g of aldehyde 215 in 8 ml of tetrahydrofuran is added in drops, and it is stirred for 1 more hour. Then, it is quenched with sodium chloride solution, extracted with ethyl acetate, the organic phase is washed with sodium chloride solution and dried on sodium sulfate. The solvent is removed, and the residue is chromatographed on silica gel with ethyl acetate/hexane, whereby 1.03 g of (5Z,7E)-(1S,3R)-1,3-bis[[(1,1-dimethylethyl)dimethylsilyl]oxy]-24-(4-methylthiazol-2-yl)-9,10-secochola-5,7,10(19)-trien-24-ol 220 is obtained as a colorless oil.

$^1$H-NMR (CD$_2$Cl$_2$): δ=0.06 ppm (s, 12H); 0.53 (s, 3H); 0.87 (s, 18H); 0.94 (d, 3H); 2.35 (s, 3H); 4.17 (m, 1H); 4.36 (m, 1H); 4.85 (m, 1H); 4.86 (m, 1H); 5.17 (s, 1H); 6.01 (d, 1H); 6.23 (d, 1H); 6.83 (s, 1H).

213. 250 mg of alcohol 220 is treated analogously to 14., and after the diastereomers (in terms of C-24a) are separated by HPLC, 57 mg of title compound 221a and 63 mg of title compound 221b are obtained as colorless foams.

$^1$H-NMR (CD$_2$Cl$_2$): 221a: δ=0.51 ppm (s, 3H); 0.93 (d, 3H); 2.36 (s, 3H); 4.16 (m, 1H); 4.36 (m, 1H); 4.85 (m, 1H); 4.93 (s, 1H); 5.28 (s, 1H); 6.00 (d, 1H); 6.33 (d, 1H); 6.81 (s, 1H)

221b: δ=0.51 ppm (s, 3H); 0.93 (d, 3H); 2.36 (s, 3H); 4.16 (m, 1H); 4.35 (m, 1H); 4.85 (m, 1H); 4.92 (s, 1H); 5.27 (s, 1H); 6.00 (d, 1H); 6.33 (d, 1H); 6.82 (s, 1H)

Example 49

(5Z,7E)-(1S,3R)-1,3-Dihydroxy-24-(4-methylthiazol-2-yl)-9,10-secochola-5,7,10(19)-trien-24-one 223

214. 70 mg of alcohol 220 is treated analogously to 25., whereby 56 mg of (5Z,7E)-(1S,3R)-1,3-bis[[(1,1-dimethylethyl)dimethylsilyl]oxy]-24-(4-methylthiazol-2-yl)-9,10-secochola-5,7,10(19)-trien-24-one 222 accumulates as a colorless foam.

$^1$H-NMR (CD$_2$Cl$_2$): δ=0.04 ppm (s, 12H); 0.51 (s, 3H); 0.82 (s, 18H); 0.95 (d, 3H); 2.44 (s, 3H); 4.16 (m, 1H); 4.35 (m, 1H); 4.82 (s, 1H); 5.15 (s, 1H); 5.99 (d, 1H); 6.22 (d, 1H); 7.18 (s, 1H)

215. 56 mg of ketone 222 is treated analogously to 26., whereby 25 mg of title compound 223 accumulates as a colorless foam.

$^1$H-NMR (CD$_2$Cl$_2$): δ=0.54 ppm (s, 3H); 0.99 (d, 3H); 2.49 (s, 3H); 4.16 (m, 1H); 4.38 (m, 1H); 4.94 (s, 1H); 5.28 (s, 1H); 6.00 (d, 1H); 6.34 (d, 1H); 7.24 (d, 1H)

Example 50

(5Z,7E)-(1S,3R,24S)-24-(Thien-2-yl)-9,10-secochola-5,7,10(19)-triene-1,3,24-triol 225a and (5Z,7E)-(1S,3R,24R)-24-(thien-2-yl)-9,10-secochola-5,7,10(19)-triene-1,3,24-triol 225b 216. 450 mg of thiophene is introduced into 10 ml of tetrahydrofuran, and 2 ml of n-butyllithium solution (2.5 M in hexane) is added at −78° C. After 30 minutes at this temperature, 600 mg of aldehyde 215 in 4 ml of tetrahydrofuran is added in drops, and it is stirred for 1 more hour. Then, it is quenched with sodium chloride solution, extracted with ethyl acetate, the organic phase is washed with sodium chloride solution and dried on sodium sulfate. The solvent is removed, and the residue is chromatographed on silica gel with ethyl acetate/hexane, whereby 398 mg of (5Z,7E)-(1S,3R)-1,3-bis[[(1,1-dimethylethyl)dimethylsilyl]oxy]-24-(thien-2-yl)-9,10-secochola-5,7,10(19)-trien-24-ol 224 is obtained as a colorless oil.

$^1$H-NMR (CDCl$_3$): δ=0.06 ppm (s, 12H); 0.53 (s, 3H); 0.89 (s, 18H); 0.94 (d, 3H); 4.18 (m, 1H); 4.38 (m, 1H); 4.86 (s, 1H); 4.86 (m, 1H); 5.17 (s, 1H); 6.01 (d, 1H); 6.23 (d, 1H); 6.98 (m, 2H); 7.24 (m, 1H)

217. 92 mg of alcohol 224 is treated analogously to 14., and after the diastereomers (in terms of C-24a) are separated by HPLC, 21 mg of title compound 225a and 19 mg of title compound 225b are obtained as colorless foams.

$^1$H-NMR (CD$_2$Cl$_2$) 225a: δ=0.51 ppm (s, 3H); 0.92 (d, 3H); 4.14 (m, 1H); 4.34 (m, 1H); 4.83 (dd, 1H); 4.93 (s, 1H); 5.28 (s, 1H); 6.00 (d, 1H); 6.33 (d, 1H); 6.92 (m, 2H); 7.22 (dd, 1H)

225b: δ=0.51 ppm (s, 3H); 0.92 (d, 3H); 4.15 (m, 1H); 4.35 (m, 1H); 4.84 (t, 1H); 4.92 (s, 1H); 5.27 (s, 1H); 6.00 (d, 1H); 6.33 (d, 1H); 6.92 (m, 2H); 7.21 (dd, 1H)

Example 51

(5Z,7E)-(1S,3R)-1,3-Dihydroxy-24-(thien-2-yl)-9,10-secochola-5,7,10(19)-trien-24-one 227

218. 70 mg of alcohol 224 is treated analogously to 25., whereby 28 mg of (5Z,7E)-(1S,3R)-1,3-bis[[(1,1-dimethylethyl)dimethylsilyl]oxy]-24-(thien-2-yl)-9,10-secochola-5,7,10(19)-trien-24-one 226 accumulates as a colorless foam.

$^1$H-NMR (CD$_2$Cl$_2$): δ=0.05 ppm (s, 12H); 0.52 (s, 3H); 0.84 (s, 18H); 0.95 (d, 3H); 4.16 (m, 1H); 4.35 (m, 1H); 4.83 (s, 1H); 5.15 (s, 1H); 6.00 (d, 1H); 6.23 (d, 1H); 7.13 (t, 1H); 7.63 (d, 1H); 7.70 (d, 1H)

219. 28 mg of ketone 226 is treated analogously to 26., whereby 11 mg of title compound 227 accumulates as a colorless foam.

$^1$H-NMR (CD$_2$Cl$_2$): δ=0.54 ppm (s, 3H); 0.99 (d, 3H); 4.16 (m, 1H); 4.38 (m, 1H); 4.95 (s, 1H); 5.28 (s, 1H); 6.00 (d, 1H); 6.35 (d, 1H); 7.12 (dd, 1H); 7.62 (d, 1H); 7.71 (d, 1H)

Example 52

(5Z,7E)-(1S,3R,24S)-24-(4-Methylthien-2-yl)-9,10-secochola-5,7,10(19)-triene-1,3,24-triol 229a and (5Z,7E)-(1S,3R,24R)-24-(4-methylthien-2-yl)-9,10-secochola-5,7,10(19)-triene-1,3,24-triol 229b 220. 500 mg of 4-methylthiophene is introduced into 10 ml of tetrahydrofuran, and 2 ml of n-butyllithium solution (2.5 M in hexane) is added at −78° C. After 30 minutes at this temperature, 600 mg of aldehyde 215 in 4 ml of tetrahydrofuran is added in drops, and it is stirred for 1 more hour. Then, it is quenched with sodium chloride solution, extracted with ethyl acetate, the organic phase is washed with sodium chloride solution and dried on sodium sulfate. The solvent is removed, and the residue is chromatographed on silica gel with ethyl acetate/hexane, whereby 402 mg of (5Z,7E)-(1S,3R)-1,3-bis[[(1,1-dimethylethyl)dimethylsilyl]oxy]-24-(4-methylthien-2-yl)-9,10-secochola-5,7,10(19)-trien-24-ol 228 is obtained as a colorless oil.

$^1$H-NMR (CD$_2$Cl$_2$): δ=0.06 ppm (s, 12H); 0.55 (s, 3H); 0.86 (s, 18H); 0.94 (d, 3H); 2.21 (s, 3H); 4.16 (m, 1H); 4.36 (m, 1H); 4.84 (s, 1H); 4.86 (m, 1H); 5.16 (s, 1H); 6.01 (d, 1H); 6.23 (d, 1H); 6.74 (m, 1H); 7.78 (m, 1H)

221. 98 mg of alcohol 228 is treated analogously to 14., and after the diastereomers (in terms of C-24a) are separated by HPLC, 22 mg of title compound 229a and 17 mg of title compound 229b are obtained as colorless foams.

$^1$H-NMR (CD$_2$Cl$_2$): 229a: δ=0.52 ppm (s, 3H); 0.92 (d, 3H); 2.21 (s, 3H); 4.15 (m, 1H); 4.35 (m, 1H); 4.86 (dd, 1H); 4.93 (s, 1H); 5.28 (s, 1H); 5.99 (d, 1H); 6.33 (d, 1H); 6.84 (m, 1H); 6.89 (m, 1H)

229b: δ=0.52 ppm (s, 3H); 0.92 (d, 3H); 2.22 (s, 3H); 4.15 (m, 1H); 4.35 (m, 1H); 4.85 (t, 1H); 4.92 (s, 1H); 5.27 (s, 1H); 6.00 (d, 1H); 6.33 (d, 1H); 6.84 (m, 1H); 6.88 (m, 1H)

Example 53

(5Z,7E)-(1S,3R)-1,3-Dihydroxy-24-(4-methylthien-2-yl)-9,10-secochola-5,7,10(19)-trien-24-one 231

222. 65 mg of alcohol 228 is treated analogously to 25., whereby 34 mg of (5Z,7E)-(1S,3R)-1,3-bis[[(1,1-dimethylethyl)dimethylsilyl]oxy]-24-(4-methylthien-2-yl)-9,10-secochola-5,7,10(19)-trien-24-one 230 accumulates as a colorless foam.

$^1$H-NMR (CD$_2$Cl$_2$): δ=0.05 ppm (s, 12H); 0.53 (s, 3H); 0.84 (s, 18H); 0.94 (d, 3H); 2.33 (s, 3H); 4.16 (m, 1H); 4.35 (m, 1H); 4.83 (s, 1H); 5.15 (s, 1H); 6.01 (d, 1H); 6.23 (d, 1H); 7.65 (s, 1H); 7.70 (s, 1H)

223. 34 mg of ketone 230 is treated analogously to 26., whereby 13 mg of title compound 231 accumulates as a colorless foam.

$^1$H-NMR (CD$_2$Cl$_2$): δ=0.54 ppm (s, 3H); 0.98 (d, 3H); 2.32 (s, 3H); 4.16 (m, 1H); 4.37 (m, 1H); 4.95 (s, 1H); 5.28 (s, 1H); 6.00 (d, 1H); 6.34 (d, 1H); 7.63 (s, 1H); 7.71 (s, 1H)

Example 54

(7E)-(1R,3R,24aR)-24a-Fluoro-24a-(thiazol-2-yl)-24a-homo-19-nor-9,10-secochola-5,7-diene-1,3-diol 236a and (7E)-(1R,3R,24aS)-24a-fluoro-24a-(thiazol-2-yl)-24a-homo-19-nor-9,10-secochola-5,7-diene-1,3-diol 236b 224. 1.0 g of alcohol 21 is introduced into 80 ml of dichloromethane at −78° C., 0.044 ml of diethylaminosulfur trifluoride (DAST) is added, and it is stirred for 15 more minutes. It is quenched with sodium bicarbonate, extracted with dichloromethane and dried on sodium sulfate. After the concentration by evaporation and the chromatography on silica gel with ethyl acetate/hexane, 765 mg of [1R-[1α(1R*),3aβ,4α,7aα]]-1-[5-fluoro-1-methyl-5-(thiazol-2-yl)pentyl]octahydro-7a-methyl-4-[(triethylsilyl)oxy]-1H-indene 232 is obtained as a colorless oil.

$^1$H-NMR (CDCl$_3$): δ=0.55 ppm (q, 6H); 0.90 (d, 3H); 0.91 (s, 3H); 0.96 (t, 9H); 4.02 (m, 1H); 5.24 (dbr, 1H); 7.35 (d, 1H); 7.80 (t, 1H)

225. 765 mg of compound 232 is treated analogously to 10., and 505 mg of [1R-[1α(1R*),3aβ,4α,7aα]]-1-[5-fluoro-1-methyl-5-(thiazol-2-yl)pentyl]octahydro-7a-methyl-1H-inden-4-ol 233 is obtained as a colorless oil.

$^1$H-NMR (CDCl$_3$): δ=0.90 ppm (d, 3H); 0.92 (s, 3H); 4.08 (m, 1H); 5.75 (dbr, 1H); 7.38 (d, 1H); 7.80 (t, 1H)

226. 505 mg of alcohol 233 is treated analogously to 11., and 468 mg of [1R-[1α(1R*),3aβ,7aα]]-1-[5-fluoro-1-methyl-5-(thiazol-2-yl)pentyl]octahydro-7a-methyl-4H-inden-4-one 234 is obtained as a colorless oil.

$^1$H-NMR (CDCl$_3$): δ=0.62 ppm (s, 3H); 0.98 (d, 3H); 2.45 (dd, 1H); 5.75 (dbr, 1H); 7.38 (d, 1H); 7.80 (t, 1H)

227. 676 mg of phosphine oxide 13, which was deprotonated with 0.57 ml of n-butyllithium solution (2.5 M in hexane), is reacted with 200 mg of ketone 234 analogously to 12., and 341 mg of (7E)-(1R,3R)-1,3-bis[[(1,1-dimethylethyl)dimethylsilyl]oxy]-24a-fluoro-24a-(thiazol-2-yl)-24a-homo-19-nor-9,10-secochola-5,7-diene 235 is obtained as a colorless foam.

$^1$H-NMR (CDCl$_3$): δ=0.06 ppm (s, 12H); 0.53 (s, 3H); 0.89 (s, 18H); 0.93 (d, 3H); 4.09 (m, 2H); 5.75 (dbr, 1H); 5.82 (d, 1H); 6.18 (d, 1H); 7.39 (d, 1H); 7.80 (t, 1H)

228. 331 mg of fluoride 235 is treated analogously to 14., and after the diastereomers (in terms of C-24a) are separated by HPLC, 67 mg of title compound 236a and 69 mg of title compound 236b are obtained as colorless foams.

$^1$H-NMR (CD$_2$Cl$_2$): 236a: δ=0.52 ppm (s, 3H); 0.91 (d, 3H); 3.98 (m, 1H); 4.05 (m, 1H); 5.73 (dbr, 1H); 5.85 (d, 1H); 6.27 (d, 1H); 7.40 (d, 1H); 7.78 (t, 1H)

236b: δ=0.52 ppm (s, 3H); 0.91 (d, 3H); 3.97 (m, 1H); 4.04 (m, 1H); 5.74 (dbr, 1H); 5.85 (d, 1H); 6.27 (d, 1H); 7.40 (d, 1H); 7.78 (t, 1H)

Example 55

(5Z,7E)-(1S,3R,24aR)-24a-Fluoro-24a-(thiazol-2-yl)-24a-homo-9,10-secochola-5,7,10(19)-triene-1,3-diol 238a and (5Z,7E)-(1S,3R,24aS)-24a-fluoro-24a-(thiazol-2-yl)-24a-homo-9,10-secochola-5,7,10(19)-triene-1,3-diol 238b 229. 517 mg of phosphine oxide 17, which was deprotonated with 0.42 ml of n-butyllithium solution (2.5 M in hexane), is reacted with 150 mg of ketone 234 analogously to 15., and 293 mg of (5Z,7E)-(1S,3R)-1,3-bis[[(1,1-dimethylethyl)dimethylsilyl]oxy]-24a-fluoro-24a-(thiazol-2-yl)-24a-homo-9,10-secochola-5,7,10(19)-triene 237 is obtained as a colorless foam.

$^1$H-NMR (CDCl$_3$): δ=0.07 ppm (s, 12H); 0.54 (s, 3H); 0.92 (s, 18H); 0.96 (d, 3H); 4.20 (m, 1H); 4.39 (m, 1H); 4.89 (s, 1H); 5.20 (s, 1H); 5.77 (dbr, 1H); 6.05 (d, 1H); 6.25 (d, 1H); 7.40 (d, 1H); 7.80 (t, 1H)

230. 283 mg of fluoride 237 is treated analogously to 14., and after the diastereomers (in terms of C-24a) are separated by HPLC, 67 mg of title compound 238a and 59 mg of title compound 238b are obtained as colorless foams.

$^1$H-NMR (CD$_2$Cl$_2$): 238a: δ=0.52 ppm (s, 3H); 0.92 (d, 3H); 4.18 (m, 1H); 4.38 (m, 1H); 4.95 (s, 1H); 5.28 (s, 1H); 5.72 (dbr, 1H); 6.00 (d, 1H); 6.36 (d, 1H); 7.40 (d, 1H); 7.80 (t, 1H)

238b: δ=0.51 ppm (s, 3H); 0.89 (d, 3H); 4.11 (m, 1H); 4.33 (m, 1H); 4.90 (t, 1H); 4.92 (s, 1H); 5.27 (s, 1H); 6.00 (d, 1H); 6.32 (d, 1H); 7.29 (d, 1H); 7.68 (d, 1H)

Example 56

(7E)-(1R,3R,24aR)-24a-(Acetyloxy)-24a-(thiazol-2-yl)-24a-homo-19-nor-9,10-secochola-5,7-diene-1,3,24a-triol 239a and (7E)-(1R,3R,24aS)-24a-(acetyloxy)-24a-(thiazol-2-yl)-24a-homo-19-nor-9,10-secochola-5,7-diene-1,3,24a-triol 239b 231. 117 mg of acetate 25 is introduced into 6 ml of tetrahydrofuran, 0.9 ml of hydrogen fluoride-pyridine complex is added, and it is stirred for 4 hours at 25° C. The mixture is mixed with sodium bicarbonate solution, extracted with ethyl acetate, and the organic phase is washed with sodium chloride solution. After drying on sodium sulfate, the solvent is removed, and the residue is chromatographed on silica gel with ethyl acetate/hexane, whereby 72 mg of title compounds 239a and 239b are obtained as colorless oils. The separation of diastereomers is carried out on HPLC and yields 31 mg of title compound 239a and 26 mg of title compound 239b as colorless foams.

$^1$H-NMR (CD$_2$Cl$_2$): 239a: δ=0.51 ppm (s, 3H); 0.88 (d, 3H); 2.11 (s, 3H); 3.98 (m, 1H); 4.05 (m, 1H); 5.84 (d, 1H); 6.04 (dd, 1H); 6.37 (d, 1H); 7.31 (d, 1H); 7.71 (d, 1H)

239b: δ=0.51 ppm (s, 3H); 0.89 (d, 3H); 2.12 (s, 3H); 3.98 (m, 1H); 4.06 (m, 1H); 5.84 (d, 1H); 6.05 (dd, 1H); 6.37 (d, 1H); 7.31 (d, 1H); 7.71 (d, 1H)

Example 57

(7E)-(1R,3R,24aR)-24a-(2,2-Dimethyl-1-oxopropyl)oxy-24a-(thiazol-2-yl)-24a-homo-19-nor-9,10-secochola-5,7-diene-1,3,24a-triol 241a and (7E)-(1R,3R,24aS)-24a-(2,2-dimethyl-1-oxopropyl)oxy-24a-(thiazol-2-yl)-24a-homo-19-nor-9,10-secochola-5,7-diene-1,3,24a-triol 241b 232. 200 mg of alcohol 26 is introduced into 6 ml of pyridine, and it is stirred for 5 hours at 25° C. Then, it is quenched with sodium bicarbonate solution, extracted with ethyl acetate, and the organic phase is washed with sodium chloride solution. After drying on sodium sulfate, the solvent is removed, and the residue is chromatographed on silica gel with ethyl acetate/hexane, whereby 1120 mg of (7E)-(1R,3R)-1,3-bis[[(1,1-dimethylethyl)dimethylsilyl]oxy]-24a-(2,2-dimethyl-1-oxopropyl)oxy-24a-(thiazol-2-yl)-24a-homo-19-nor-9,10-secochola-5,7-diene 240 is obtained as a colorless foam.

$^1$H-NMR (CD$_2$Cl$_2$): δ=0.07 ppm (s, 3H); 0.53 (s, 3H); 0.89 (s, 18H); 0.92 (d, 3H); 1.23 (s, 9H); 3.98 (m, 1H); 4.05 (m, 1H); 5.84 (d, 1H); 6.03 (dd, 1H); 6.37-(d, 1H); 7.31 (d, 1H); 7.71 (d, 1H)

233. 120 mg of pivalate 240 is introduced into 7 ml of tetrahydrofuran, 0.4 ml of hydrogen fluoride-pyridine complex is added, and it is stirred for 4 hours at 25° C. The mixture is mixed with sodium bicarbonate solution, extracted with ethyl acetate, and the organic phase is washed with sodium chloride solution. After drying on sodium sulfate, the solvent is removed, and the residue is chromatographed on silica gel with ethyl acetate/hexane, whereby 74 mg of title compounds 241a and 241b are obtained as colorless oils. The separation of the diastereomers is carried out on HPLC and yields 28 mg of title compound 241a and 27 mg of title compound 241b as colorless foams.

$^1$H-NMR (CD$_2$Cl$_2$): 241a: δ=0.51 ppm (s, 3H); 0.88 (d, 3H); 1.24 (s, 9H); 3.98 (m, 1H); 4.05 (m, 1H); 5.84 (d, 1H); 6.05 (dd, 1H); 6.37 (d, 1H); 7.30 (d, 1H); 7.72 (d, 1H)

241b: δ=0.51 ppm (s, 3H); 0.88 (d, 3H); 1.23 (s, 9H); 3.98 (m, 1H); 4.06 (m, 1H); 5.84 (d, 1H); 6.05 (dd, 1H); 6.37 (d, 1H); 7.31 (d, 1H); 7.72 (d, 1H)

Example 58

(3R,5R)-3,5-Bis(benzoyloxy)-4-bromo-cyclohexan-1-one

234.

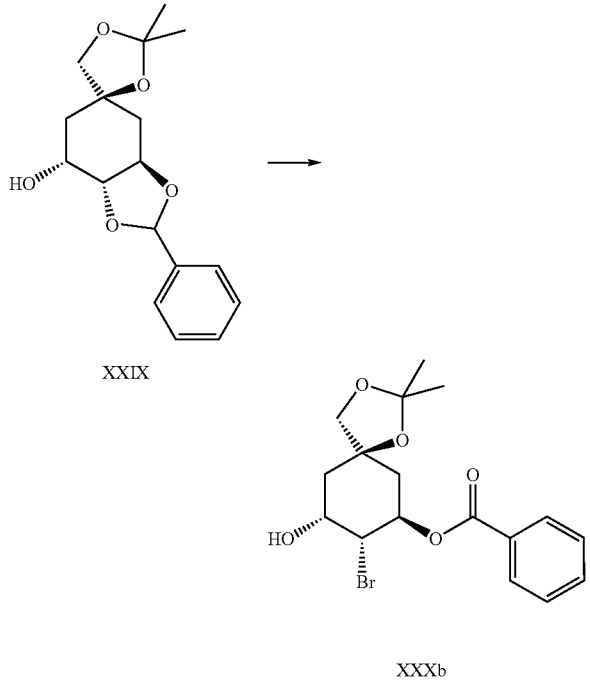

17.9 g of starting compound XXIX (synthesized according to J.-L. Montchamp, J. W. Frost J. Am. Chem. Soc. 113, 6296 (1991)) is dissolved in 500 ml of benzene. Then, 11.26 g of N-bromosuccinimide and a spatula tip full of AIBN are added and stirred for 1.5 hours. The almost bleached solution is extracted with ethyl acetate, washed with Na$_2$S$_2$O$_3$ solution and then washed with sodium chloride solution, dried and concentrated by evaporation. Column chromatography with hexane/ethyl acetate (1:1) yields 14.7 g of bromated product XXXb.

235.

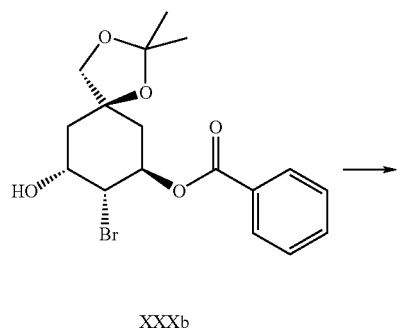

XXXb

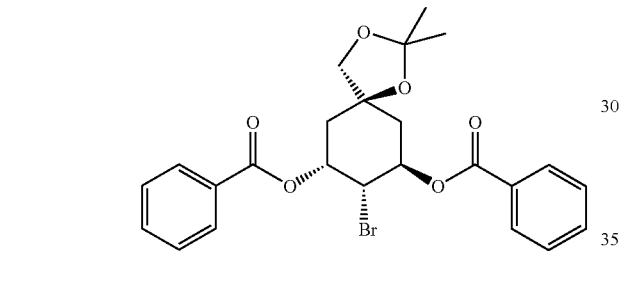

XXXIb 14.7 g of alcohol XXXb is introduced into 350 ml of pyridine and mixed with 12.8 ml of benzoyl chloride and a spatula tip full of DMAP (4-dimethylaminopyridine) and stirred for 12 hours at room temperature. Sodium bicarbonate is carefully added to the reaction mixture, stirred for 30 minutes, extracted with methylene chloride, dried on sodium sulfate and concentrated by evaporation. Column chromatography with ethyl acetate/hexane (1:9) yields 15.4 g of diester XXXIb.

236.

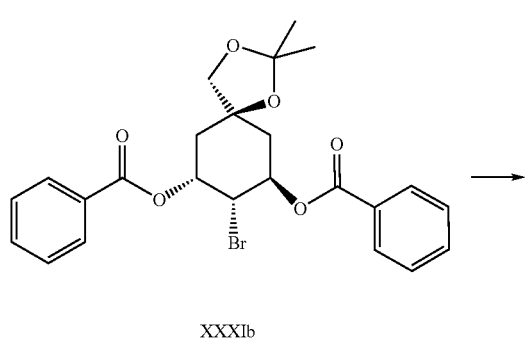

XXXIb

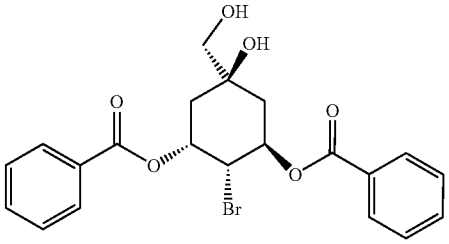

XXXIIb 15.4 g of diester, XXXIb from 235. is dissolved in 300 ml of methanol and mixed with 5.9 g of p-toluenesulfonic acid. The batch is stirred for 12 hours at room temperature. After 1 l of ethyl acetate is added, it is washed four times with sodium chloride solution, dried on sodium sulfate and concentrated by evaporation. Column chromatography with hexane/ethyl acetate yields 9.2 g of diol XXXIIb.

237.

XXXIIb

XXXIIIb 5 g of diol XXXIIb that is obtained from 236. is introduced into 200 ml of methanol. 8.31 g of sodium periodate in 60 ml of water is added in drops, and then it is stirred for one hour at 0° C. It is quenched with sodium chloride solution, extracted with ethyl acetate, dried and concentrated by evaporation. 4.68 g of crude product XXXIIIb is obtained, which is used without further purification in the Wittig reaction (Example 59, instructions 243, and 60, instructions 249).

Example 59

(7E)-(1R,3R)-2-Bromo-24a-(thiazol-2-yl)-24a-homo-19-nor-9,10-secochola-5,7-diene-1,3,24a-triol 238. [1R-[1α(1R*),3aβ,7aα]]-1-[5-(Hydroxy)-1-methyl-5-(thiazol-2-yl)pentyl]octahydro-7a-methyl-4H-inden-4-one 500 mg of [1R-[1α(1R*),3aβ,7aα]]-1-[5-(acetyloxy)-1-methyl-5-(thiazol-2-yl)pentyl]octahydro-7a-methyl-4H-inden-4-one 12 that can be obtained according to Example 1 is introduced into 30 ml of methanol and mixed with 800 mg of potassium carbonate. After 24 hours of stirring at room temperature, it is mixed with methylene chloride and washed with sodium chloride solution. After chromatography on silica gel with ethyl acetate/hexane, 440 mg of [1R-[1α(1R*),3aβ,7aα]]-1-[5-(hydroxy)-1-methyl-5-(oxazol-4-yl)pentyl]octahydro-7a-methyl-4H-inden-4-one is obtained.

239. [1R-[1α(1R*),3aβ,7aα]]-Octahydro-7a-methyl-1-[1-methyl-5-(thiazol-2-yl)-5-[(triethylsilyl)oxy]pentyl]-4H-inden-4-one 435 mg of [1R-[1α(1R*),3aβ,7aα]]-1-[5-(hydroxy)-1-methyl-5-(thiazol-2-yl)pentyl]octahydro-7a-methyl-4H-inden-4-one is mixed in 7 ml of DMF with 0.31 ml of chlorotriethylsilane and 151 mg of imidazole, and it is stirred for three days at room temperature. After extraction with ethyl acetate, washing with sodium chloride solution and drying, it is chromatographed with ethyl acetate/hexane. 584 mg of [1R-[1α(1R*),3aβ,7aα]]-octahydro-7a-methyl-1-[1-methyl-5-(thiazol-2-yl)-5-[(triethylsilyl)oxy]-pentyl]-4H-inden-4-one is obtained.

240. [[1R-[1α(1R*),3aβ,7aα]]-5-[(Triethylsilyl)oxy]-1-methyl-5-(thiazol-2-yl)pentyl]octahydro-7a-methyl-1H-inden-4-ylidine]acetic Acid Ethyl Ester Lithium diisopropyl amide is produced from 0.7 ml of diisopropylamine and 2 ml of n-butyllithium (2.5 M in hexane) in 14 ml of tetrahydrofuran, cooled to −78° C., and 0.95 ml of trimethylacetic acid ethyl ester in 1 ml of tetrahydrofuran is added in drops. After 20 minutes of stirring at −78° C., 584 mg of [1R-[1α(1R*),3aβ,7aα]]-octahydro-7a-methyl-1-[1-methyl-5-(thiazol-2-yl)-5-[(triethylsilyl)oxy]pentyl]-4H-inden-4-one in 2 ml of tetrahydrofuran is added. The reaction mixture is stirred at −78° C. until the reaction is completed according to TLC monitoring (ethyl acetate/hexane 2:8). After heating to room temperature, it is quenched with sodium chloride solution and extracted with ethyl acetate, the organic phase is washed with sodium chloride solution, dried on sodium sulfate and concentrated by evaporation. The residue is chromatographed with ethyl acetate/hexane on silica gel, whereby 700 mg of [[1R-[1α(1R*),3aβ,7aα]]-1-[5-[(triethylsilyl)oxy]-1-methyl-5-(thiazol-2-yl)pentyl]octahydro-7a-methyl-1H-inden-4-ylidene]acetic acid ethyl ester is obtained.

241. 2-[[1R-[1α(1R*),3aβ,7aα]]-1-[5-[(Triethylsilyl)oxy]-1-methyl-5-(thiazol-2-yl)pentyl]octahydro-7a-methyl-1H-inden-4-ylidene]ethanol 700 mg of [[1R-[1α(1R*),3aβ,7aα]]-1-[5-[(triethylsilyl)oxy]-1-methyl-5-(thiazol-2-yl)pentyl]octahydro-7a-methyl-1H-inden-4-ylidene]acetic acid ethyl ester is introduced into 30 ml of tetrahydrofuran at −20° C., and 4.3 ml of diisobutyl aluminum hydride solution is added in drops. It is stirred for 3 hours at −20° C. and then slowly heated to 0° C., and 0.6 ml of diisobutyl aluminum hydride solution is added once more. After 1 hour of stirring at 0° C., toluene is added, quenched with 1.5 ml of isopropanol/water (1:9) and suctioned off on Celite. The residue is concentrated by evaporation and chromatographed on silica gel (ethyl acetate/hexane). 385 mg of 2-[[1R-[1α(1R*),3aβ,7aα]]-1-[5-[(triethylsilyl)oxy]-1-methyl-5-(thiazol-2-yl)pentyl]octahydro-7a-methyl-1H-inden-4-ylidene]ethanol is obtained.

242. [2-[1R-[1α(1R*),3aβ,7aα]]-1-[1-Methyl-5-(thiazol-2-yl)-5-[(triethylsilyl)oxy]pentyl]octahydro-7a-methyl-1H-indenylidene]ethyl]diphenylphosphine oxide a) 385 mg of the alcohol 2-[[1R-[1α(1R*),3aβ,7aα]]-1-[5-[(triethylsilyl)oxy]-1-methyl-5-(thiazol-2-yl)pentyl]octahydro-7a-methyl-1H-inden-4-ylidene]-ethanol that is obtained from D is introduced into 2.5 ml of tetrahydrofuran at 0° C. and mixed drop by drop with 0.35 ml of n-butyllithium at 0° C. Then, 166 mg of tosyl chloride in 0.5 ml of tetrahydrofuran is added in drops and stirred for at least 5 more minutes at 0° C.

b) In a second flask, 0.3 ml of diphenylphosphine is introduced into 2 ml of tetrahydrofuran at 0° C. With dropwise addition of 0.7 ml of n-butyllithium, the solution is colored orange.

c) At 0° C., solution b) is now slowly added in drops to solution a) and stirred for 30 more minutes at 0° C. Then, it is quenched with water, the solution is concentrated by evaporation and taken up with a little methylene chloride. After cooling to 0° C., 0.3 ml of 10% hydrogen peroxide solution is added and stirred for one more hour at 0° C. Then, it is quenched with sodium thiosulfate solution, washed with sodium chloride solution and dried. After column chromatography, 471 mg of [2-[1R-[1α(1R*),3aβ,7aα]]-1-[1-methyl-5-(thiazol-2-yl)-5-[(triethylsilyl)oxy]pentyl]octahydro-7a-methyl-1H-indenylidene]ethyl]diphenylphosphine oxide is obtained.

243. (7E)-(1R,3R)-1,3-Bis-(benzoyloxy)-2-bromo-24a-(thiazol-2-yl)-24a-[(triethylsilyl)oxy]-24a-homo-19-nor-9,10-secochola-5,7-diene 471 mg of [2-[1R-[1α(1R*),3aβ,7aα]]-1-[1-methyl-5-(thiazol-2-yl)-5-[(triethylsilyl)oxy]-pentyl]octahydro-7a-methyl-1H-indenylidene]ethyl]diphenylphosphine oxide is introduced into 7 ml of tetrahydrofuran and cooled to −78° C. At this temperature, 0.26 ml of n-butyllithium solution is added and stirred for 10 more minutes at −30° C. Then, 446 mg of the ketone that is obtained from Example 57, instructions 235, is added into 3 ml of tetrahydrofuran as a crude product and stirred for 5 more hours at −30° C. (TLC monitoring of hexane/ethyl acetate 6:4). It is quenched with sodium chloride solution, extracted with ethyl acetate, washed with sodium chloride solution, dried on sodium sulfate and concentrated by evaporation. 913 mg of crude product (7E)-(1R,3R)-1,3-bis(benzoyloxy)-2-bromo-24a-(thiazol-2-yl)-24a-[(triethylsilyl)oxy]-24a-homo-19-nor-9,10-secochola-5,7-diene is obtained, which is further reacted without purification.

244. (7E)-(1R,3R)-1,3-Bis-(benzoyloxy)-2-bromo-24a-(thiazol-2-yl)-24a-homo-19-nor-9,10-secochola-5,7-dien-24a-ol 913 mg of crude product from Example 58F is introduced into 20 ml of tetrahydrofuran and mixed with 878 mg of tetrabutylammonium fluoride-hydrate. After 2 hours of stirring at room temperature, sodium bicarbonate solution is added, extracted with ethyl acetate, the organic phase is washed with sodium chloride solution and dried on sodium sulfate. After concentration by evaporation, the residue is further reacted as a crude product. 134 mg of (7E)-(1R,3R)-1,3-bis-(benzoyloxy)-2-bromo-24a-(thiazol-2-yl)-24a-homo-19-nor-9,10-secochola-5,7-dien-24a-ol is obtained as a crude product.

245. (7E)-(1R,3R)-2-Bromo-24a-(thiazol-2-yl)-24a-homo-19-nor-9,10-secochola-5,7-diene-1,3,24a-triol 134 mg of (7E)-(1R,3R)-1,3-bis-(benzoyloxy)-2-bromo-24a-(thiazol-2-yl)-24a-homo-19-nor-9,10-secochola-5,7-dien-24a-ol is introduced into 5 ml of tetrahydrofuran at 78° C., mixed with 0.44 ml of DIBAH/tetrahydrofuran, allowed to heat to 0° C., and stirring is continued after repeated addition of 3 ml of DIBAH. It is quenched with sodium chloride, extracted with ethyl acetate, dried on sodium sulfate and concentrated by evaporation. The crude product is chromatographed on silica gel. 24 mg of (7E)-(1R,3R)-2-bromo-24a-(thiazol-2-yl)-24a-homo-19-nor-9,10-secochola-5,7-diene-1,3,24a-triol is obtained.

Example 60

(7E)-(1R,3R)-2-Bromo-19-nor-9,10-secocholesta-5,7-diene-1,3,25-triol

246. [[1R-[1α(1R*),3aβ,7aα]]-1-[1,5,5-Trimethyl-5-[(trimethylsilyl)oxy]pentyl]octahydro-7a-methyl-1H-inden-4-ylidene]acetic acid ethyl ester 1.0 g of the compound [[1R-[1α(1R*),3aβ,7aα]]-1-[1,5,5-trimethyl-5-[(trimethylsilyl]oxy]pentyl]octahydro-7a-methyl-4H-inden-4-one that is known in the literature is reacted analogously to Example 59, instructions 240, and 1.03 g of [[1R-[1α(1R*),3aβ,7aα]]-1-[1,5,5-trimethyl-5-[(trimethylsilyl)oxy]pentyl]octahydro-7a-methyl-1H-inden-4-ylidene] acetic acid ethyl ester is obtained.

$^1$H-NMR (CDCl$_3$): δ=0.1 ppm (s, 9H); 0.59 ppm (s, 3H); 0.95 (d, 3H); 1.19 (s, 6H); 1.29 (t, 3H); 4.1 (q, 2H); 5.45 (s, 1H)

247. 2-[[1R-[1α(1R*),3aβ,7aα]]-1-[1,5,5-Trimethyl-5-[(trimethylsilyl)oxy]pentyl]-octahydro-7a-methyl-1H-inden-4-ylidene]ethanol 1.03 g of the compound that is obtained from Example 60, instructions 246, is reacted analogously to Example 59, instructions 241, and 535 mg of 2-[[1R-[1α(1R*),3aβ,7aα]]-1-[1,5,5-trimethyl-5-[(trimethylsilyl)oxy]pentyl]octahydro-7a-methyl-1H-inden-4-ylidene]ethanol is obtained.

$^1$H-NMR (CDCl$_3$): δ=0.1 ppm (s, 9H); 0.57 (s, 3H); 0.91 (d, 3H); 1.2 (s, 6H); 4.21 (d, 2H); 5.23 (t, 1H)

248. [1R-1α(1R*),3aβ,7aα]]-1-[5-[(Triethylsilyl)oxy]-1,5,5-trimethyl-5-(trimethyl-silyloxy)pentyl]octahydro-7a-methyl-1H-indenylidene]ethyl]diphenylphosphine oxide 535 mg of 2-[[1R-[1α(1R*),3aβ,7aα]]-1-[1,5,5-trimethyl-5-[(trimethylsilyl)oxy]pentyl]-octahydro-7a-methyl-1H-inden-4-ylidene]ethanol is reacted analogously to Example 59, instructions 242, and 318 mg of [1R-[1α(1R*),3aβ,7aα]]-1-[5-[(triethylsilyl)oxy]-1,5,5-trimethyl-5-(trimethylsilyloxy)pentyl]octahydro-7a-methyl-1H-indenylidene]ethyl]-diphenylphosphine oxide is obtained.

$^1$H-NMR (CDCl$_3$): δ=0.1 ppm (s, 9H); 0.3 (s, 3H); 0.88 (d, 3H); 1.2 (s, 6H); 3.05–3.34 (m, 2H); 5.0 (m, 1H); 7.45 (m, 6H); 7.73 (m, 4H)

249. (7E)-(1R,3R)-1,3-Bis(benzoyloxy)-2-bromo-25-[(trimethylsilyl)oxy]-19-nor-9,10-secocholesta-5,7-diene 445 mg of (7E)-(1R,3R)-1,3-bis(benzoyloxy)-2-bromo-25-[(trimethylsilyl)oxy]-19-nor-9,10-seococholesta-5,7-diene is obtained from 210 mg of [1R-[1α(1R*),3aβ,7aα]]-1-[5-[(triethylsilyl)oxy]-1,5,5-trimethyl-5-(trimethylsilyloxy)-pentyl]octahydro-7a-methyl-1H-indenylidene]ethyl]diphenyl-phosphine oxide analogously to Example 59, instructions 243.

$^1$H-NMR (CDCl$_3$): δ=0.1 ppm (s, 9H); 0.24 (s, 3H); 0.89 (d, 3H); 1.18 (s, 6H)

250. (7E)-(1R,3R)-1,3-Bis(benzoyloxy)-2-bromo-19-nor-9,10-secocholesta-5,7-dien-25-ol 170 mg of (7E)-(1R,3R)-1,3-bis(benzoyloxy)-2-bromo-19-nor-9,10-secocholesta-5,7-dien-25-ol, which is further reacted without purification, is obtained from 445 mg of (7E)-(1R,3R)-1,3-bis(benzoyloxy)-2-bromo-25-[(trimethylsilyl)oxy]-19-nor-9,10-secocholesta-5,7-diene analogously to Example 59, instructions 244.

251. (7E)-(1R,3R)-2-Bromo-19-nor-9,10-secocholesta-5,7-diene-1,3,25-triol 35 mg of (7E)-(1R,3R)-2-bromo-19-nor-9,10-secocholesta-5,7-diene-1,3,25-triol is obtained from 151 mg of (7E)-(1R,3R)-1,3-bis(benzoyloxy)-2-bromo-25-[(trimethylsilyl)oxy]-19-nor-9,10-secocholesta-5,7-diene analogously to Example 59, instructions 245.

$^1$H-NMR (CDCl$_3$): δ=0.52 ppm (s, 3H); 0.92 (d, 3H); 1.14 (s, 6H); 3.8 (d, 1H); 3.95–4.08 (2×m, 2H); 4.19 (dd, 1H); 6.27 (d, 1H).

The invention claimed is:
1. A compound formula I,

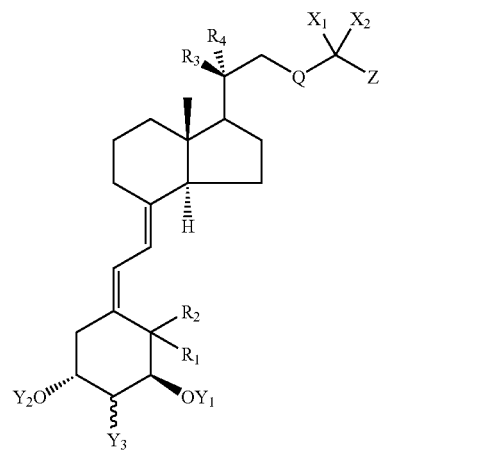

in which $Y_1$ and $Y_2$, independently of one another are, each a hydrogen atom or —C(O)R$_5$, $Y_3$ is a hydrogen atom, hydroxy, a halogen atom, —OC(O)R$_5$ or —OR$_5$, wherein $Y_3$ can be present in the 2α-situation or the epimeric 2β-situation, R$_5$ is an aromatic radical with 5 to 12 C atoms or an aliphatic, straight-chain or branched, saturated or unsaturated C$_1$–C$_{12}$ alkyl radical, which optionally is interrupted by 1–2 oxygen atoms, 1–2 sulfur atoms and/or 1–2 NH groups and/or optionally is substituted by 1–2 hydroxy groups, 1–2 amino groups, 1–2 SH groups, 1–2 COOH groups and/or 1–2 phenyl groups, R$_1$ and R$_2$ are each a hydrogen atom or together are an exocyclic methylene group, R$_3$ and R$_4$, independently of one another, are each a hydrogen atom, a fluorine, chlorine or bromine atom, an alkyl group with 1 to 4 carbon atoms, or together are a methylene group or together with quaternary carbon atom 20 a 3- to 7-membered, saturated or unsaturated carbocyclic ring, Q is a straight-chain alkylene group with 1 to 5 carbon atoms, $X_1$ and $X_2$ together are a double-bound keto-oxygen atom or, independently of one another, are each a hydrogen atom, a hydroxy group, —O(CO)R$_5$, or a fluorine, chlorine or bromine atom, wherein $X_1$ and $X_2$, are not both a hydroxy group or both an —O(CO)R$_5$ group, Z is an oxazole, thiazole, benzoxazole, or benzothiazole ring, which in each case is unsubstituted or substituted by one or more fluorine, chlorine, bromine or iodine atoms, one or more hydroxy groups, one or more COOR$_6$ groups, and/or one or more C$_1$–C$_5$ alkyl groups, which in turn can be substituted by one or more fluorine, chlorine, bromine or iodine atoms, C$_1$–C$_6$ alkoxy groups and/or COOR$_6$ groups, and R$_6$ is C$_1$–C$_6$ alkyl, benzyl or phenyl, and all possible epimers or diastereomers and mixtures thereof.

2. A compound according to claim 1, in which

R$_3$ or R$_4$ is hydrogen,

X$_1$ and X$_2$ together are a carbonyl group, or X$_1$ is a hydroxyl group or a fluorine atom and X$_2$ is a hydrogen atom, or X$_1$ a hydrogen atom and X$_2$ means is a hydroxyl group or a fluorine atom, or X$_1$ is an —OC(O)R$_5$ group and X$_2$ is a hydrogen atom, or X$_1$ is a hydrogen atom and X$_2$ is an —OC(O)R$_5$ group, and Z is oxazolyl, thiazolyl, or benzothiazolyl, which in each case is unsubstituted or substituted by one or more fluorine, chlorine, bromine or iodine atoms, one or more hydroxy groups, one or more COOR$_6$ groups, and/or one or more C$_1$–C$_5$ alkyl groups, which in turn can be substituted by one or more fluorine, chlorine, bromine or iodine atoms, C$_1$–C$_6$ alkoxy groups and/or COOR$_6$ groups.

3. A compound according to claim 1, in which the stereochemistry in 20-position is in the unnatural 20-epi-configuration.

4. A compound according to claim 1, wherein said compound is selected from:

(7E)-(1R,3R,24aR)-24a-(oxazole-4-yl)-24a-homo-19-nor-9,10-secochola-5,7-diene-1,3,24a-triol (7E)-(1R,3R,24aS)-24a-(oxazole-4-yl)-24a-homo-19-nor-9,10-secochola-5,7-diene-1,3,24a-triol (5Z,7E)-(1S,3R,24aR)-24a-(oxazole-4-yl)-24a-homo-9,10-secochola-5,7,10(19)-triene-1,3,24a-triol (5Z,7E)-(1S,3R,24aS)-24a-(oxazole-4-yl)-24a-homo-9,10-secochola-5,7,10(19)-triene-1,3,24a-triol (7E)-(1R,3R,24aR)-24a-(thiazole-2-yl)-24a-homo-19-nor-9,10-secochola-5,7-diene-1,3,24a-triol (7E)-(1R,3R,24aS)-24a-(thiazole-2-yl)-24a-homo-19-nor-9,10-secochola-5,7-diene-1,3,24a-triol (7E)-(1R,3R)-1,3-dihydroxy-24a-(thiazole-2-yl)-24-a-homo-19-nor-9,10-secochola-5,7-dien-24a-one (5Z,7E)-(1S,3R,24aR)-24a-(thiazole-2-yl)-24a-homo-9,10-secochola-5,7,10(19)-triene-1,3,24a-triol (5Z,7E)-(1S,3R,24aS)-24a-(thiazole-2-yl)-24a-homo-9,10-secochola-5,7,10(19)-triene-1,3,24a-triol (5Z,7E)-(1S,3R)-1,3-dihydroxy-24a-(thiazole-2-yl)-24a-homo-9,10-secochola-5,7,10(19)-trien-24a-one (7E)-(1R,3R,24aR)-24a-(4-methylthiazole-2-yl)-24a-homo-19-nor-9,10-secochola-5,7-diene-1,3,24a-triol (7E)-(1R,3R,24aS)-24a-(4-methylthiazole-2-yl)-24a-homo-19-nor-9,10-secochola-5,7-diene-1,3,24a-triol (7E)-(1R,3R)-1,3-dihydroxy-24a-(4-methylthiazole-2-yl)-24a-homo-19-nor-9,10-secochola-5,7-dien-24a-one (5Z,7E)-(1S,3R,24aR)-24a-(4-methylthiazole-2-yl)-24a-homo-9,10-secochola-5,7,10(19)-triene-1,3,24a-triol (5Z,7E)-(1S,3R,24aS)-24a-(4-methylthiazole-2-yl)-24a-homo-9,10-secochola-5,7,10(19)-triene-1,3,24a-triol (5Z,7E)-(1S,3R)-1,3-dihydroxy-24a-(4-methylthiazole-2-yl)-24a-homo-9,10-secochola-5,7,10(19)-trien-24a-one (7E)-(1R,3R,24aR)-24a-[5-(2-hydroxyethyl)-4-methylthiazole-2-yl]-24a-homo-19-nor-9,10-secochola-5,7-diene-1,3,24a-triol (7E)-(1R,3R,24aS)-24a-[5-(2-hydroxyethyl)-4-methylthiazole-2-yl]-24a-homo-19-nor-9,10-secochola-5,7-diene-1,3,24a-triol (7E)-(1R,3R)-1,3-dihydroxy-24a-[5-(2-hydroxyethyl)-4-methylthiazole-2-yl]-24a-homo-19-nor-9,10-secochola-5,7-dien-24a-one (7E)-(1R,3R,24aR)-24a-(benzothiazole-2-yl)-24a-homo-19-nor-9,10-secochola-5,7-diene-1,3,24a-triol (7E)-(1R,3R,24aS)-24a-(benzothiazole-2-yl)-24a-homo-19-nor-9,10-secochola-5,7-diene-1,3,24a-triol (7E)-(1R,3R)-24a-(benzothiazole-2-yl)-1,3-dihydroxy-24a-homo-19-nor-9,10-secochola-5,7-dien-24a-one (7E)-(1R,3R,20S,24aR)-24a-(thiazole-2-yl)-24a-homo-19-nor-9,10-secochola-5,7-diene-1,3,24a-triol (7E)-(1R,3R,20S,24aS)-24a-(thiazole-2-yl)-24-a-homo-19-nor-9,10-secochola-5,7-diene-1,3,24a-triol (7E)-(1R,3R,20S)-1,3-dihydroxy-24a-(thiazole-2-yl)-24-a-homo-19-nor-9,10-secochola-5,7-dien-24a-one (5Z,7E)-(1S,3R,20S,24aR)-24a-(thiazole-2-yl)-24a-homo-9,10-secochola-5,7,10(19)-triene-1,3,24a-triol (5Z,7E)-(1S,3R,20S,24aS)-24a-(thiazole-2-yl)-24a-homo-9,10-secochola-5,7,10(19)-triene-1,3,24a-triol (5Z,7E)-(1S,3R,20S)-1,3-dihydroxy-24a-(thiazole-2-yl)-24a-homo-9,10-secochola-5,7,10(19)-trien-24a-one (5Z,7E)-(1S,3R,24S)-24-(thiazole-2-yl)-9,10-secochola-5,7,10(19)-triene-1,3,24-triol (5Z,7E)-(1S,3R,24R)-24-(thiazole-2-yl)-9,10-secochola-5,7,10(19)-triene-1,3,24-triol (5Z,7E)-(1S,3R)-1,3-dihydroxy-24-(thiazole-2-yl)-9,10-secochola-5,7,10(19)-trien-24-one (7E)-(1R,3R,20S,24aR)-24a-(oxazole-4-yl)-24a-homo-19-nor-9,10-secochola-5,7-diene-1,3,24a-triol (7E)-(1R,3R,20S,24aS)-24a-(oxazole-4-yl)-24-a-homo-19-nor-9,10-secochola-5,7-diene-1,3,24a-triol (7E)-(1R,3R,20S)-1,3-dihydroxy-24a-(oxazole-4-yl)-24-a-homo-19-nor-9,10-secochola-5,7-dien-24a-one (5Z,7E)-(1S,3R,2,0S,24aR)-24a-(oxazole-4-yl)-24a-homo-9,10-secochola-5,7,10(19)-triene-1,3,24a-triol (5Z,7E)-(1S,3R,20S,24aS)-24a-(oxazole-4-yl)-24a-homo-9,10-secochola-5,7,10(19)-triene-1,3,24a-triol (5Z,7E)-(1S,3R,20S)-1,3-dihydroxy-24a-(oxazole-4-yl)-24a-homo-9,10-secochola-5,7,10(19)-trien-24a-one (5Z,7E)-(1S,3R,24R)-24-(oxazole-4-yl)-9,10-secochola-5,7,10(19)-triene-1,3,24a-triol (5Z,7E)-(1S,3R,24S)-24-(oxazole-4-yl)-9,10-secochola-5,7,10(19)-triene-1,3,24a-triol (5Z,7E)-(1S,3R)-1,3-dihydroxy-24-(oxazole-4-yl)-9,10-secochola-5,7,10(19)-trien-24-one (7E)-(1R,3R,20S,24aR)-24a-(4-methylthiazole-2-yl)-24a-homo-19-nor-9,10-secochola-5,7-diene-1,3,24a-triol (7E)-(1R,3R,20S,24aS)-24a-(4-methylthiazole-2-yl)-24-a-homo-19-nor-9,10-secochola-5,7-diene-1,3,24a-triol (7E)-(1R,3R,20S)-1,3-dihydroxy-24a-(4-methylthiazole-2-yl)-24-a-homo-19-nor-9,10-secochola-5,7-dien-24a-one (5Z,7E)-(1S,3R,20S,24aR)-24a-(4-methylthiazole-2-yl)-24a-homo-9,10-secochola-5,7,10(19)-triene-1,3,24a-triol (5Z,7E)-(1S,3R,20S,24aS)-24a-(4-methylthiazole-2-yl)-24a-homo-9,10-secochola-5,7,10(19)-triene-1,3,24a-triol (5Z,7E)-(1S,3R,20S)-1,3-dihydroxy-24a-(4-methylthiazole-2-yl)-24a-homo-9,10-secochola-5,7,10(19)-trien-24a-one (5Z,7E)-(1S,3R,24R)-24-(4-methylthiazole-2-yl)-9,10-secochola-5,7,10(19)-triene-1,3,24a-triol (5Z,7E)-(1S,3R,24S)-24-(4-methylthiazole-2-yl)-9,10-secochola-5,7,10(19)-triene-1,3,24a-triol (5Z,7E)-(1S,3R)-1,3-dihydroxy-24-(4-methylthiazole-2-yl)-9,10-secochola-5,7,10(19)-trien-24-one (5Z,7E)-(1S,3R,24S)-24-(4-methylthiazole-2-yl)-9,10-secochola-5,7,10(19)-triene-1,3,24-triol (5Z,7E)-(1S,3R,24R)-24-(4-methylthiazole-2-yl)-9,10-secochola-5,7,10(19)-triene-1,3,24-triol (5Z,7E)-(1S,3R)-1,3-dihydroxy-24-(4-methylthiazole-2-yl)-9,10-secochola-5,7,10(19)-trien-24-one (7E)-(1R,3R,24aR)-24a-fluoro-24a-(thiazole-2-yl)-24a-homo-19-nor-9,10-secochola-5,7-diene-1,3-diol (7E)-(1R,3R,24aS)-24a-fluoro-24a-(thiazole-2-yl)-24a-homo-19-nor-9,10-secochola-5,7-diene-1,3-diol (5Z,7E)-(1S,3R,24aR)-24a-fluoro-24a-(thiazole-2-yl)-24a-homo-9,10-secochola-5,7,10(19)-triene-1,3-diol (5Z,7E)-(1S,3R,24aS)-24a-fluoro-24a-(thiazole-2-yl)-24a-homo-9,10-secochola-5,7,10(19)-triene-1,3-diol (7E)-(1R,3R,24aR)-24a-(acetyloxy)-24a-(thiazole-2-yl)-24a-homo-19-nor-9,10-secochola-5,7-diene-1,3,24a-triol (7E)-(1R,3R,24aS)-24a-(acetyloxy)-24a-(thiazole-2-yl)-24a-homo-19-nor-9,10-secochola-5,7-diene-1,3,24a-triol (7E)-(1R,3R,24aR)-24a-(2,2-dimethylpropanoyloxy)-24a-(thiazole-2-yl)-24a-homo-19-nor-9,10-secochola-5,7-diene-1,3,24a-triol (7E)-(1R,3R,24aS)-24a-(2,2-dimethylpropanoyloxy)-24a-(thiazole-2-yl)-24a-homo-19-nor-9,10-secochola-5,7-diene-1,3,24a-triol and (7E)-(1R,3R)-2-bromo-24a-(thiazole-2-yl)-24a-homo-19-nor-9,10-secochola-5,7-diene-1,3,24a-triol.

5. A process for production of a compound according to claim 1, in which Q is $C_2$–$C_5$ alkyl, said process comprising:

converting a compound of formula III

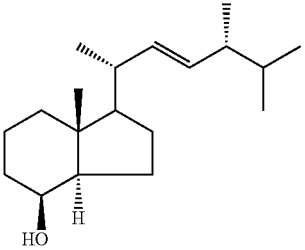

III by introduction of a protective group $Y_4$ to form a compound of formula IV

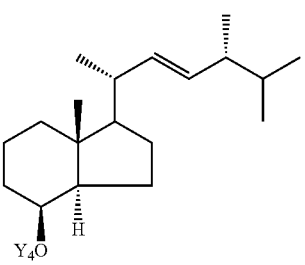

IV in which $Y_4$ is a trialkylsilyl protective group, a mixed aryl-alkyl-substituted silyl protective group, a tetrahydropyranyl group or a tetrahydrofuranyl protective group;

converting said compound of formula IV by oxidative cleavage of the double bond into a compound of formula V

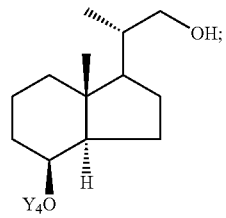

V converting the alcohol of formula IV by introduction of leaving group L to form a compound of formula VI

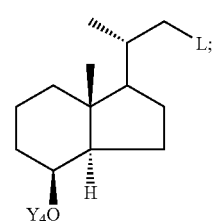

VI reacting a compound of formula VI with an alkinol of the following formula

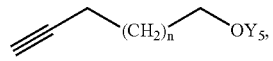

in which $Y_5$ is a tetrahydropyranyl group or a benzyl group, and n is 0, 1, 2, or 3, which is deprotonated with a base, to form a compound of formula VIIb

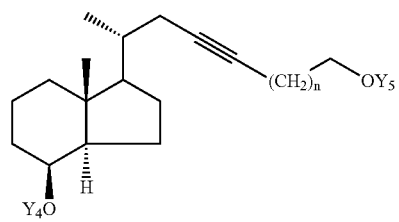

VIIb in which in any sequence the triple bond is hydrogenated and optionally the still present protective group $Y_5$ is cleaved to obtain a compound of formula VIIIb

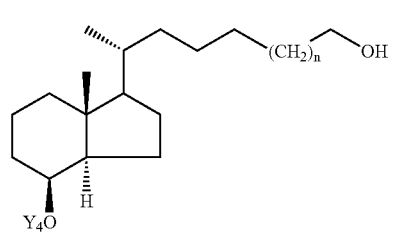

VIIIb whose free hydroxy group is then converted with an oxidizing agent, to form an aldehyde of formula IXb,

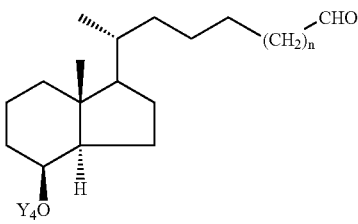

which is converted by reaction with a nucleophile Z',
which represents any nucleophilic form of radical Z, conversion of the free hydroxy group into a group OCOR' with R' being $C_1$–$C_5$ alkyl, cleavage of protective group $Y_4$ and oxidation of the free hydroxy group, to form a ketone of formula XIIIb,

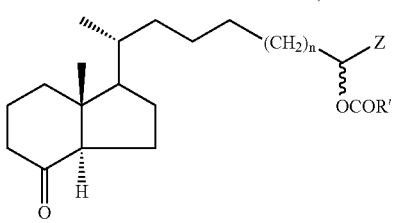

which then is converted by Wittig reaction with a phosphonate of formulas XIV, XV or XVI

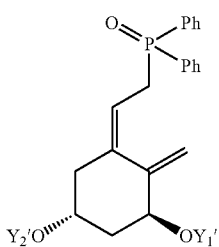

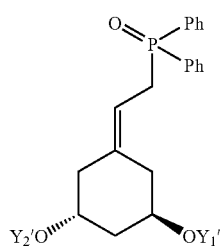

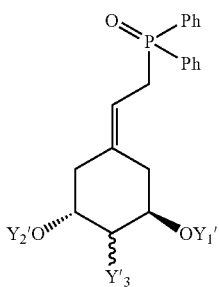

and
cleaving protective groups to form a compound of formula I.

6. A pharmaceutical preparations comprising at least one compound according to claim 1 and a pharmaceutically compatible adjuvant or vehicle.

7. A compound according to claim 1, wherein —C(O)$R_5$ is derived from formic acid, acetic acid, propionic acid, butanoic acid, pentanoic acid or pivalic acid can be mentioned.

8. A compound according to claim 1, wherein $Y_1$ and $Y_2$, independently of one another, are each hydrogen, acetyl, propionyl or pivaloyl.

9. A compound according to claim 1, wherein $Y_3$ is hydrogen, fluorine, chlorine, bromine, hydroxy, $OR_5$ or —OC(O)$R_5$.

10. A compound according to claim 1, wherein $Y_3$ methoxy, ethoxy, propoxy, isopropoxy, butoxy, isobutoxy, or t-butoxy.

11. A compound according to claim 1, wherein $R_3$ and $R_4$, independently of one another, are each fluorine, chlorine, bromine atom, or alkyl with 1 to 4 carbon atoms, or together are a methylene group or together with quaternary carbon atom 20 are a 3- to 7-membered, saturated or unsaturated carbocyclic ring.

12. A compound according to claim 1, wherein $R_3$ is H, and $R_4$ is methyl; $R_3$ is methyl, and $R_4$ is H; $R_3$ and $R_4$ are each methyl; $R_3$ and $R_4$ together form a methylene group; or $R_3$ and $R_4$ together with tertiary carbon atom 20 form a cyclopropyl ring.

13. A compound according to claim 1, wherein $R_5$ is methyl, ethyl, propyl, i-propyl, butyl or phenyl.

14. A compound according to claim 1, wherein $R_5$ is derived from a $C_1$ to $C_9$ alkanecarboxylic acid.

15. A compound according to claim 1, wherein $R_6$ is methyl, ethyl, propyl, butyl, isobutyl, tert-butyl, pentyl, isopentyl, neopentyl or hexyl.

16. A compound according to claim 1, wherein $R_6$ is benzyl or phenyl which is unsubstituted or substituted by one or more halogen atom(s), hydroxy group(s), $C_1$–$C_4$ alkoxy group(s), $CF_3$ group(s) or amino group(s).

17. A compound according to claim 1, wherein Q is methylene, ethylene or propylene.

18. A compound according to claim 1, wherein $X_1$ and $X_2$ together are a carbonyl group, or $X_1$ is hydroxyl or fluorine and $X_2$ is hydrogen, or $X_1$ is hydrogen $X_2$ is hydroxyl or fluorine, or $X_1$ is —OC(O)$R_6$ and $X_2$ is hydrogen, or $X_1$ is hydrogen and $X_2$ is —OC(O)$R_6$.

19. A compound according to claim 1, wherein Z is a oxazole or thiazole ring, which can carry one or more methyl, ethyl or propyl groups at any position(s), which in turn can be substituted by halogen.

20. A compound according to claim 1, wherein Z is a benzoxazole or benzothiazole ring, which can carry methyl, ethyl or propyl groups at any position, which in turn can be substituted by halogen.

21. A compound according to claim 1, wherein said compound is selected from:

(7E)-(1R,3R,24aR)-24a-(oxazole-4-yl)-24a-homo-19-nor-9,10-secochola-5,7-diene-1,3,24a-triol, (7E)-(1R,3R,24aS)-24a-(oxazole-4-yl)-24a-homo-19-nor-9,10-secochola-5,7-diene-1,3,24a-triol, (5Z,7E)-(1S,3R,24aR)-24a-(oxazole-4-yl)-24a-homo-9,10-secochola-5,7,10(19)-triene-1,3,24a-triol, (5Z,7E)-(1S,3R,24aS)-24a-(oxazole-4-yl)-24a-homo-9,10-secochola-5,7,10(19)-triene-1,3,24a-triol, (7E)-(1R,3R,20S,24aR)-24a-(oxazole-4-yl)-24a-homo-19-nor-9,10-secochola-5,7-diene-1,3,24a-triol, (7E)-(1R,3R,20S,24aS)-24a-(oxazole-4-yl)-24-a-homo-
19-nor-9,10-secochola-5,7-diene-1,3,24-triol,
(7E)-(1R,3R,20S)-1,3-dihydroxy-24a-(oxazole-4-yl)-24-
a-homo-19-nor-9,10-secochola-5,7-dien-24a-one,
(5Z,7E)-(1S,3R,20S,24aR)-24a-(oxazole-4-yl)-24a-
homo-9,10-secochola-5,7,10(19)-triene-1,3,24a-triol,
(5Z,7E)-(1S,3R,20S,24aS)-24a-(oxazole-4-yl)-24a-
homo-9,10-secochola-5,7,10(19)-triene-1,3,24a-triol,
(5Z,7E)-(1S,3R,20S)-1,3-dihydroxy-24a-(oxazole-4-yl)-
24a-homo-9,10-secochola-5,7,10(19)-trien-24a-one,
(5Z,7E)-(1S,3R24R)-24-(oxazole-4-yl)-9,10-secochola-
5,7,10(19)-triene-1,3,24a-triol,
(5Z,7E)-(1 S,3R,24S)-24-(oxazole-4-yl)-9,10-secochola-
5,7,10(19)-triene-1,3,24a-triol, and
(5Z,7E)-(1S,3R)-1,3-dihydroxy-24-(oxazole-4-yl)-9,10-
secochola-5,7,10(19)-trien-24-one.

22. A compound according to claim 1, wherein said compound is selected from:
(7E)-(1R,3R,24aR)-24a-(thiazole-2-yl)-24a-homo-19-
nor-9,10-secochola-5,7-diene-1,3,24a-triol,
(7E)-(1R,3R,24aS)-24a-(thiazole-2-yl)-24a-homo-19-
nor-9,10-secochola-5,7-diene-1,3,24a-triol,
(7E)-(1R,3R)-1,3-dihydroxy-24a-(thiazole-2-yl)-24-a-
homo-19-nor-9,10-secochola-5,7-dien-24a-one,
(5Z,7E)-(1S,3R,24aR)-24a-(thiazole-2-yl)-24a-homo-9,
10-secochola-5,7,10(19)-triene-1,3,24a-triol,
(5Z,7E)-(1S,3R,24aS)-24a-(thiazole-2-yl)-24a-homo-9,
10-secochola-5,7,10(19)-triene-1,3,24a-triol,
(5Z,7E)-(1S,3R)-1,3-dihydroxy-24a-(thiazole-2-yl)-24a-
homo-9,10-secochola-5,7,10(19)-trien-24a-one,
(7E)-(1R,3R,24aR)-24a-(4-methylthiazole-2-yl)-24a-
homo-19-nor-9,10-secochola-5,7-diene-1,3,24a-triol,
(7E)-(1R,3R,24aS)-24a-(4-methylthiazole-2-yl)-24a-
homo-19-nor-9,10-secochola-5,7-diene-1,3,24a-triol,
(7E)-(1R,3R)-1,3-dihydroxy-24a-(4-methylthiazole-2-
yl)-24a-homo-19-nor-9,10-secochola-5,7-dien-24a-
one,
(5Z,7E)-(1S,3R,24aR)-24a-(4-methylthiazole-2-yl)-24a-
homo-9,10-secochola-5,7,10(19)-triene-1,3,24a-triol,
(5Z,7E)-(1,3R,24aS)-24a-(4-methylthiazole-2-yl)-24a-
homo-9,10-secochola-5,7,10(19)-triene-1,3,24a-triol,
(5Z,7E)-(1S,3R)-1,3-dihydroxy-24a-(4-methylthiazole-
2-yl)-24a-homo-9,10-secochola-5,7,10(19)-trien-24a-
one,
(7E)-(1R3R,24aR)-24a-[5-(2-hydroxyethyl)-4-methylthi-
azole-2-yl]-24a-homo-19-nor-9,10-secochola-5,7-di-
ene-1,3,24a-triol,
(7E)-(1R,3R,24aS)-24a-[5-(2-hydroxyethyl)-4-meth-
ylthiazole-2-yl]-24a-homo-19-nor-9,10-secochola-5,7-
diene-1,3,24a-triol,
(7E)-(1R,3R)-1,3-dihydroxy-24a-[5-(2-hydroxyethyl)-4-
methylthiazole-2-yl]-24a-homo-19-nor-9,10-seco-
chola-5,7-dien-24a-one,
(7E)-(1R,3R,20S,24aR)-24a-(thiazole-2-yl)-24a-homo-
19-nor-9,10-secochola-5,7-diene-1,3,24a-triol,
(7E)-(1R,3R,20S,24aS)-24a-(thiazole-2-yl)-24-a-homo-
19-nor-9,10-secochola-5,7-diene-1,3,24a-triol,
(7E)-(1R,3R,20S)-1,3-dihydroxy-24a-(thiazole-2-yl)-24-
a-homo-19-nor-9,10-secochola-5,7-dien-24a-one,
(5Z,7E)-(1S,3R,20S,24aR)-24a-(thiazole-2-yl)-24a-
homo-9,10-secochola-5,7,10(19)-triene-1,3,24a-triol,
(5Z,7E)-(1S,3R,20S,24aS)-24a-(thiazole-2-yl)-24a-
homo-9,10-secochola-5,7,10(19)-triene-1,3,24a-triol,
(5Z,7E)-(1S,3R,20S)-1,3-dihydroxy-24a-(thiazole-2-yl)-
24a-homo-9,10-secochola-5,7,10(19)-trien-24a-one,
(5Z,7E)-(1S,3R,24S)-24-(thiazole-2-yl)-9,10-secochola-
5,7,10(19)-triene-1,3,24-triol, (5Z,7E)-(1S,3R,24R)-24-(thiazole-2-yl)-9,10-secochola-
5,7,10(19)-triene-1,3,24-triol,
(5Z,7E)-(1S,3R)-1,3-dihydroxy-24-(thiazole-2-yl)-9,10-
secochola-5,7,10(19)-trien-24-one,
(7E)-(1R,3R,20S,24aR)-24a-(4-methylthiazole-2-yl)-
24a-homo-19-nor-9,10-secochola-5,7-diene-1,3,24a-
triol,
(7E)-(1R,3R,20S,24aS)-24a-(4-methylthiazole-2yl)24a-
homo 19-nor-9,10-secochola-5,7-diene-1,3,24a-triol,
(7E)-(1R,3R,20S)-1,3-dihydroxy-24a-(4-methylthiazole-
2-yl)-24-a-homo-19-nor-9,10-secochola-5,7-dien-24a-
one,
(5Z,7E)-(1S,3R,20S,24aR)-24a-(4-methylthiazole-2-yl)-
24a-homo-9,10-secochola-5,7,10(19)-triene-1,3,24a-
triol,
(5Z,7E)-(1S,3R,20S,24aS)-24a-(4-methylthiazole-2-yl)-
24a-homo-9,10-secochola-5,7,10(19)-triene-1,3,24a-
triol,
(5Z,7E)-(1S,3R,20S)-1,3-dihydroxy-24a-(4-methylthiaz-
ole-2-yl)-24a-homo-9,10-secochola-5,7,10(19)-trien-
24a-one,
(5Z,7E)-(1S,3R,24R)-24-(4-methylthiazole-2-yl)-9,10-
secochola-5,7,10(19)-triene-1,3,24a-triol,
(5Z,7E)-(1S,3R,24S)-24-(4-methylthiazole-2-yl)-9,10-
secochola-5,7,10(19)-triene-1,3,24a-triol,
(5Z,7E)-(1S,3R)-1,3-dihydroxy-24-(4-methylthiazole-2-
yl)-9,10-secochola-5,7,10(19)-trien-24-one,
(5Z,7E)-(1S,3R,24S)-24-(4-methylthiazole-2-yl)-9,10-
secochola-5,7,10(19)-triene-1,3,24-triol,
(5Z,7E)-(1S,3R,24R)-24-(4-methylthiazole-2-yl)-9,10-
secochola-5,7,10(19)-triene-1,3,24-triol,
(5Z,7E)-(1S,3R)-1,3-dihydroxy-24-(4-methylthiazole-2-
yl)-9,10-secochola-5,7,10(19)-trien-24-one,
(7E)-(1R,3R24aR)-24a-fluoro-24a-(thiazole-2-yl)-24a-
homo-19-nor-9,10-secochola-5,7-diene-1,3-diol,
(7E)-(1R,3R,24aS)-24a-fluoro-24a-(thiazole-2-yl)-24a-
homo-19-nor-9,10-secochola-5,7-diene-1,3-diol,
(5Z,7E)-(1S,3R,24aR)-24a-fluoro-24a-(thiazole-2-yl)-
24a-homo-9,10-secochola-5,7,10(19)-triene-1,3-diol,
(5Z,7E)-(1S,3R,24aS)-24a-fluoro-24a-(thiazole-2-yl)-
24a-homo-9,10-secochola-5,7,10(19)-triene-1,3-diol,
(7E)-(1R,3R,24aR)-24a-(acetyloxy)-24a-(thiazole-2-yl)-
24a-homo-19-nor-9,10-secochola-5,7-diene-1,3,24a-
triol,
(7E)-(1R,3R,24aS)-24a-(acetyloxy)-24a-(thiazole-2-yl)-
24a-homo-19-nor-9,10-secochola-5,7-diene-1,3,24a-
triol,
(7E)-(1R,3R,24aR)-24a-(2,2-dimethylpropanoyloxy)-
24a-(thiazole-2-yl)-24a-homo-19-nor-9,10-secochola-
5,7-diene-1,3,24a-triol,
(7E)-(1R,3R,24aS)-24a-(2,2-dimethylpropanoyloxy)-
24a-(thiazole-2-yl)-24a-homo-19-nor-9,10-secochola-
5,7-diene-1,3,24a-triol, and
(7E)-(1R,3R)-2-bromo-24a-(thiazole-2-yl)-24a-homo-
19-nor-9,10-secochola-5,7-diene-1,3,24a-triol.

23. A compound according to claim 1, wherein said compound is selected from:
(7E)-(1R,3R,24aR)-24a-(benzothiazole-2-yl)-24a-homo-
19-nor-9,10-secochola-5,7-diene-1,3,24a-triol,
(7E)-(1R,3R,24aS)-24a-(benzothiazole-2-yl)-24a-homo-
19-nor-9,10-secochola-5,7-diene-1,3,24a-triol, and
(7E)-(1R,3R)-24a-(benzothiazole-2-yl)-1,3-dihydroxy-
24a-homo-19-nor-9,10-secochola-5,7-dien-24a-one.

24. A compound according to claim 1, wherein said compound is selected from:
(7E)-(1R,3R,2aR)-24a-(oxazol-4-yl)-24a-homo-19-nor-
9,10-secochola-5,7-diene-1,3,24a-triol, (5Z,7E)-(1S,3R,24aR)-24a-(oxazol-4-yl)-24a-homo-9,10-secochola-5,7,10(19)-triene-1,3,24a-triol, and (5Z,7E)-(1S,3R,24R)-24-(thiazol-2-yl)-9,10-secochola-5,7,10(19)-triene-1,3,24a-triol.

25. A compound according to claim 1, wherein $R_1$ and $R_2$ together are methylene, $Y_3$ is H, and Z is a thiazole group which is unsubstituted or substituted by one or more fluorine, chlorine, bromine or iodine atoms, one or more hydroxy groups, one or more $COOR_6$ groups, and/or one or more $C_1$–$C_5$ alkyl groups, which in turn can be substituted by one or more fluorine, chlorine, bromine or iodine atoms, $C_1$–$C_6$ alkoxy groups and/or $COOR_6$ groups.

26. A compound according to claim 1, wherein Z is oxazolyl which is unsubstituted or substituted by one or more fluorine, chlorine, bromine or iodine atoms, one or more hydroxy groups, one or more $COOR_6$ groups, and/or one or more $C_1$–$C_5$ alkyl groups, which in turn can be substituted by one or more fluorine, chlorine, bromine or iodine atoms, $C_1$–$C_6$ alkoxy groups and/or $COOR_6$ groups.

27. A compound according to claim 1, wherein Z is thiazolyl which is unsubstituted or substituted by one or more fluorine, chlorine, bromine or iodine atoms, one or more hydroxy groups, one or more $COOR_6$ groups, and/or one or more $C_1$–$C_5$ alkyl groups, which in turn can be substituted by one or more fluorine, chlorine, bromine or iodine atoms, $C_1$–$C_6$ alkoxy groups and/or $COOR_6$ groups.

28. A compound according to claim 1, wherein Z is benzothiazolyl which is unsubstituted or substituted by one or more fluorine, chlorine, bromine or iodine atoms, one or more hydroxy groups, one or more $COOR_6$ groups, and/or one or more $C_1$–$C_5$ alkyl groups, which in turn can be substituted by one or more fluorine, chlorine, bromine or iodine atoms, $C_1$–$C_6$ alkoxy groups and/or $COOR_6$ groups.

29. A compound according to claim 1, wherein Z is benzoxazolyl which is unsubstituted or substituted by one or more fluorine, chlorine, bromine or iodine atoms, one or more hydroxy groups, one or more $COOR_6$ groups, and/or one or more $C_1$–$C_5$ alkyl groups, which in turn can be substituted by one or more fluorine, chlorine, bromine or iodine atoms, $C_1$–$C_6$ alkoxy groups and/or $COOR_6$ groups.

30. A compound according to claim 27, wherein $R_1$ and $R_2$ together are methylene.

31. A compound according to claim 27, wherein $Y_3$ is H.

* * * * *